(12) United States Patent
Onuki et al.

(10) Patent No.: US 8,465,499 B2
(45) Date of Patent: Jun. 18, 2013

(54) APPARATUS FOR LIGATING/SUTURING LIVING TISSUES AND SYSTEM FOR RESECTING/SUTURING LIVING TISSUES

(75) Inventors: Yoshio Onuki, Hino (JP); Satoshi Miyamoto, Nishitama-gun (JP); Koichi Kawashima, Hachioji (JP); Pankaj Jay Pasricha, Houston, TX (US)

(73) Assignees: Olympus Corporation, Tokyo (JP); Apollo Endosurgery, Inc., Austin, TX (US)

( * ) Notice: Subject to any disclaimer, the term of this patent is extended or adjusted under 35 U.S.C. 154(b) by 1164 days.

(21) Appl. No.: 11/657,328

(22) Filed: Jan. 24, 2007

(65) Prior Publication Data

US 2007/0135822 A1 Jun. 14, 2007

Related U.S. Application Data

(63) Continuation of application No. 10/430,071, filed on May 6, 2003, now Pat. No. 8,105,342.

(60) Provisional application No. 60/378,548, filed on May 8, 2002.

(51) Int. Cl.
*A61B 17/10* (2006.01)

(52) U.S. Cl.
USPC .......................................... 606/139; 606/144

(58) Field of Classification Search
USPC ................. 606/108, 139, 144, 145, 148, 158, 606/159; 600/564, 565, 566, 567, 562
See application file for complete search history.

(56) References Cited

U.S. PATENT DOCUMENTS

| | | | |
|---|---|---|---|
| 4,235,238 A | 11/1980 | Ogiu et al. | |
| 5,191,878 A | 3/1993 | Iida et al. | |
| 5,336,229 A | 8/1994 | Noda | |
| 5,792,153 A | 8/1998 | Swain et al. | |
| 5,908,429 A | 6/1999 | Yoon | |
| 6,066,146 A * | 5/2000 | Carroll et al. | 606/148 |
| 6,113,609 A * | 9/2000 | Adams | 606/139 |
| 6,328,730 B1 * | 12/2001 | Harkrider, Jr. | 604/523 |
| 6,358,197 B1 | 3/2002 | Silverman et al. | |
| 6,551,330 B1 | 4/2003 | Bain | |
| 2003/0171760 A1 | 9/2003 | Gambale | |
| 2005/0245945 A1 | 11/2005 | Ewers et al. | |

FOREIGN PATENT DOCUMENTS

| | | |
|---|---|---|
| GB | 2 165 559 B | 4/1986 |
| JP | 10-500318 | 1/1998 |
| JP | 2000-197639 | 7/2000 |

(Continued)

*Primary Examiner* — Tuan V Nguyen
(74) *Attorney, Agent, or Firm* — Scully, Scott, Murphy & Presser, P.C.

(57) ABSTRACT

A medical apparatus including: a projecting member; an introducing sheath; an extrusion member inside the introducing sheath, at a proximal side of the projecting member and movable in an axial direction with respect to the introducing sheath; a cover sheath outside the introducing sheath, the introducing sheath being movable between a first and second position with respect to the cover sheath; an introducing sheath manipulating section at a proximal side of the introducing sheath; an extrusion member manipulating section at a proximal side of the extrusion member; a cover sheath manipulating section at a proximal side of the cover sheath; and a release member on the cover sheath manipulating section and/or the introducing sheath manipulating section to release a fixation between the extrusion member manipulating section and the introducing sheath manipulating section when the introducing sheath is disposed on the first or second position.

6 Claims, 34 Drawing Sheets

FOREIGN PATENT DOCUMENTS

| | | |
|---|---|---|
| JP | 2001-502190 | 2/2001 |
| JP | 2002-45369 | 2/2002 |
| WO | WO 99/22649 | 5/1999 |
| WO | WO 01/28432 A1 | 4/2001 |
| WO | WO 01/89393 A1 | 11/2001 |

* cited by examiner

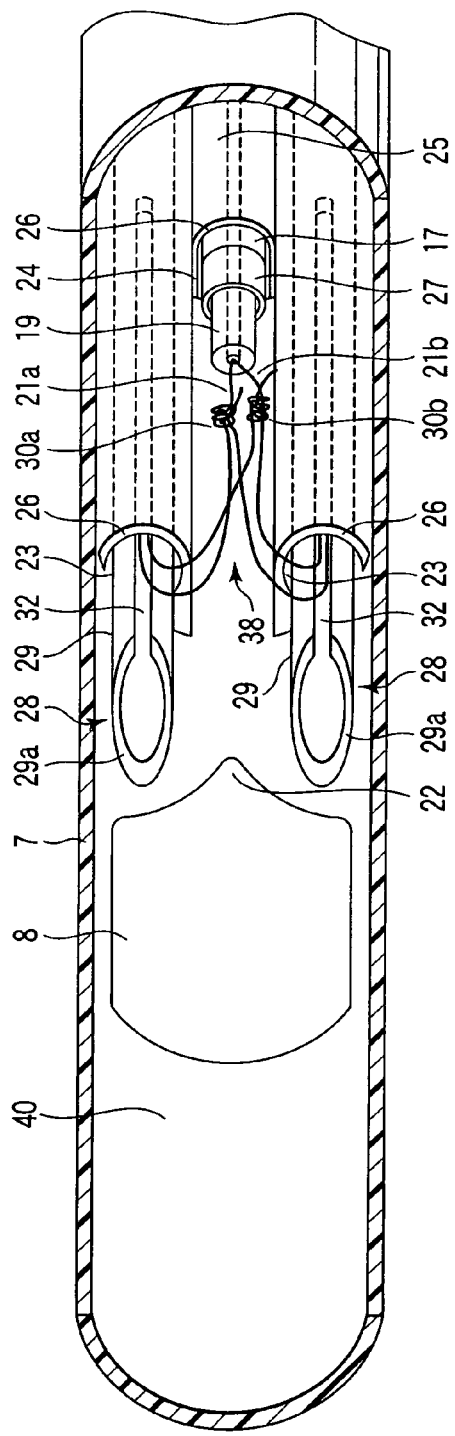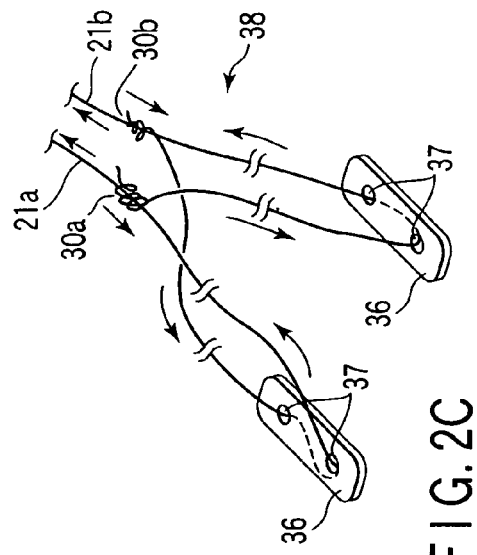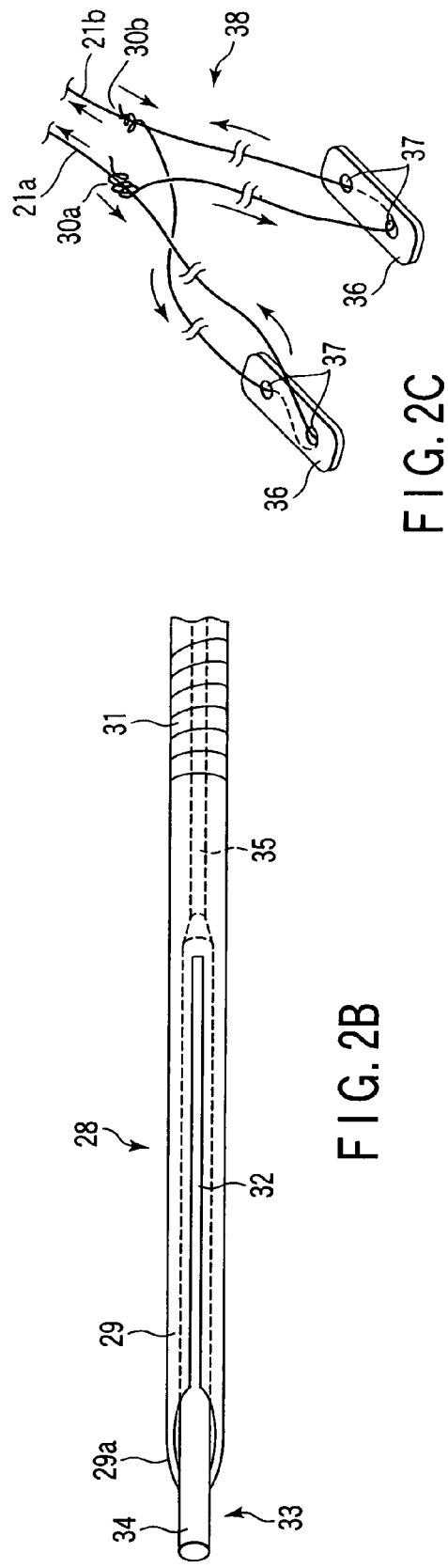
FIG. 2A
FIG. 2C
FIG. 2B

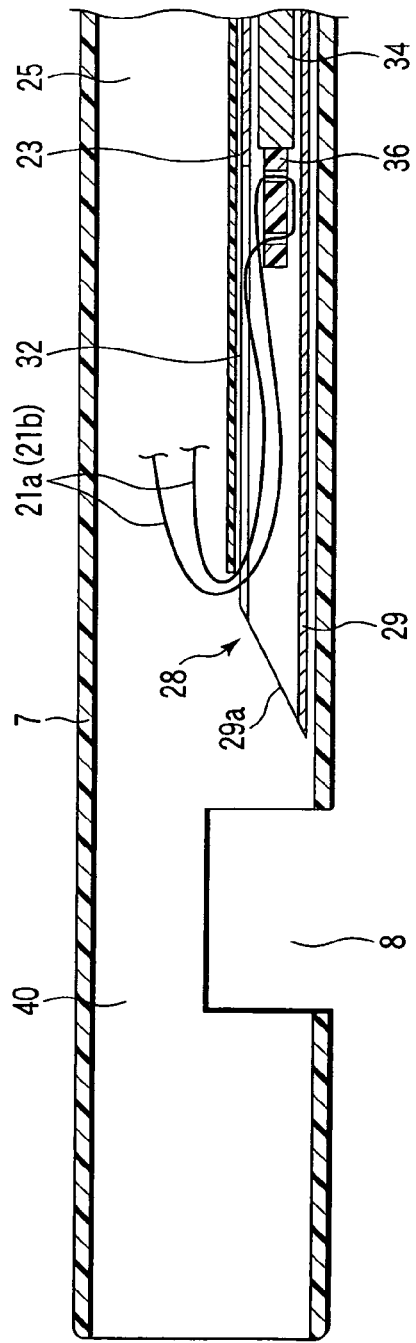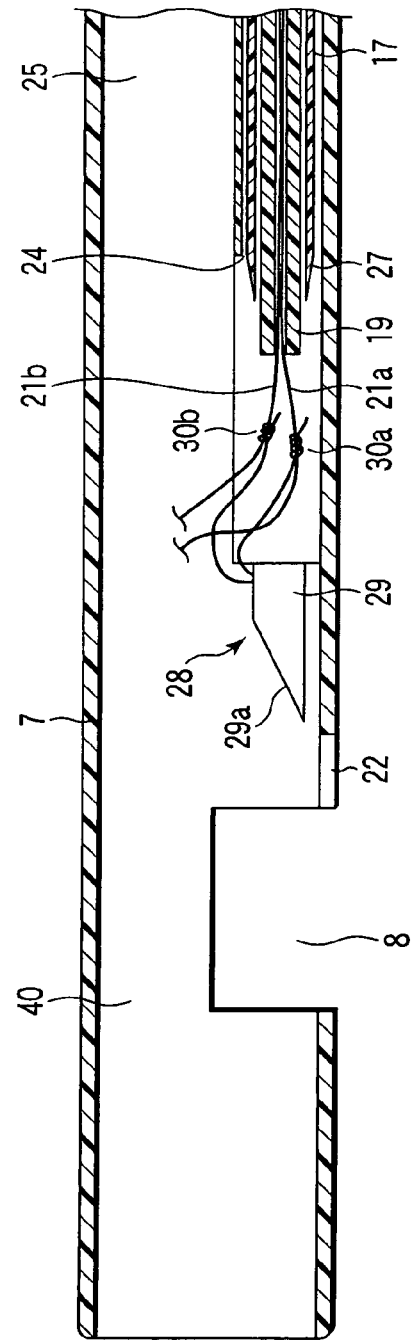
F I G. 5A    F I G. 5B

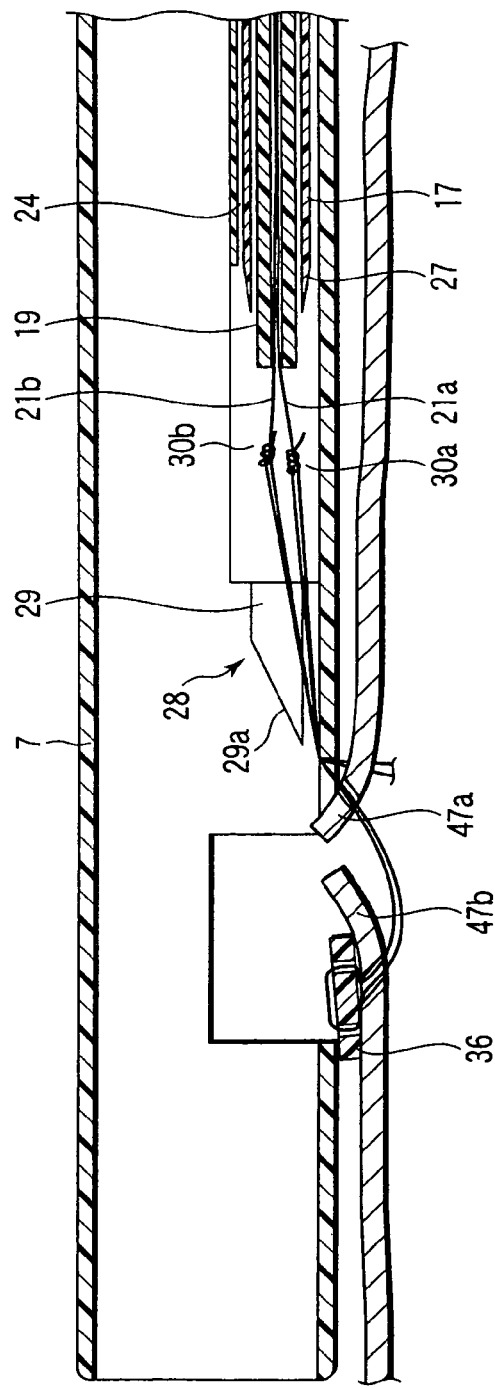
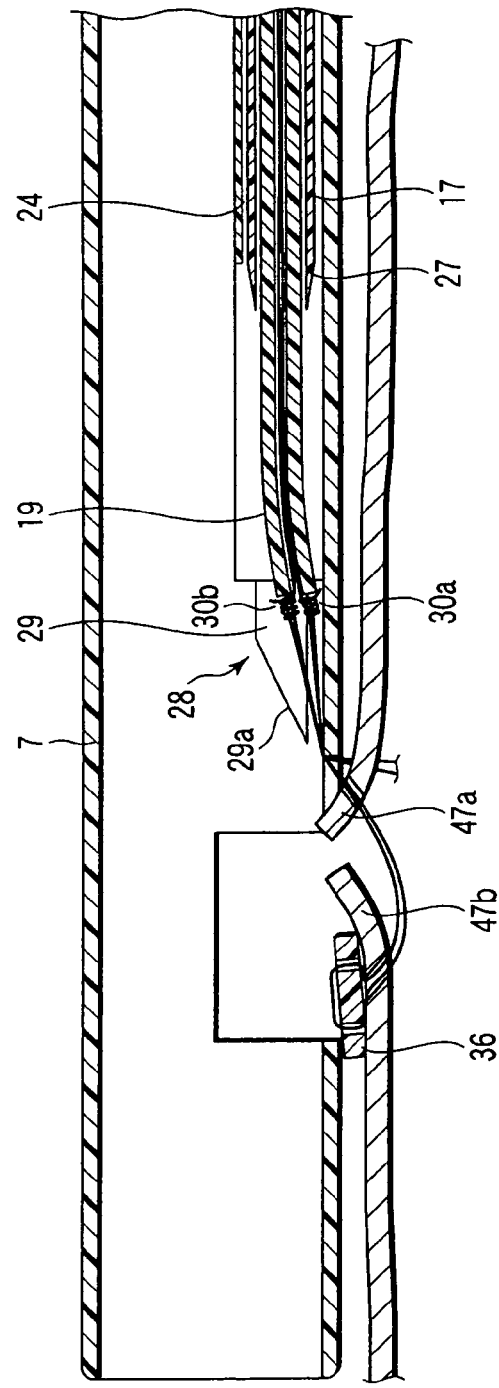
F I G. 7A
F I G. 7B

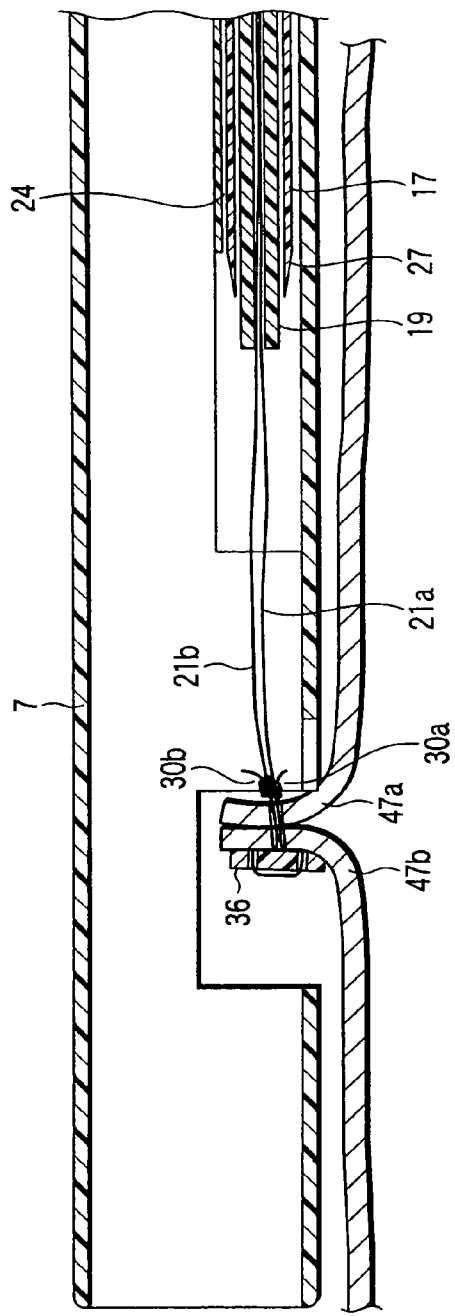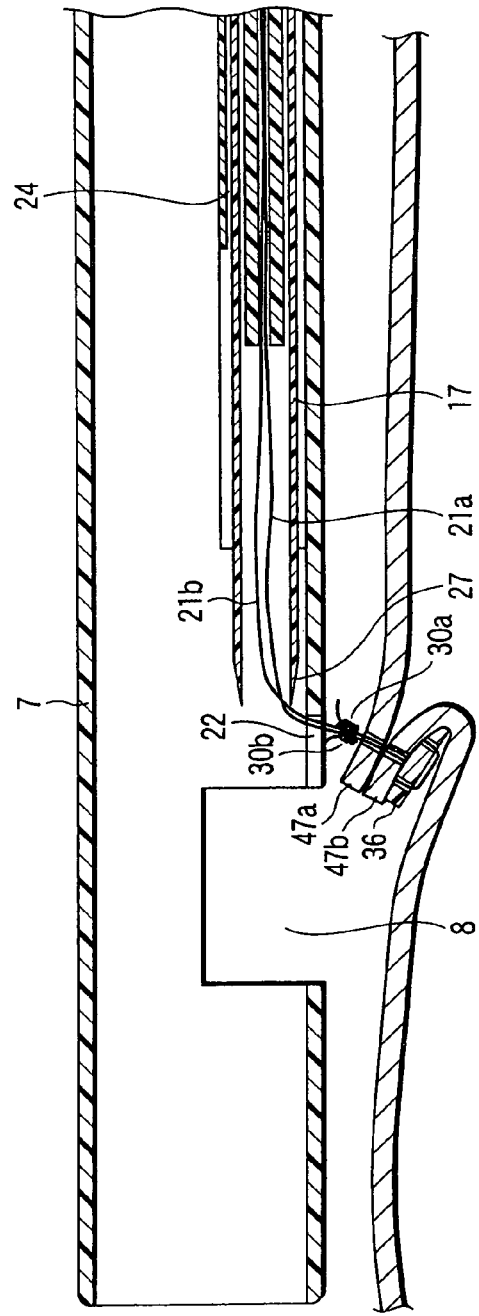
FIG. 8A
FIG. 8B

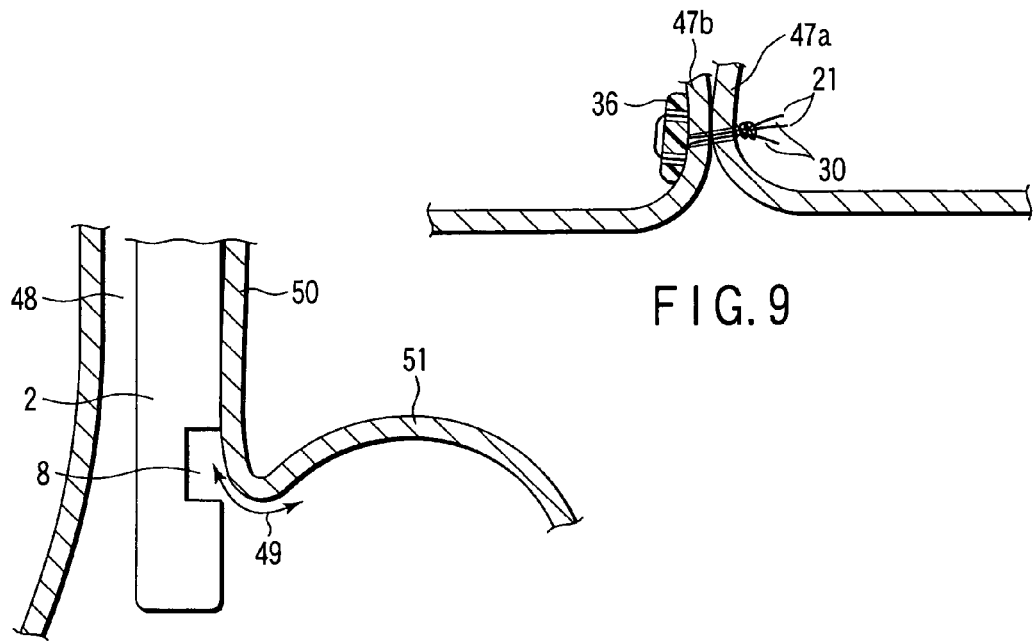
FIG. 9
FIG. 10
FIG. 11
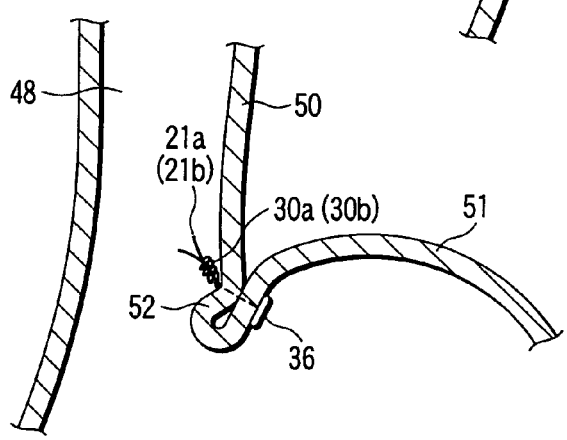
FIG. 12
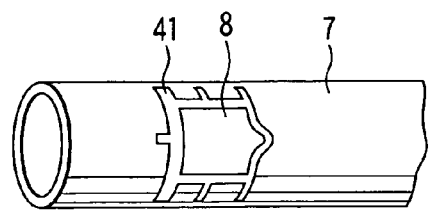
FIG. 13

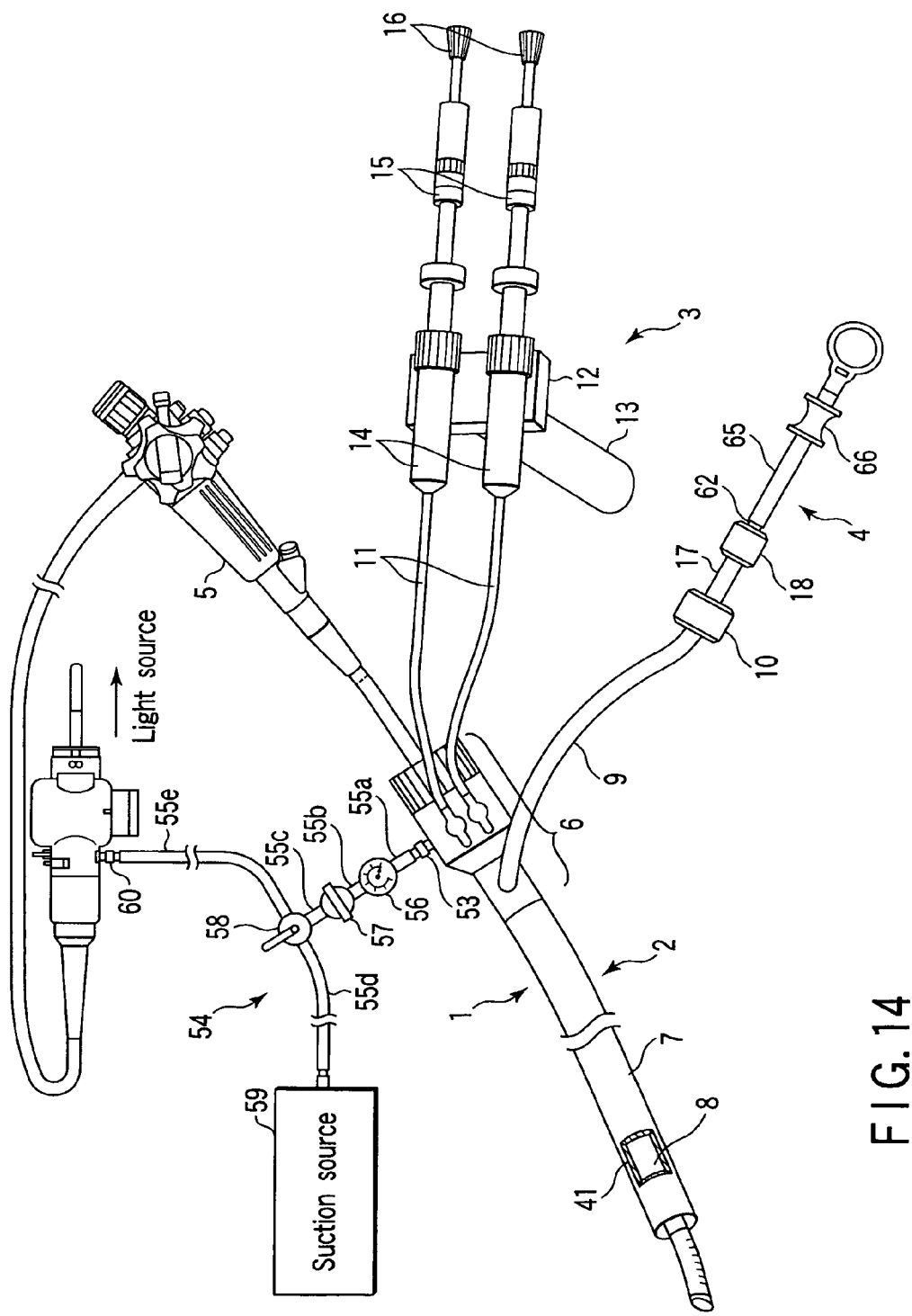
F I G. 14

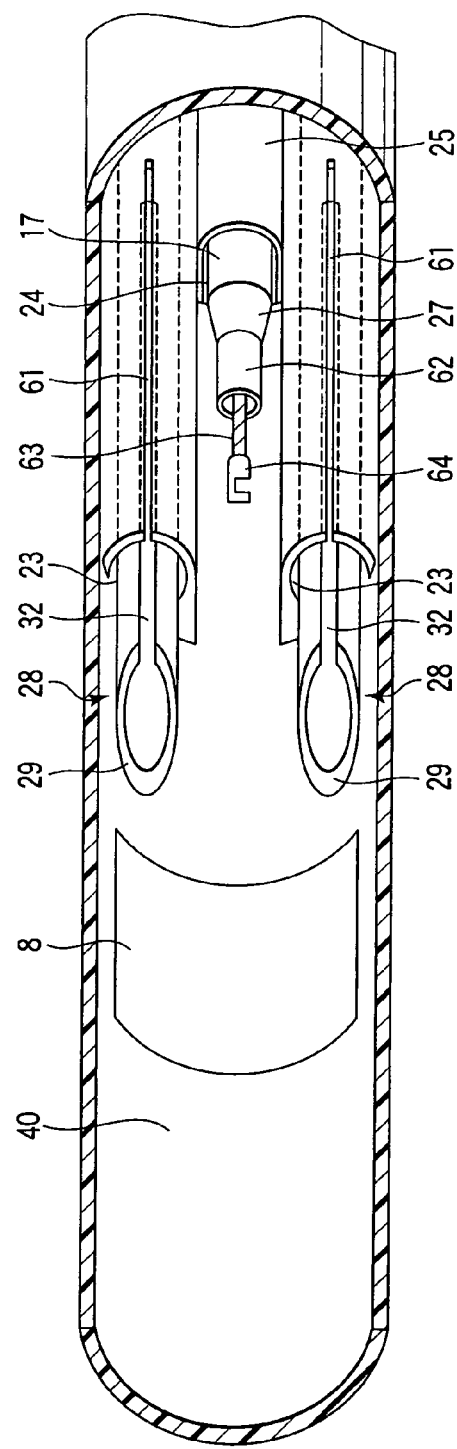
F I G. 15A
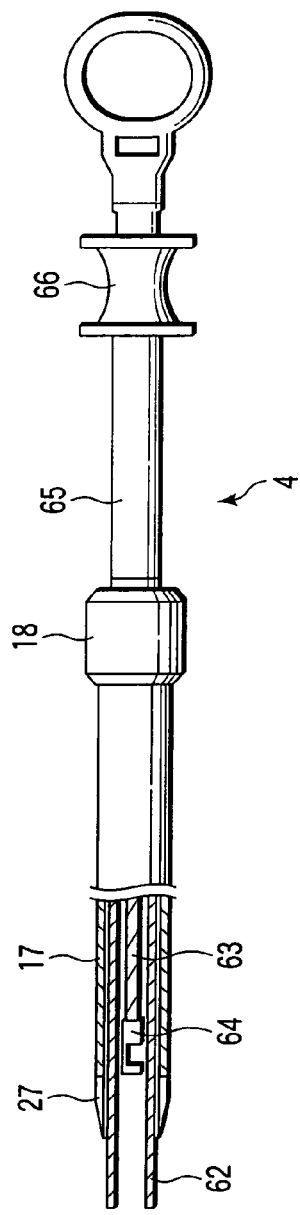
F I G. 15B

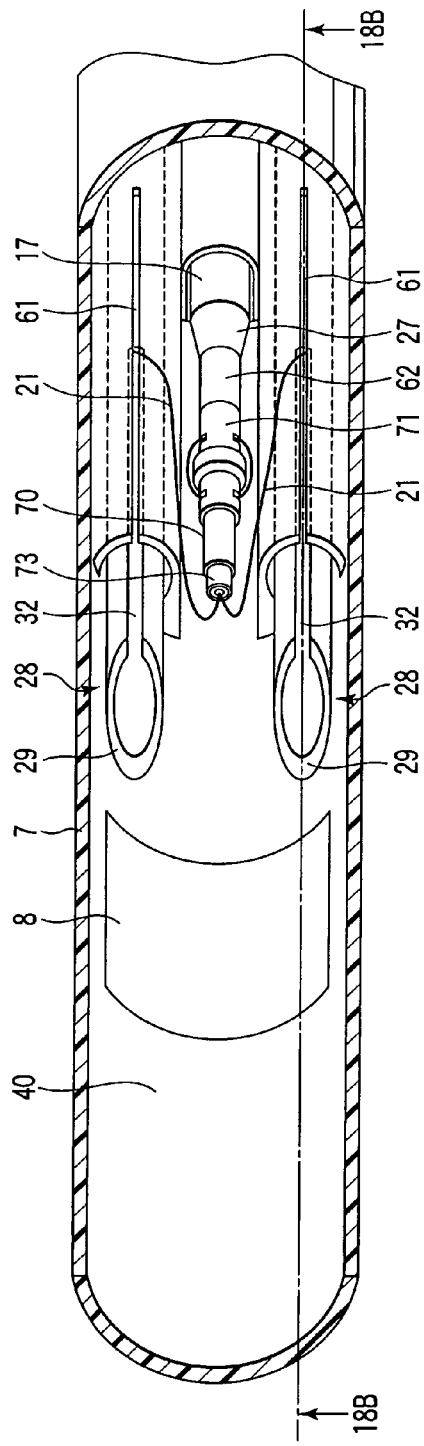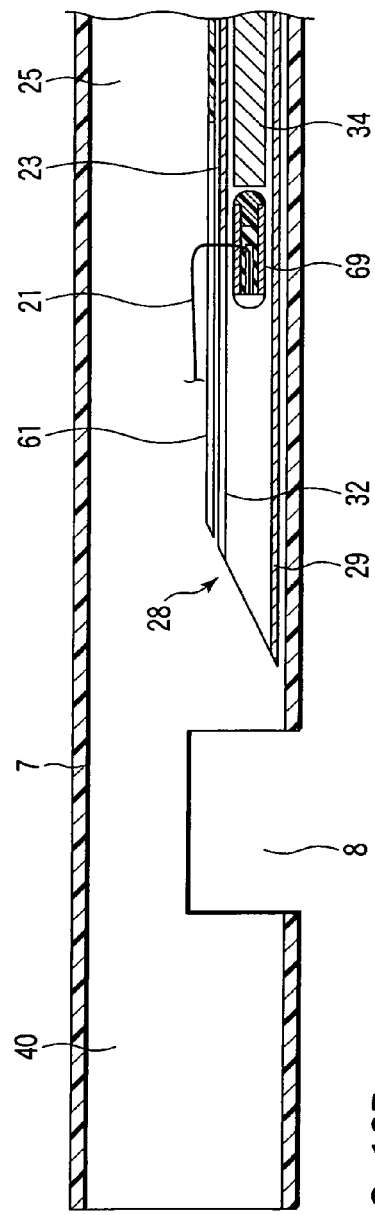
FIG. 18A
FIG. 18B

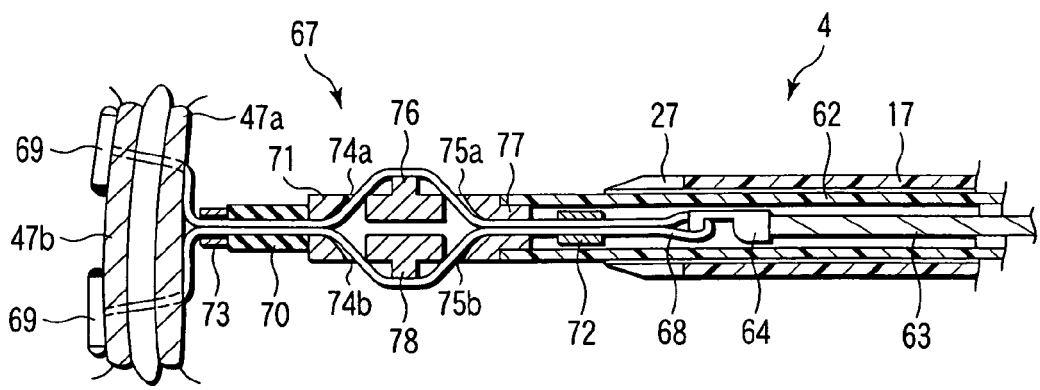
F I G. 19A
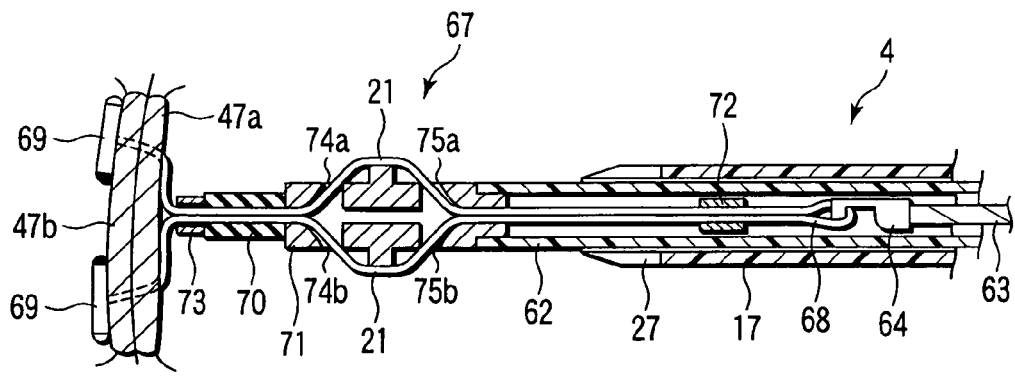
F I G. 19B
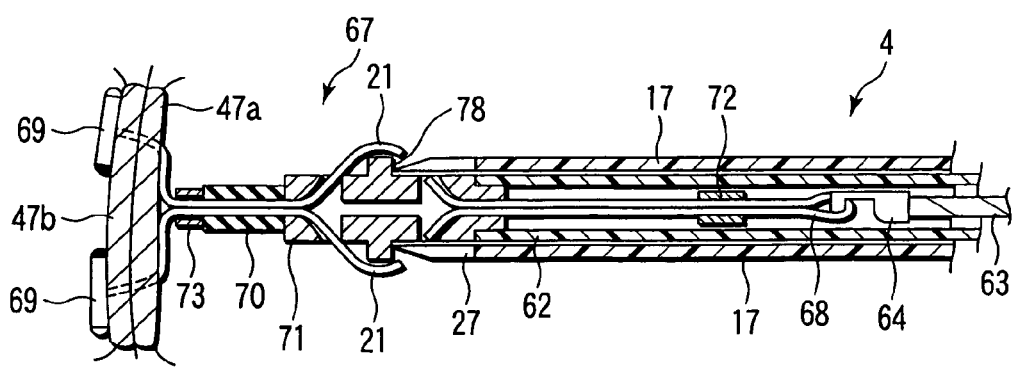
F I G. 19C

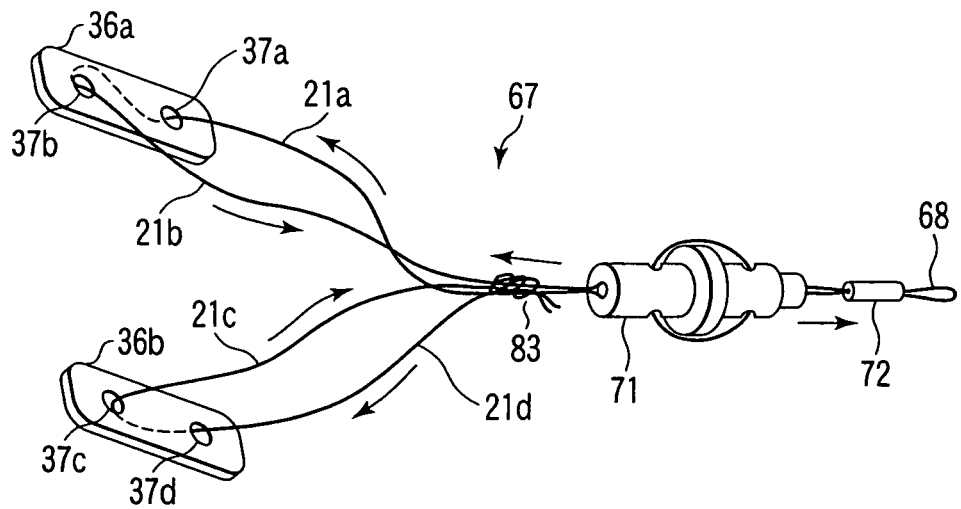
F I G. 22
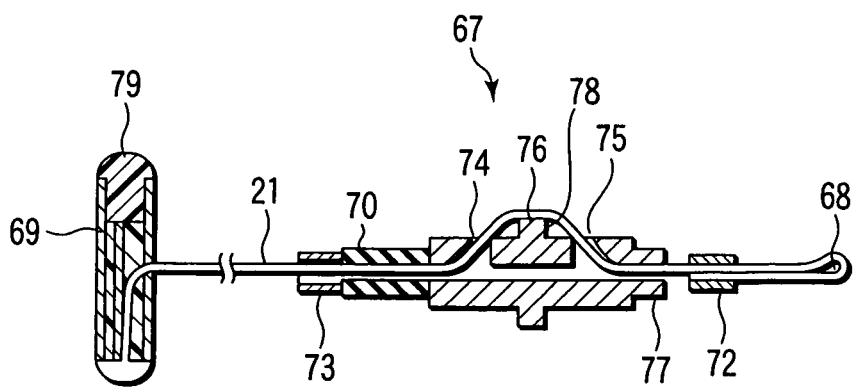
F I G. 23

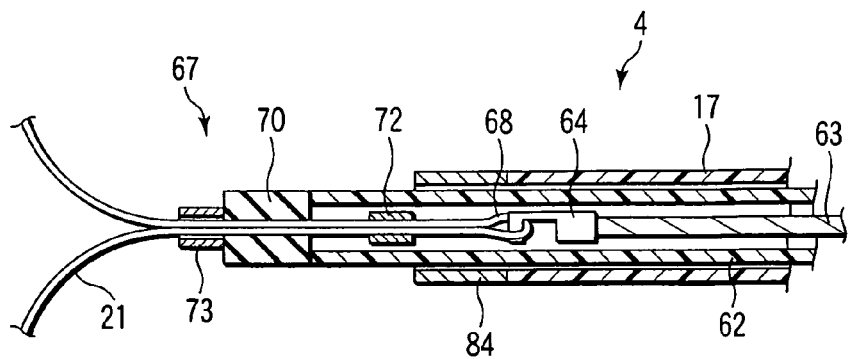
FIG. 24A
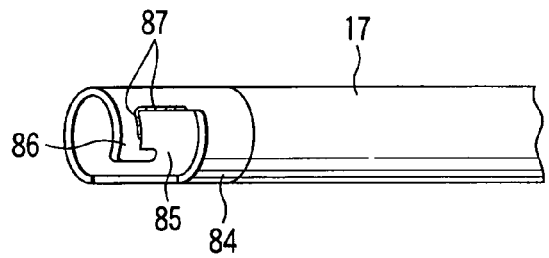
FIG. 24B
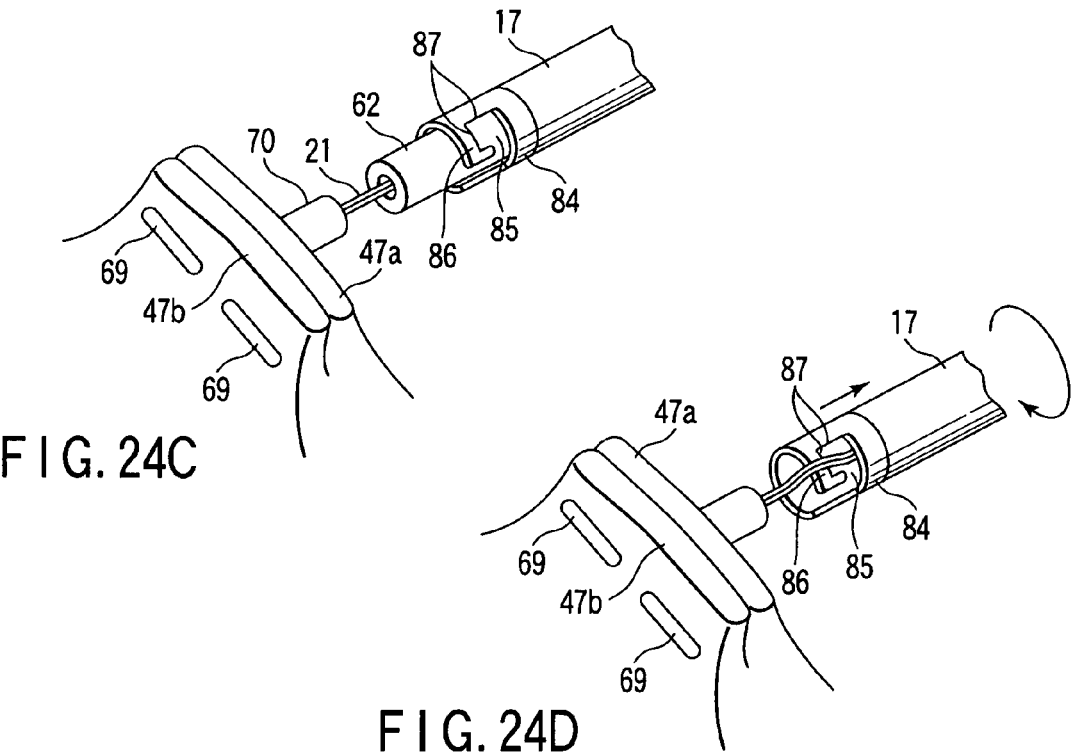
FIG. 24C
FIG. 24D

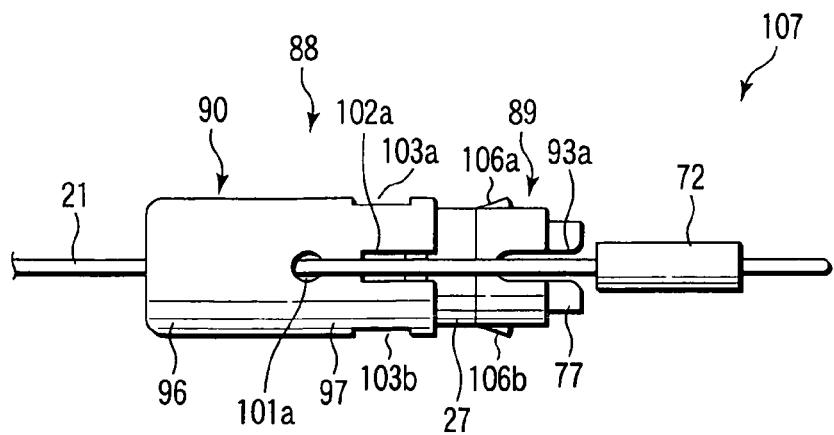
F I G. 25
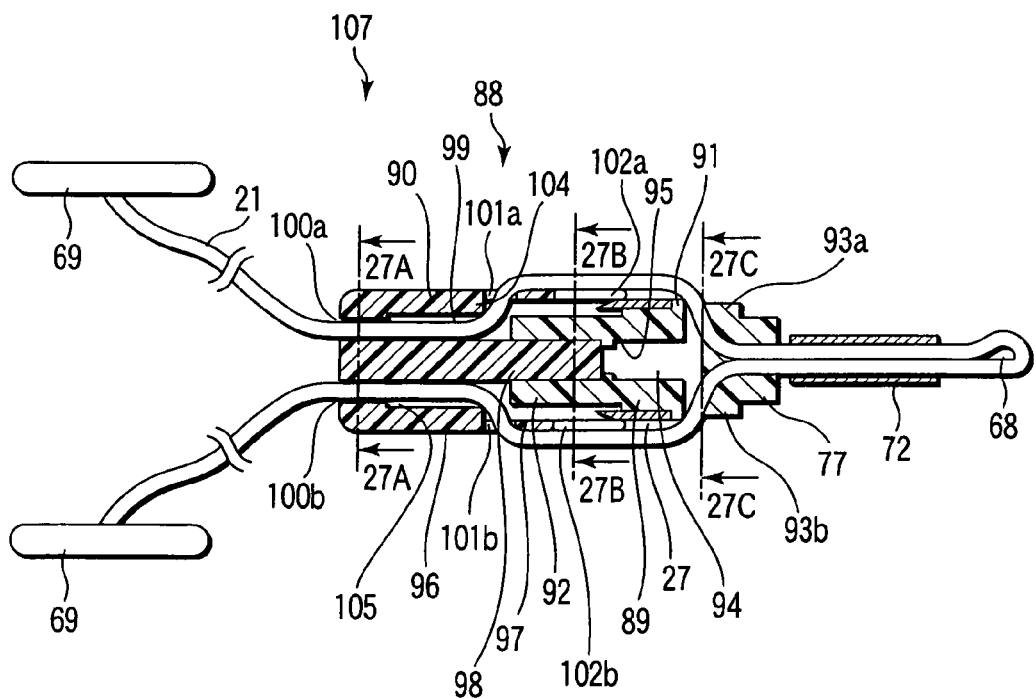
F I G. 26

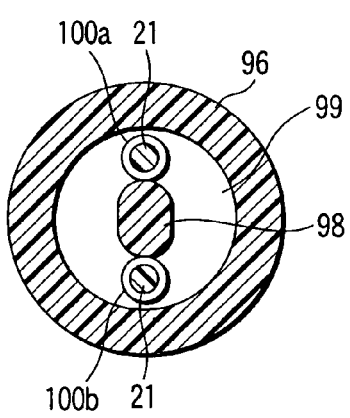
F I G. 27A
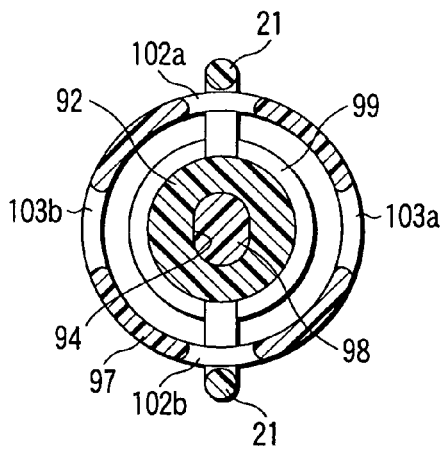
F I G. 27B
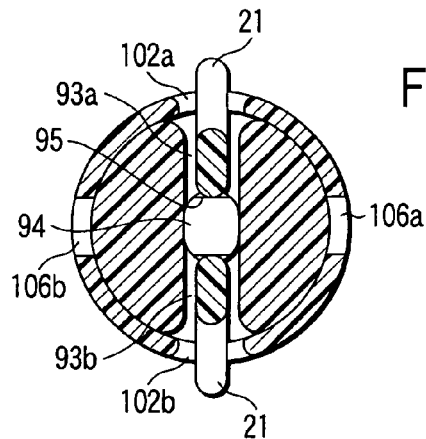
F I G. 27C
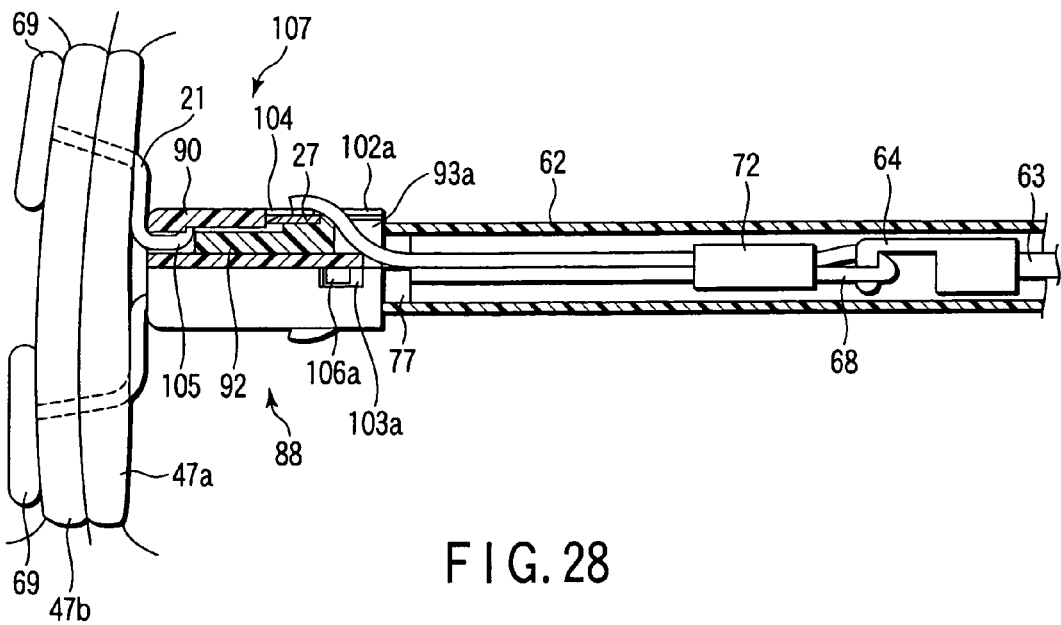
F I G. 28

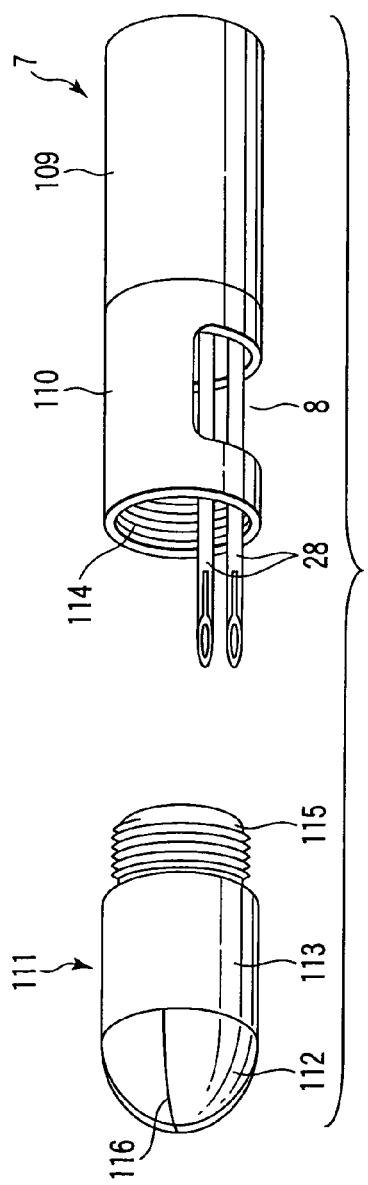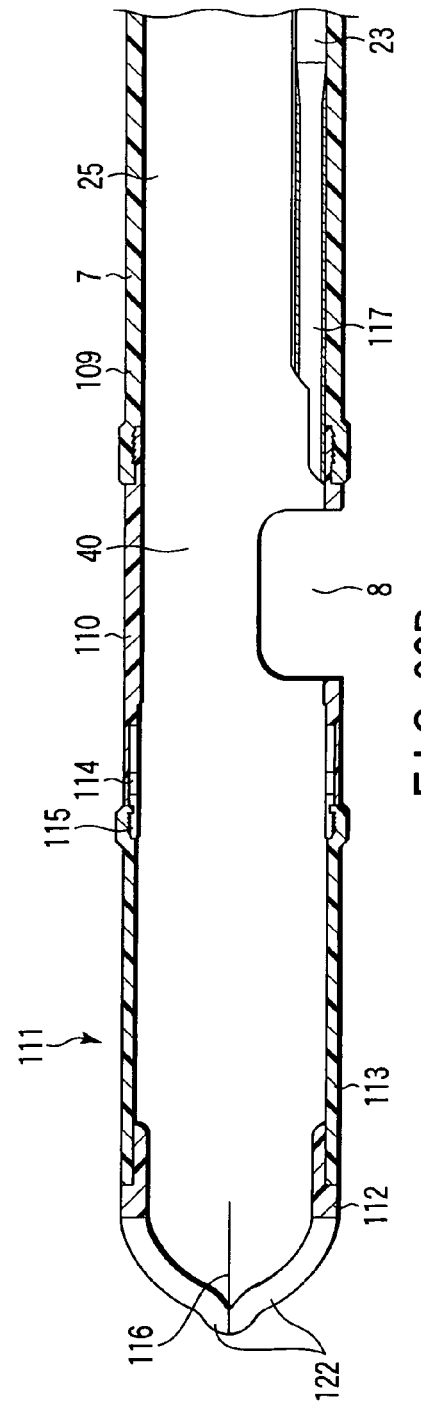
FIG. 30A
FIG. 30B

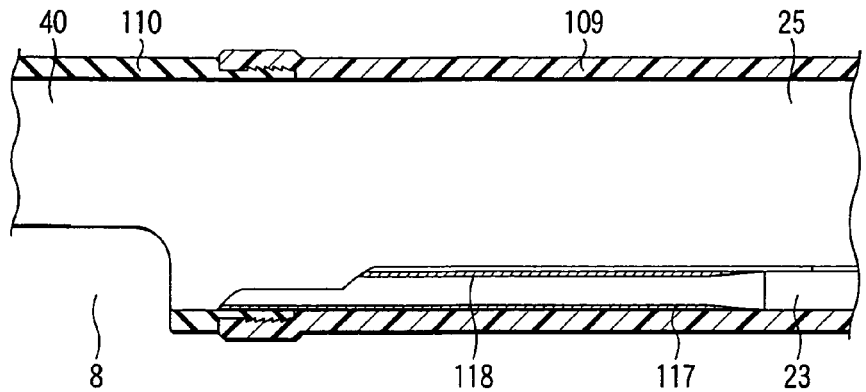
F I G. 31
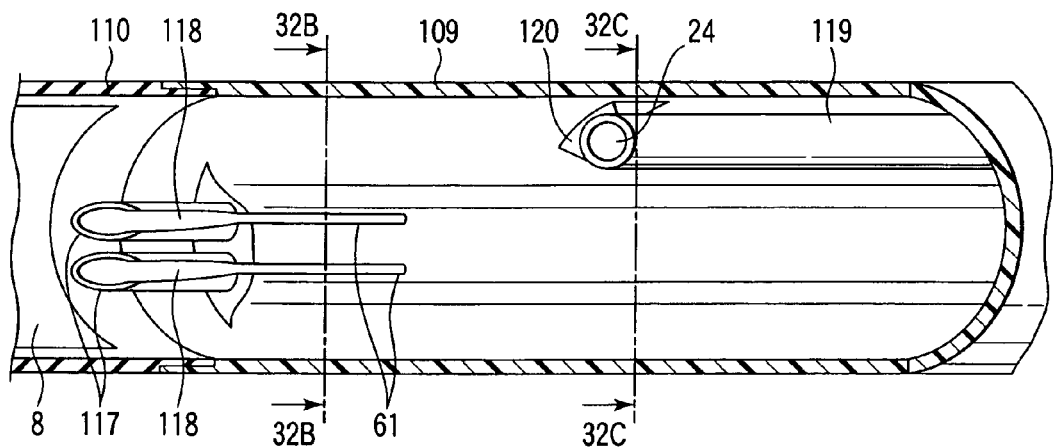
F I G. 32A
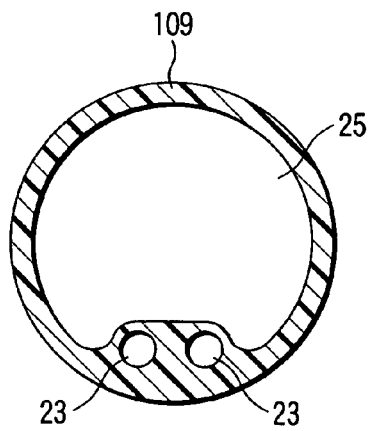
F I G. 32B
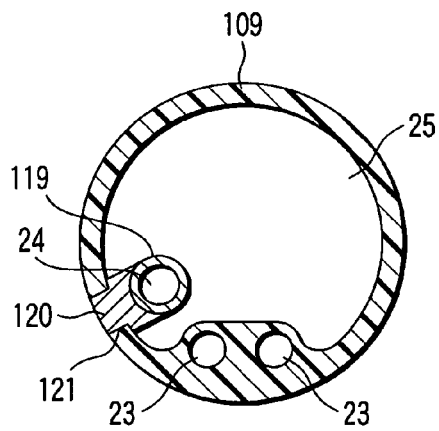
F I G. 32C

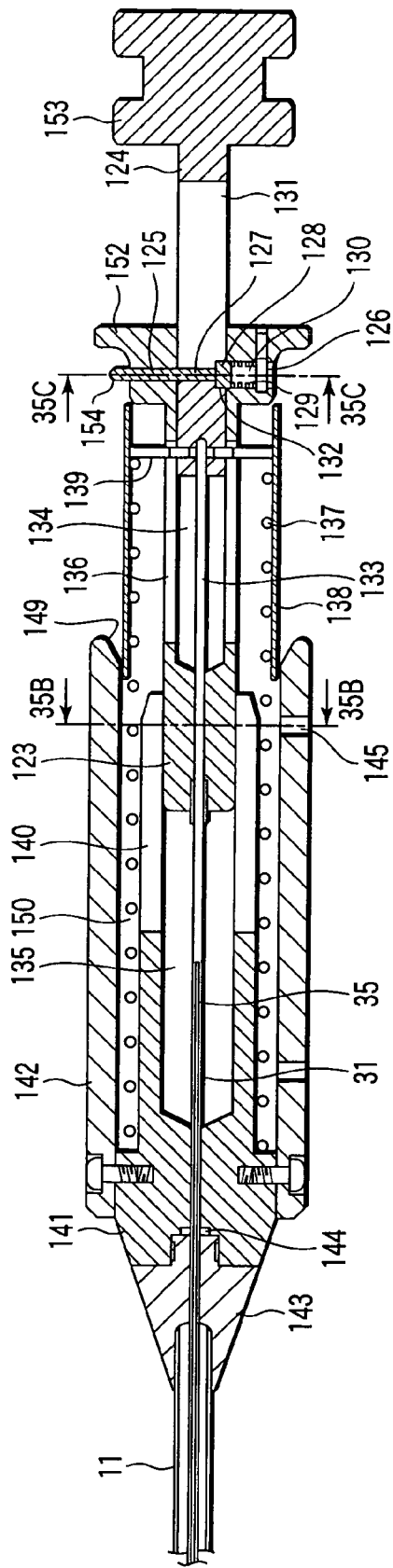
FIG. 35A
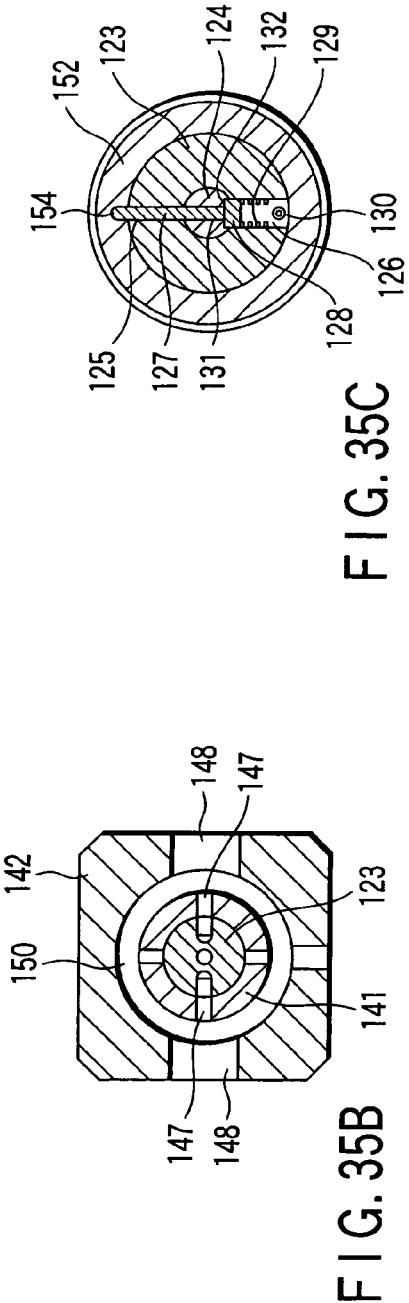
FIG. 35C
FIG. 35B

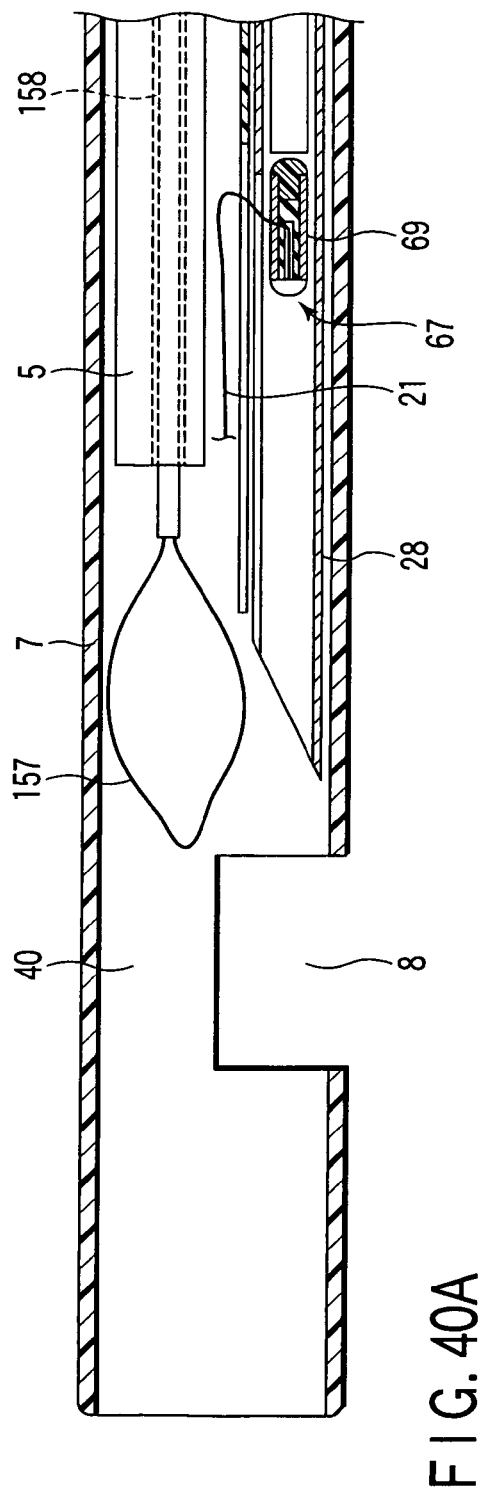
F I G. 40A
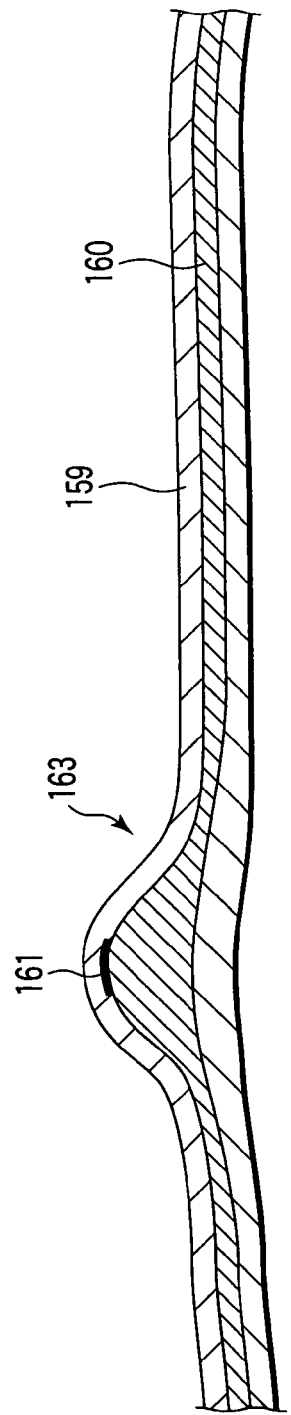
F I G. 40B

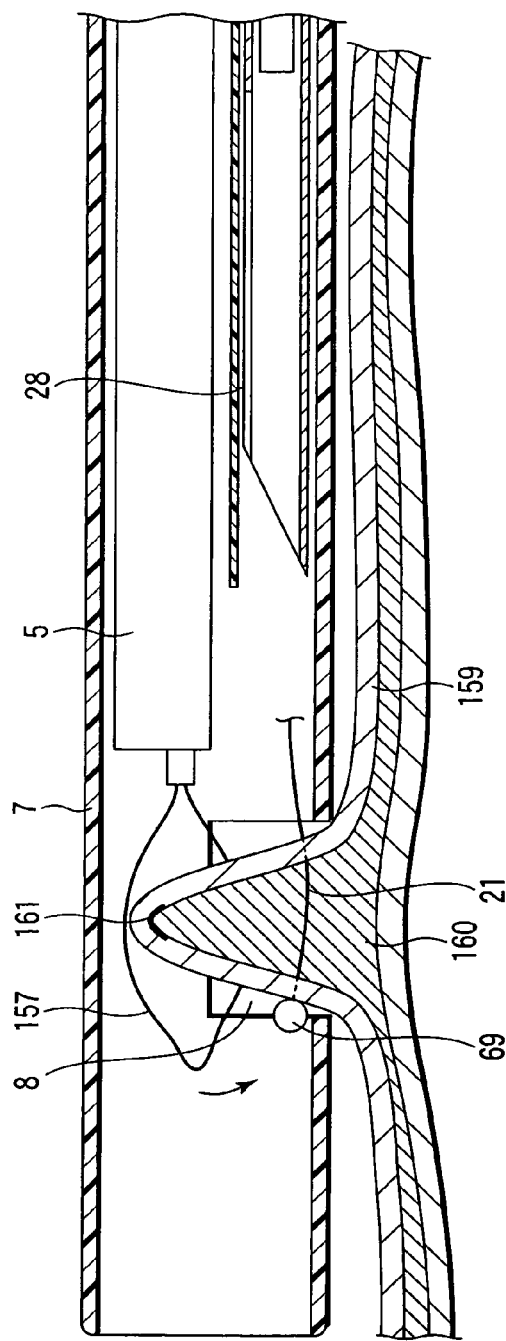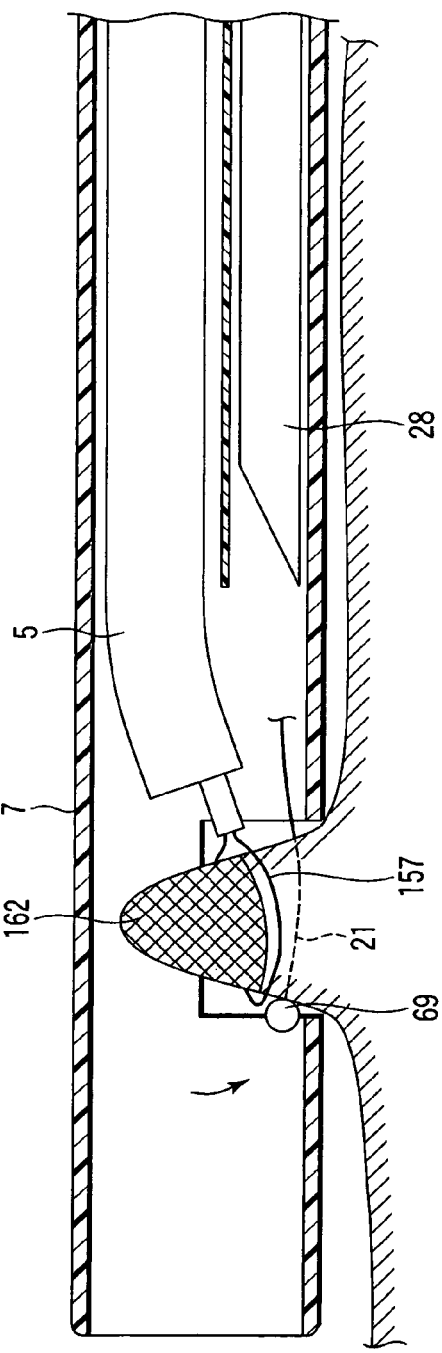
FIG. 41A
FIG. 41B

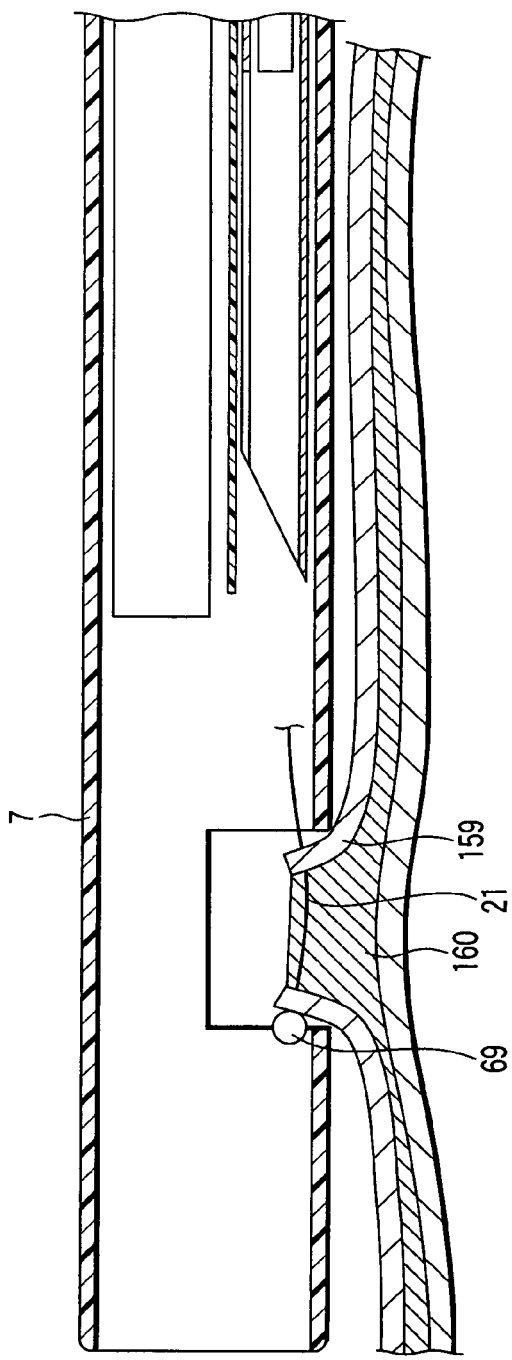
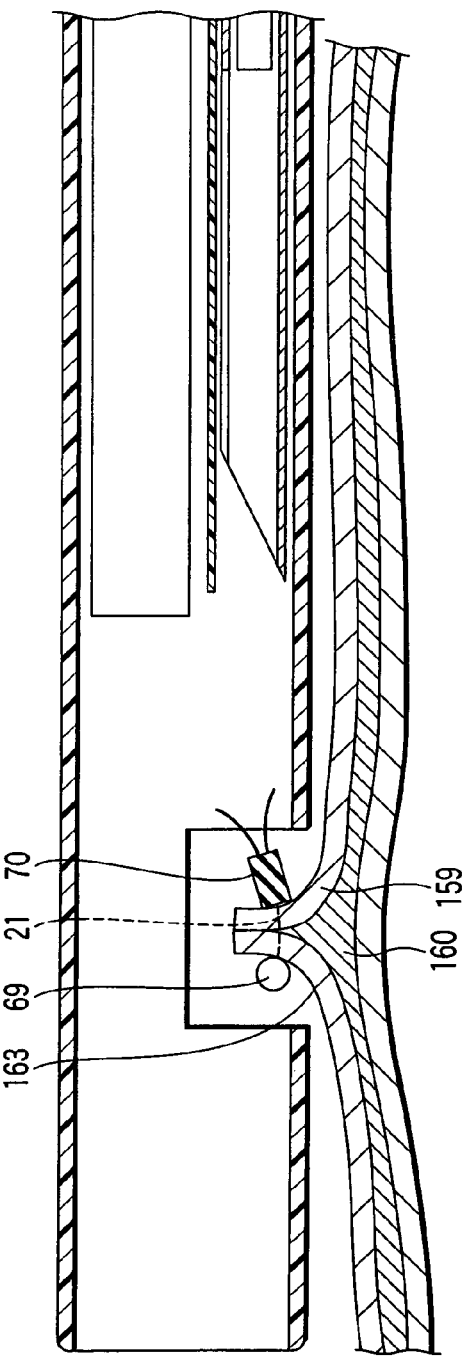
FIG. 42A
FIG. 42B

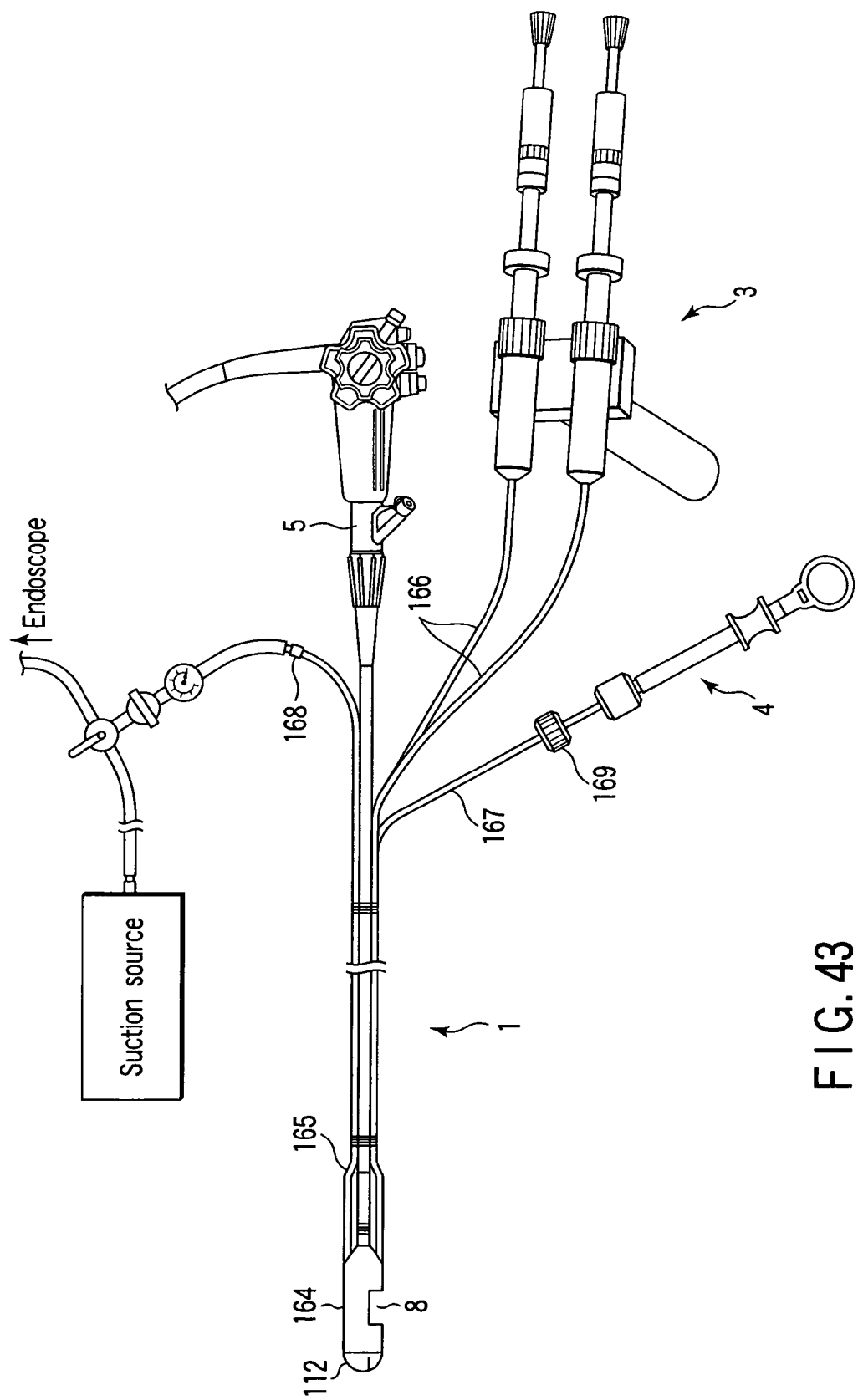
F I G. 43

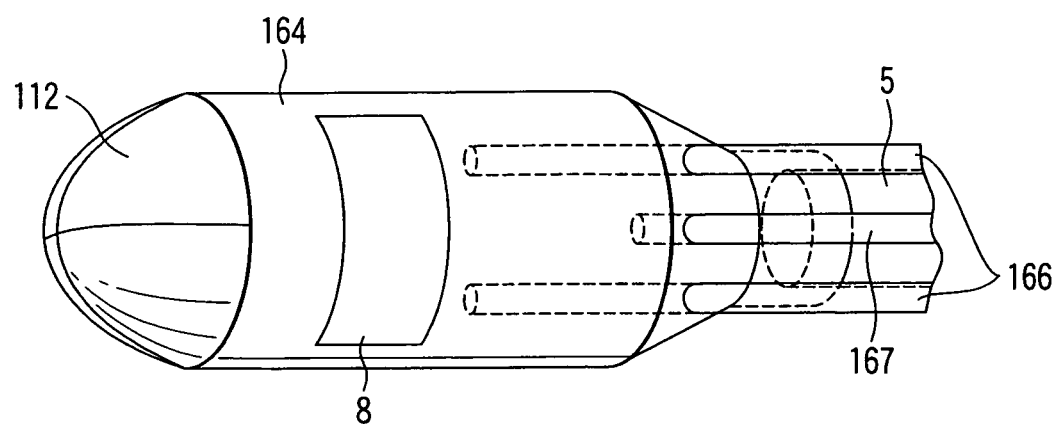
F I G. 44
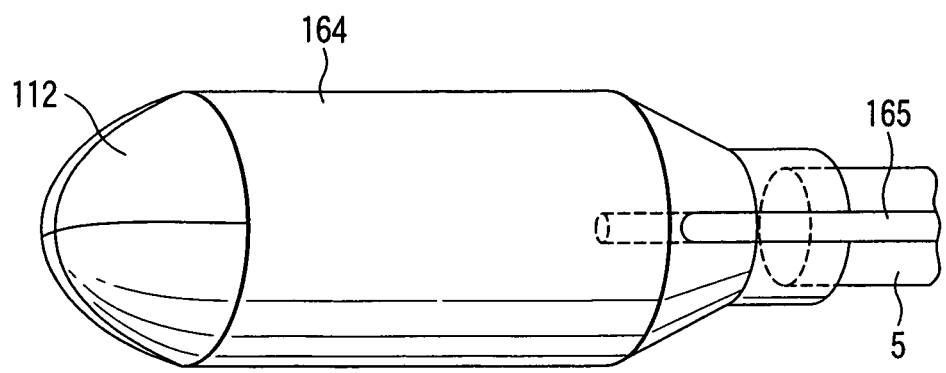
F I G. 45

APPARATUS FOR LIGATING/SUTURING LIVING TISSUES AND SYSTEM FOR RESECTING/SUTURING LIVING TISSUES

CROSS-REFERENCE TO RELATED APPLICATIONS

This application is a continuation application of U.S. application Ser. No. 10/430,071 filed May 6, 2003, now issued as U.S. Pat. No. 8,105,342, which claims the benefit of U.S. Provisional Application No. 60/378,548, filed May 8, 2002, each of which is incorporated herein by reference.

BACKGROUND OF THE INVENTION

The present invention relates to an apparatus for ligating/suturing living tissues and a system for resecting/suturing living tissues, for carrying out endoscopic repair such as resecting/suturing or ligating or suturing living tissues in the patient's body in combination with an endoscope. More particularly, the present invention relates to a repair system for carrying out the following repairs in a digestive tract including:

suturing for repair of a damaged site of tissues or reliable hemostasis of a bleeding part;

forming an artificial valve depending on tissues for Gastroesphageal Reflux Disease (GERD); and resecting a lesion that exists in an organ wall such as mucous membrane having a surface existing lesion part or sub-mucous tumor.

Currently, in the case of carrying out repair of a diseased site of living tissues in a patient's body, suturing for the purpose of reliable hemostatis of a bleeding part, these repairs and anastomosis are generally carried out by surgical operation.

However, in the case of surgical operation, of course, it is required to dissect the patient's body, and patient invasion is significant. In addition, postoperative hospitalization is required, and a burden on the patient on the aspect of cost such as hospitalization cost is significant. In such a circumstance, it is desirable to establish repair using lowly invasive peroral endoscope in which there is no need to dissect the patient's body.

In addition, the Gastroesophaseal Reflux Disease (GERD) is one of the diseases whose number of patients is likely to increase. Main diseases include heartburn and esophageal mucosal break. Although it is a benign disease, the patient's pain is significant. Thus, this disease is characterized in that a very large number of patients who require repair. This disease is primarily caused by degradation of a function of Lower Esophageal Sphincter (LES) that exists at the esophageal lower part and gastric acid reflux into an esophagus.

In the repair of the GERD, administration of gastric secretion inhibitor such as proton-pump inhibitors or the like is primarily carried out. If the GERD is light, the diseases is improved, and the radical cure of the cause of this disease can be expected. However, a repair effect with medication is small in a case where the function of the LES is significantly degraded, or alternatively, in a case of severe diseases with anatomic problems such as Hiatal Hernia. In addition, there is a problem that higher cost is indispensable because continuous administration is required. Therefore, in the severe GERD, surgical operation is applied.

As effective operation techniques, Nissen fundoplication and Toupet techniques or the like are widely carried out. In any of these techniques, the LES part is wrapped at a gastric wall, whereby functional improvement of the LES is carried out, and high repair effect is attained. Recently, laparoscopic technique is established, thus enabling more lowly invasive repair.

However, because the number of patients is very large and the above disease is a benign disease unlike cancers, it is desirable to establish a repairing technique using a much lower invasive and peroral endoscope. As one of such operation techniques, there is designed a method of ligating living tissues and inflating the tissues, and forming an artificial valve, thereby preventing reflow of gastric acid.

In addition, there is known a method of resecting a mucous membrane or sub-mucous tumor in a body cavity in a peroral and endoscopic manner. In this method, a high frequency resecting device and a grasping forceps are used in combination with an endoscope. Then, a liquid such as physiological saline is locally charged into a sub-mucous layer, and then, living tissues are pulled by the grasping forceps. Subsequently, the pulled up living tissues are resected by the high frequency resecting device in accordance with a predetermined procedure.

There is a possibility that bleeding occurs at a part at which a mucous membrane or sub-mucous layer is resected immediately after resection, or alternatively, after an elapse of time after operation. Thus, currently, a resected portion is clipped by using an endoscopic clipping device or the like after resection, whereby preventive hemostasis is carried out.

In addition, if the resected portion is kept as is, an ulcer or the like occurs. Because of this, the following method is used in order to prevent the occurrence of such an ulcer or the like or repair it at an earlier stage. Here, the peripheral mucous membrane of the resected portion is pulled onto the resected portion, and the pulled part is fixed by using the clipping device so as to protect the resected portion.

However, where the mucous membrane, sub-mucous layer or the like is resected in a wide range, it is required to carry out a plurality of clipping manipulations. Because of this, there is a problem that the operation technique is very complicated, and the treatment time is extended. Moreover, in this treatment, it is required to replace a high frequency treatment device or grasping forceps and a clipping device with an endoscope channel. In this respect as well, the operation technique is complicated, and the treatment time is extended.

Thus, it is desirable to develop a method of resecting living tissues, thereby making it possible to easily suturing the resected site. As a device for suturing living tissues in a patient's body in a peroral, endoscopic manner, for example, there is proposed a device "a" (refer to FIG. 46A to FIG. 47B) that can be mounted on an endoscope as disclosed in U.S. Pat. No. 5,792,153.

As shown in FIG. 46A, a suction cavity "c" is provided at a distal end section of this device "a". A tube "b" is inserted into this cavity "c". This tube "b" can be connected to a suction source.

Further, a hollow needle "d" inserted into the endoscope's forceps channel is provided at the device "a". A pipe shaped thread carrier "g" can be mounted in this needle "d". This thread carrier "g" has an internal cavity and side holes "e" and "f". A wire "i" is retractably inserted into the needle "d". A valve "h" is provided at the wire "i". This valve "h" can be removably engaged with the side hole "e" of the thread carrier "g".

In addition, a thread "j" is connected to the thread carrier "g". A trapping member "k" is provided at a distal end side of the cavity "c". This trapping member "k" is removably engaged with the side hole "f" of the thread carrier "g".

When this device "a" is used, the thread carrier "g" is mounted in the needle "d" while the valve "h" is engaged with the side hole "e" in advance.

Next, the endoscope having the device "a" mounted thereon is inserted into the patient's body in a peroral manner. After the endoscope has been inserted, living tissue "m1" to be sutured as shown in FIG. 46A is suctioned into the cavity "c".

Then, the needle "d" is pushed out from the endoscope, and the living tissue "m1" is punctured by this needle "d", as shown in FIG. 46B.

Next, the wire "i" is advanced, and the thread carrier "g" is pressed forwardly from the needle "d". Then, the side hole "f" of the thread carrier "g" and the trapping member "k" are engaged with each other.

Then, the valve "h" is removed from the side hole "e". In this state, as shown in FIG. 46C, the wire "i" and the needle "d" are retracted into the endoscope. At this time, the thread "j" of the thread carrier "g" is sutured around the living tissue "m1". Subsequently, suction of the cavity "c" is released. In this manner, the living tissue "m1" slips off from the cavity "c". Then, a first manipulation for suturing the thread "j" of the thread carrier "g" around the living tissue "m1" terminates.

Next, another part (living tissue "m2") of the living tissue "m1" is suctioned into the cavity "c" again. In this state, as shown in FIG. 47A, the living tissue m2 is punctured by the needle "d".

Subsequently, the wire "i" is advanced, thereby causing the valve "h" to be engaged with the side hole "e". Then, the trapping member "k" is released from the side hole "f". In this state, the valve "h", the thread carrier "g", and the needle "d" are retracted to the proximal end side. At this time, the thread "j" is sutured around the living tissue "m2". Subsequently, suction of the cavity "c" is released. In this manner, as shown in FIG. 47B, the living tissue "m2" slips off from the cavity "c". Then, a second manipulation for suturing the thread "j" around the living tissue "m2" terminates.

Further, the above step of suturing the thread "j" around the living tissue "m" is repeated in its required number. Then, after a work of suturing the thread "j" around the living tissue "m" in its required number has terminated, the device "a" is removed from the inside of the body to the outside together with the endoscope. Finally, both ends of the thread "j" pulled out to the outside of the body are knotted and fixed, thereby terminating suturing.

However, the following problem occur in the case of the device "a" having its constitution disclosed in U.S. Pat. No. 5,792,153. That is, after the thread "j" has punctured into the living tissue "m", means for ligating the thread "j" is not provided at the device "a" itself. Thus, a work of knotting both ends of the thread "j" at the outside of the patient's body, and then, delivering the knot into the patient's body is required. As a result, the operation technique of suturing the living tissues in the patient's body is complicated, and the treatment time is extended as well.

In addition, in the case of carrying out a plurality of stitch manipulations as well, a distance between stitches cannot be controlled reliably. Thus, it is difficult to reliably carry out suturing in a small number of stitch manipulations.

Two manipulations, i.e., one engaging manipulation between the valve "h" and the side hole "e" or between the trapping member "k" and the side hole "f" and the other disengaging manipulation are required every time the needle "d" is operated to be punctured. Thus, manipulation of the device "a" is very complicated, and the treatment time is extended.

In addition, the range that can be punctured in one puncturing manipulation of the needle "d" is determined depending on the size of the cavity "c". However, considering a burden on the patient when the device "a" is inserted into the patient's body, the external diameter of the entire device "a" is dimensionally limited itself, and the external diameter of the entire device "a" is not increased dimensionally. Then, in this constitution, the endoscope and the cavity "c" are disposed at their displaced position. Thus, there is a problem that the size of the cavity "c" is reduced. In the case where the suture range of the living tissue "m" is wider than that when absorbed into the cavity "c" by suction, its suturing is impossible, and its application is limited.

In addition, in International Patent Application Publication WO99/22649, there is disclosed a device "n" for forming inflation of the living tissues in order to repair the peroral gastroesophageal reflux disease (refer to FIG. 48 to FIG. 49D).

This device "n" has a movable arm "p" that is turnable at a distal end of a flexible tube "o". Further, a female fastener "r" is selectively mounted on the movable arm "p", and a male fastener "q" is selectively mounted on the flexible tube "o" that can be connected when this movable arm "p" is turned, respectively.

Similarly, turnable grip means "s" and an endoscope insertion opening "u" are provided at a distal end of the flexible tube "o". An endoscope "t" can be inserted into the opening "u" of this flexible tube "o". This endoscope "t" is inserted over the full length of the flexible tube "o".

Then, the following manipulation is carried out when this device "n" is used. First, as shown in FIG. 49A, the flexible tube "o" is inserted into the patient's stomach in a peroral manner. Subsequently, the grip means "s" is abutted against an esophagogastric junction "v".

At this time, the grip means "s" is manipulated, and the esophagogastric junction "v" is gripped as shown in FIG. 49B. Subsequently, the flexible tube "o" is advanced to the anal side, and the esophagogastric junction "v" is pulled down.

Here, as shown in FIG. 49C, the movable arm "p" is manipulated to be turned. At this time, as shown in FIG. 49D, the esophagogastric junction "v" gripped by the grip means "s" is punctured through the male fastener "q", and is engaged with the female fastener "r" as is.

The esophagogastric junction "v" gripped by the above manipulation is reduced in length, its intermediate portion is reduced and pushed out inwardly, and a rise "x" is formed. At this time, in the device "n" of the above International Patent Application Publication WO99/22649, a positional relationship between the grip means "s" and the male fastener "q" or female fastener "e" is fixed. Thus, the size of the rise "x" is uniquely determined.

In general, in surgical operation (Nissen fundoplication), a food passing problem (disphagia) is reported as a complication of artificial cardia. In this operation technique for repair of gastroesophageal reflux disease as well, there is a danger that a similar problem occurs with a large rise "x". Therefore, in the case of a light disease, the degree of the rise "x" is reduced, whereby it is preferable that priority be assigned to food passing. In this way, in the repair of a gastroesophageal reflux disease, it is advantageous that the rises "x" of various sizes can be formed according to the degree of the diseases.

However, in the device "n" of the above International Patent Application Publication WO99/22649, the size of the rise "x" is uniquely determined, thus making it difficult to have flexibility in the course of repairing the gastroesophageal reflux disease.

In addition, the female fastener "q" is exposed to the external surface of the device, and thus, there is a possibility that the female fastener "q" comes into contact with the body wall when this device is inserted into the body cavity.

BRIEF SUMMARY OF THE INVENTION

The present invention has been made in view of the foregoing circumstance. It is a first object of the present invention to provide a suturing device capable of reliably ligating or suturing tissues in the patient's body relevant to a patient in a lower invasive manner.

It is a second object of the present invention to provide a resecting/suturing system capable of reliably suturing a resection site by resecting tissues in the patient's body relevant to the patient in a lower invasive manner.

It is a third object of the present invention to provide a resecting/suturing system capable of arbitrarily adjusting a resection depth or resection range of tissues in the patient's body.

It is a fourth object of the present invention to provide a suturing device and system for resecting/suturing living tissues with its simple treatment/manipulation and treatment time.

It is a fifth object of the present invention to provide a suturing device and system for resecting/suturing living tissues in which the range capable of suturing tissues in the patient's body is maximally wide.

It is a sixth object of the present invention to provide a suturing device and system for resecting/suturing living tissues in which the patient has little pain when the device is inserted into the patient's body.

In this device, the living tissues in the patient's body can be ligated and sutured in combination with an endoscope, and thus, more lowly invasive repair can be carried out for the patient. As a result, the hospitalization period can be reduced, thus, making it possible to reduce a burden on the patient in an aspect of cost such as hospitalization cost.

In this device, there is provided means for puncturing a ligating member into the living tissues, followed by ligating the ligating member. Thus, there is no need to temporarily remove the device from the inside to the outside of the body and to carry out ligation outside of the body. Therefore, the treatment/manipulation is very simplified, and the treatment time is significantly reduced. Further, means for cutting a redundant portion of the ligating member after ligation is provided as well. Thus, there is no need to insert another cutting device into the patient's body again. In this respect as well, the treatment/manipulation can be simplified, and the treatment time can be reduced.

In the case where the living tissues in the patient's body is resected as well, it is possible to suture the resected portion immediately without replacement with another treatment device after resection. Thus, prevention of bleeding from the resected portion or earlier repair of an ulcer that occurs with the resected portion can be carried out for the patent lowly invasively and easily.

When the resected portion or damaged portion of the living tissues is sutured, the entire living tissues targeted to be sutured is suctioned into a chamber by means of suctioning operation, and then, the ligating member is punctured. Thus, it is possible to easily suture a region in a wide range, as compared with a case in which an attempt is made to carrying out suturing by using a clipping device or the like.

The quantity of living tissues to be suctioned from the side opening of this device can be adjusted by adjusting a suction pressure, and thus, the depth or size of the living tissues to be resected can be adjusted easily and reliably. Even in the case where the living tissues are inflated and ligated, and an artificial valve is provided for the purpose of treatment of endoscopic gastroesophageal reflux diseases, the size of such inflation can be arbitrarily adjusted, thus making it possible to form an artificial valve of size according to the degree of diseases.

The living tissues are suctioned into a chamber frontally positioned to be substantially coaxial to the endoscope, thus making it possible to easily and reliably check whether or not a puncture member can be well punctured into a target site of the living tissues before puncturing the puncture member. Further, in the case where the chamber is formed of a flexible sheath having an internal cavity in which the endoscope can be inserted, the distal end of the endoscope is moved forwardly or backwardly relevant to the side opening or is manipulated to be bent, thereby making it possible to adjust the sutured tissues in an easily observable state. As a result, fine control of the puncture position is possible, and reliable ligation or suturing can be carried out. Further, treatment/manipulation is simplified, and the treatment time is significantly reduced.

When the puncture members are disposed in parallel to each other with predetermined intervals, the puncture-in position and puncture-out point on the living tissues of the puncture member are also defined with desired predetermined intervals. As a result, the stitch intervals can be reliably controlled without extremely reducing the intervals. As a result, treatment/manipulation is simplified, and the treatment time is significantly reduced. Even in the case where it is required to carry out stitching a plurality of times, a distance of one stitch can be controlled constantly, and suturing can be carried out reliably with a small number of stitching manipulations.

The endoscope and chamber into which the living tissues are suctioned are disposed in a substantially coaxial manner. Thus, a larger space in which the living tissues can be suctioned can be obtained without increasing the outer diameter of the entire system including the endoscope. As a result, a pain on the patient during system insertion can be reduced. The puncture member is housed in this device, thus making it possible to insert the device into the patient's body without damaging the internal cavity.

In the case where a chamber for suctioning the living tissues is mounted on the distal end of the endoscope, an element other than such chamber is composed of a sheath of the endoscope itself. Thus, the small outer diameter and excellent flexibility are achieved, thus making it easy to insert the entire system into the patient's body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a perspective cross section showing a part of a distal end of the over-tube in the suturing apparatus according to the first embodiment;

FIG. 2B is a perspective view showing an appearance of a needle distal end in the suturing apparatus according to the first embodiment;

FIG. 2C is a perspective view showing an appearance of a ligating unit in the suturing apparatus according to the first embodiment;

FIG. 5A is a longitudinal cross section showing an internal constitution of a needle lumen of the over-tube in the suturing apparatus according to the first embodiment;

FIG. 5B is a longitudinal cross section showing an internal constitution of a cutter sheath in the over-tube in the suturing apparatus according to the first embodiment;

FIG. 7A is a longitudinal cross section showing a state in which a pusher slider and a needle slider of the over-tube in the suturing apparatus according to the first embodiment are pulled out to the proximal end side, and is removed from ruptured tissues;

FIG. 7B is a longitudinal cross section showing a state in which a knot is advanced to the distal end side at a distal end of the pusher tube in the over-tube in the suturing apparatus according to the first embodiment;

FIG. 8A is a longitudinal cross section showing a state in which a knot is abutted against living tissues in the over-tube in the suturing apparatus according to the first embodiment;

FIG. 8B is a longitudinal cross section showing a state in which sutured living tissues are removed from the side opening of the over-tube in the suturing apparatus according to the first embodiment;

FIG. 9 is a longitudinal cross section showing a state in which a thread at a proximal end of a knot of living tissues sutured by the suturing apparatus according to the first embodiment is cut;

FIG. 10 is a longitudinal cross section showing a state in which the side opening of the over-tube in the suturing apparatus according to the first embodiment is positioned on an esophageal wall immediately above a cardiac part of stomach;

FIG. 11 is a longitudinal cross section showing a state in which a needle member is punctured into tissues suctioned into the treatment lumen through the side opening of the over-tube in the suturing apparatus according to the first embodiment;

FIG. 12 is a longitudinal cross section showing a state in which an artificial valve is formed at the cardiac part of stomach by the suturing apparatus according to the first embodiment;

FIG. 13 is a perspective view showing a modified example of the over-tube in the suturing apparatus according to the first embodiment;

FIG. 14 is a perspective view showing an appearance of an entire suturing apparatus according to a second embodiment of the present invention;

FIG. 15A is a perspective cross section showing a part of a distal end of an over-tube in the suturing apparatus according to the second embodiment;

FIG. 15B is a side cross section showing a part of a ligating device in the suturing apparatus according to the second embodiment;

FIG. 18A is a perspective cross section showing a part of the distal end of the over-tube when the ligating unit is attached to the ligating device in the suturing apparatus according to the second embodiment;

FIG. 18B is a longitudinal cross section showing an internal constitution of a needle lumen of the over-tube in the suturing apparatus according to the second embodiment;

FIG. 19A is a longitudinal cross section of essential portions showing a state in which a loop section of the ligating unit is hooked by a hook of a manipulating wire in a ligating sheath in the suturing apparatus according to the second embodiment;

FIG. 19B is a longitudinal cross section of essential portions, showing a hook pulled toward the proximal end, thus suturing the living tissue, in the suturing apparatus according to the second embodiment gently abuts against a distal end of the ligating sheath;

FIG. 19C is a longitudinal cross section of essential portions showing a state in which a thread is cut by a cutter in the suturing apparatus according to the second embodiment;

FIG. 22 is a perspective view showing a ligating unit according to a second modified example of the second embodiment;

FIG. 23 is a longitudinal cross section showing a ligating unit according to a third modified example of the second embodiment;

FIG. 24A is a longitudinal cross section showing a state in which a ligating device and a ligating unit are mounted in a suturing apparatus according to a third embodiment of the present invention;

FIG. 24B is a perspective view showing a distal end section of a cutter sheath in the suturing apparatus according to the third embodiment;

FIG. 24C is a perspective view illustrating a state in which living tissues are ligated by a ligating unit in the suturing apparatus according to the third embodiment;

FIG. 24D is a perspective view illustrating working when a thread of the ligating unit in the suturing apparatus according to the third embodiment is cut;

FIG. 25 is a side view showing a ligating unit in a suturing apparatus according to a fourth embodiment of the present invention;

FIG. 26 is a longitudinal cross section showing a ligating unit in the suturing apparatus according to the fourth embodiment;

FIG. 27A is a sectional view taken along the line 27A-27A of FIG. 26;

FIG. 27B is a sectional view taken along the line 27B-27B of FIG. 26;

FIG. 27C is a sectional view taken along the line 27C-27C of FIG. 26;

FIG. 28 is a longitudinal cross section showing a ligating unit and a ligating device after living tissues have been ligated;

FIG. 30A is an exploded perspective view showing an appearance of a distal end section of an over-tube in a suturing apparatus according to a sixth embodiment of the present invention;

FIG. 30B is a longitudinal cross section showing the distal end section of the over-tube in the suturing apparatus according to the sixth embodiment;

FIG. 31 is a longitudinal cross section showing the distal end section of the over-tube in the suturing apparatus according to the sixth embodiment;

FIG. 32A is a perspective cross section showing the distal end section of the over-tube in the suturing apparatus according to the sixth embodiment;

FIG. 32B is a sectional view taken along the line 32B-32B of FIG. 32A;

FIG. 32C is a sectional view taken along the line 32C-32C of FIG. 32A;

FIG. 35A is a sectional view taken along line 35A-35A in FIG. 34;

FIG. 35B is a sectional view taken along the line 35B-35B of FIG. 35A;

FIG. 35C is a sectional view taken along the line 35C-35C of FIG. 35A;

FIG. 40A is a longitudinal cross section showing a distal end section of an over-tube in the resecting/suturing system according to the seventh embodiment;

FIG. 40B is a longitudinal cross section of essential portions showing a state in which a local injection liquid has been injected into living tissues by the resecting/suturing system according to the seventh embodiment;

FIG. 41A is a longitudinal cross section of essential portions showing a state a ligating unit has been punctured into living tissues by the resecting/suturing system according to the seventh embodiment;

FIG. 41B is a view illustrating a state before resecting living tissues by the resecting/suturing system according to the seventh embodiment;

FIG. 42A is a view illustrating a state after resecting living tissues by the resecting/suturing system according to the seventh embodiment;

FIG. 42B is a longitudinal cross section of essential portions showing a state after ligating living tissues by the resecting/suturing system according to the seventh embodiment;

FIG. 43 is a perspective view showing an appearance of an entire suturing apparatus according to an eighth embodiment of the present invention;

FIG. 44 is a perspective view showing a connection state of two needle tubes and ligating tube at a proximal end side of a chamber in the suturing apparatus according to the eighth embodiment;

FIG. 45 is a perspective view showing a connection state of a suction tube at the proximal end side of the chamber in the suturing apparatus according to the eighth embodiment;

DETAILED DESCRIPTION OF THE INVENTION

Figures 1A, 1B:
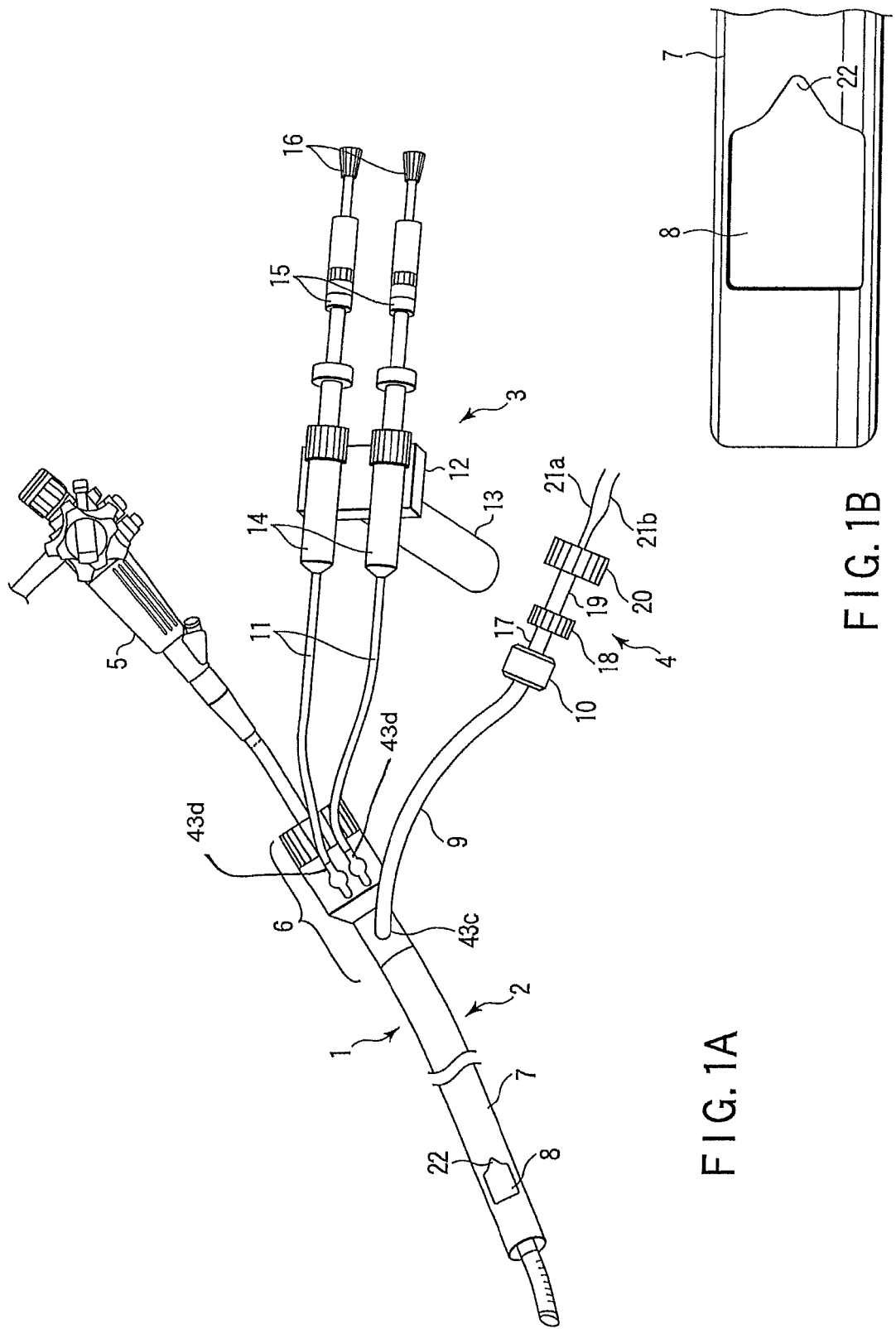
FIG. 1A is a perspective view showing an appearance of an entire suturing apparatus according to a first embodiment of the present invention.
FIG. 1B is a plan view showing a distal end of an over-tube.

Hereinafter, a first embodiment of the present invention will be described with reference to FIG. 1A to FIG. 12. FIG. 1 shows an appearance of an entire suturing apparatus 1 according to the present embodiment. This suturing apparatus 1 comprises an over-tube 2, a needle manipulating section 3, a ligating device 4, a needle 28 (refer to FIG. 2A), and a ligating unit 38 (refer to FIG. 2C).

An elongated sheath section 7 is provided at the over-tube 2. This sheath section 7 is set to about 0.3 m to 2 m, for example, and preferably set to about 1 m. As shown in FIG. 1B, a side opening 8 is formed at a distal end section of the sheath section 7. Further, a connecting section 6 is arranged at a proximal end section of the sheath section 7.

Figure 3:
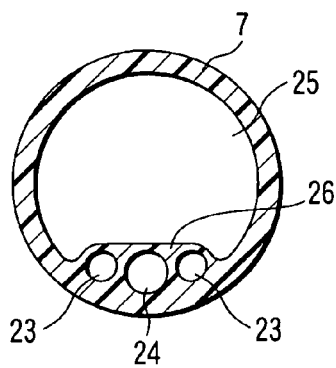
FIG. 3 is a transverse cross section showing the over-tube in the suturing apparatus according to the first embodiment.

Further, as shown in FIG. 3, the sheath section 7 is formed of a multi-lumen tube, i.e., in this embodiment, a four-lumen tube comprising four lumens (one endoscope lumen 25, two needle lumens 23, and one ligating lumen 24). Then, the two needle lumens 23, the ligating lumen 24, and the endoscope lumen 25 are formed to be surrounded by a partition wall 26 respectively, and is formed integrally with the over-tube 2.

In addition, an endoscope 5 can be slidably inserted into the endoscope lumen 25. A needle 28 can be slidably inserted into the two needle lumens 23. A ligating device 4 described later can be slidably inserted into the ligating lumen 24.

Further, the sheath section 7 is formed of a material having flexibility so that the sheath section 7 can be deformed in accordance with bending of the endoscope 5. The sheath section 7 is formed of a plastic material which is comparatively flexible and which has excellent transparency such as polyurethane, vinyl chloride, polyurethane elastomer, polystyrene elastomer, or polyolefin elastomer, for example. When the endoscope 5 has been inserted into the endoscope lumen 25, the outside of the sheath section 7 can be observed through a wall section of the sheath section 7 through the endoscope 5 in the endoscope lumen 25. It is preferable that the sheath section 7 is entirely transparent. However, the sheath section 7 may be transparent within the range of at least about 5 cm before and after the side opening 8, and the other portion may not be always transparent.

In addition, it is desirable that a distal end of the sheath section 7 is particularly flexible in order to be easily inserted into a patient's body. For example, the wall section at the distal end side of the sheath section 7 is defined to be smaller than a proximal end wall section in thickness, thereby making it possible to soften the distal end side of the sheath section 7. Further, the outer diameter of the sheath section 7 is of size such that the sheath section can be inserted into the patient's body. The outer diameter is set to about 10 mm to 25 mm, for example, or is preferably set to about 15 mm to 18 mm.

In addition, as shown in FIG. 2A, the distal end sections of the two needle lumens 23 and the ligating lumen 24 are disposed at a position retracted more proximally than the distal end position of the sheath section 7 by engraving a distal end section of the partition wall 26 of the sheath section 7. It is desirable that a distance between the distal end positions of the sheath section 7 and the needle lumen 23 is about 30 mm to 100 mm, for example. Further, the distal end position of the ligating lumen 24 is disposed at a position spaced more proximally than that of the needle lumen 23. It is desirable that a distance between the distal end positions of the ligating lumen 24 and the needle lumen 23 is set to about 100 mm, for example. One treatment lumen 40 is formed between the distal end positions of the sheath section 7 and the distal end section of the two needle lumens 23.

In addition, the inner diameter of the needle lumen 23 is set to a size such that the needle 28 and the threads 21a and 21b of the ligating unit 38 mounted on the needle tip can be inserted at the same time. Further, the inner diameter of the ligating lumen 24 may be set to a size such that the ligating device 4 described later can be inserted, and the inner diameter of the endoscope lumen 25 may be set to a size such that the endoscope 5 can be inserted. The ligating lumen 24 and the endoscope lumen 25 may be formed in any shape. However, it is desirable that the endoscope lumen 25 be as large as possible because the endoscope can be easily manipulated.

Other tubes are mounted on the inner periphery face side of an over-tube (one-lumen tube) having one internal cavity, whereby two needle lumens 23 and one ligating lumen 24 may be formed independent of the over-tube, respectively.

In addition, two needle lumens 23 extend in substantially parallel to each other. Further, an interval between the two needle lumens 23 is constant. An interval between distal end sections of the needle 28 inserted into the needle lumens 23 each is set so as to be constant within the range of 2 mm to 20 mm.

The side opening 8 on the outer periphery face of the sheath section 7 is disposed at the distal end side more than the distal end position of the needle lumen 23. Further, the center line of the side opening 8 is disposed at an intermediate position of the two needle lumens 23.

As shown in FIG. 1B, a substantially V shaped thread receiving section 22 at which its substantial center portion is recessed toward the proximal end side is formed at the proximal end section of the side opening 8 of the sheath section 7. This thread receiving section 22 may prevent the thread 21 from being displaced in a transverse direction when the thread 21 is hooked. For example, this thread receiving section 22 may be such that a substantial V shaped recess portion extends toward the proximal end side by about 1 mm or 2 mm.

Although it is desirable that the side opening 8 of the sheath section 7 is formed in a rectangular shape extending in the axial direction of the sheath section 7 at a section other than the thread receiving section 22, the side opening 8 may be formed in an elliptical or circular shape. In the case where the side opening 8 is formed in a rectangular shape, it is desirable that its corners are rounded. In this case, when living tissues are suctioned from the side opening 8 to the inside of the sheath section 7, a gap between the peripheral rim portion of the side opening 8 and the living tissues is hardly formed. Because of this, the living tissues are easily suctioned from the side opening 8 to the inside of the sheath section 7, which is desirable.

It is desirable that the side opening 8 is about 5 mm to 30 mm, for example, in length in the axial direction of the sheath section 7. In particular, it is desirable that the length is about 10 mm to 20 mm. Further, it is desirable that the width of the side opening 8 is about 3 mm to 23 mm, for example. In particular, it is desirable that the width is about 13 mm to 16 mm. In addition, it is desirable that a distance between the distal end of the needle lumen 23 and the thread receiving section 22 of the side opening 8 is about 5 mm, for example.

Figure 4A:
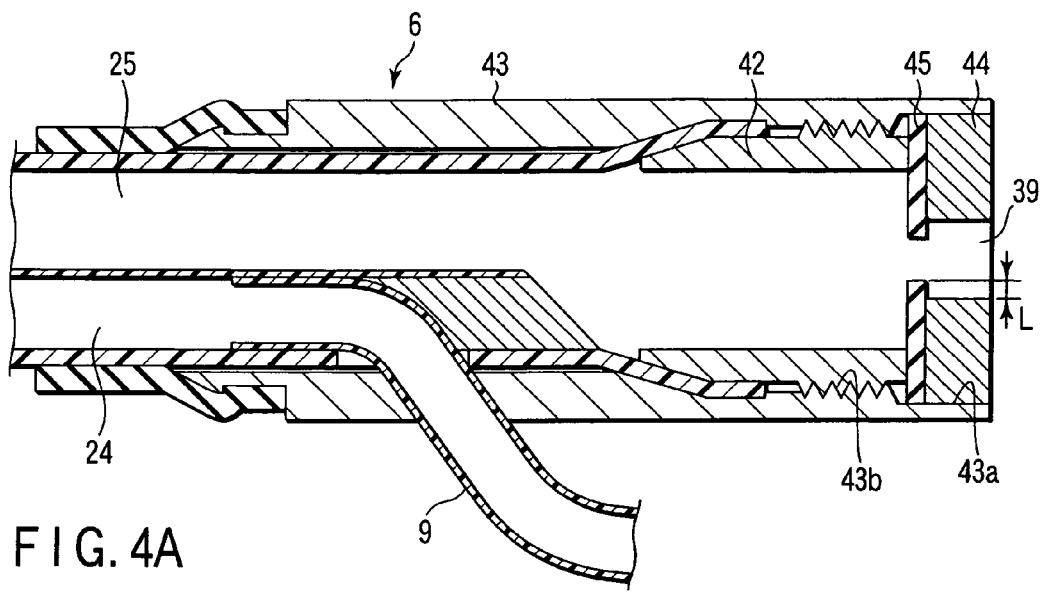
FIG. 4A is a longitudinal cross section showing an internal constitution of a proximal end section of the over-tube in the suturing apparatus according to the first embodiment.

In addition, FIG. 4A shows an internal constitution of the connecting section 6 at the proximal end side of the sheath section 7. A cylindrical connecting section main body 43 is provided at this connecting section 6. A large diameter hole section 43a for valve attachment and a screw hole section 43b are provided on the inner periphery face at the proximal end side of this connecting section main body 43.

Further, the proximal end section of the sheath section 7 is inserted into a cylinder of the connecting section main body 43. The distal end section of the fixing screw 42 screwed to be inserted into the screw hole section 43b is press-fitted to the internal peripheral face at the proximal end side of an insert section of this sheath section 7. Then, the proximal end side of the sheath section 7 is fixed while it is sandwiched between the fixing screw 42 and the connection section main body 43.

In addition, a ring shaped valve 45 is engaged to the large diameter hole section 43a at the proximal end side of the fixing screw 42. Further, a ring shaped valve stop 44 is engaged to the proximal end side of the valve 45, and is removably fixed to the hole section 43a.

The fixing screw 42, the connecting section main body 43, and the valve stop 44 are formed of a variety of metal materials such as stainless or aluminum, for example, or alternatively, a variety of plastic materials such as polypropylene, ABS, polycarbonate, polyacetal, or polysulfone. In particular, it is preferable that these elements are formed of a light weighted and rigid plastic material.

The valve 45 is formed of a variety of rubbers such as silicon rubber or fluorine rubber, or alternatively, a variety of thermoplastic elastomers. The inner diameter of the valve 45 is set so as to be smaller than the outer diameter of the endoscope 5. When the endoscope 5 is inserted into a center hole of the valve 45, air tightness can be maintained between the valve 45 and the endoscope 5. The thickness of the valve 45 is set to about 0.5 mm to 5 mm. This valve 45 can be replaced with a valve having its inner diameter different therefrom in accordance with the outer diameter of the endoscope 5. Further, a plurality of valves 45 is inserted into the hole section 43a, thereby making it possible to adjust air tightness.

Figure 4B:
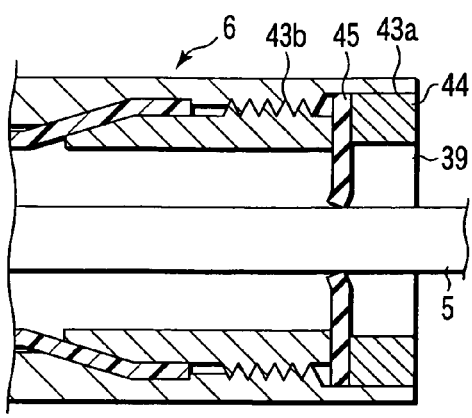
FIG. 4B is a longitudinal cross section showing a state before an endoscope is bent at a portion of an endoscope insert port at the proximal end section of the over-tube in the suturing apparatus according to the first embodiment.
Figure 4C:
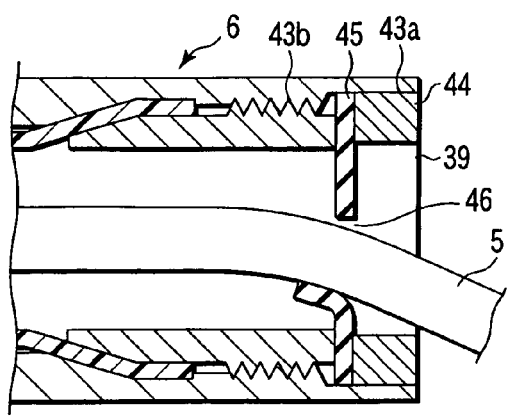
FIG. 4C is a longitudinal cross section showing a state after the endoscope has been bent at a portion of the endoscope insert port at the proximal end section of the over-tube in the suturing apparatus according to the first embodiment.

The inner diameter of the valve stop 44 is larger than that of the valve 45. An endoscope insert port 39 is formed by the internal cavity of the valve stop 44. It is preferable that a difference L between the inner diameter of the valve stop 44 and that of the valve 45 is about 1 mm to 2 mm, for example. In the case where the difference L in inner diameter between the valve stop 44 and the valve 45 is large, the movable range of the endoscope 5 is wide when the endoscope 5 is bent at a portion of the endoscope insert port 39. FIG. 4B shows a state before bending the endoscope 5 at a portion of the endoscope insert port 39. FIG. 4C shows a state after bending the endoscope at the above portion. In the case where the endoscope 5 is bent at a portion of the endoscope insert port 39, the gap 46 between the internal cavity of the valve 45 and the endoscope 5 is formed as shown in FIG. 4C, thus making it impossible to maintain air tightness. Because of this, it is preferable that the difference L in inner diameter between the valve stop 44 and the valve 45 is as small as possible.

As shown in FIG. 1A, one ligating lumen connecting section 43c communicated with the proximal end section of the ligating lumen 24 and two needle lumen connecting sections 43d communicated with the proximal end sections of the two needle lumens 23 are formed on the outer periphery face of the connecting section main body 43. The ligating lumen connecting section 43c and two needle lumen connecting sections 43d are disposed at the distal end side more than the fixing screw 42. These elements are sealed in order to maintain air tightness.

One end of an introducing tube 9 is connected to the ligating lumen connecting section 43c. This introducing tube 9 is then connected to the ligating lumen 24. With a similar constitution, one end of each of two connecting sheaths 11 of the needle manipulating section 3 is removably connected to the two needle lumen connecting sections 43d each, and is maintained in an air tight state. Then, the connecting sheaths 11 each are connected to the needle lumens 23. The ligating device 4 described later can be inserted into the introducing tube 9. A port 10 is connected to the proximal end side of this introducing tube 9. This port 10 has a valve for maintaining air tightness when the ligating device 4 is inserted through the introducing tube 9.

Further, the introducing tube 9 is formed of a plastic tube such as fluorine resin, polyethylene, polyamide, polyimide, polyurethane, or various thermo-plastic elastomers, for example. This introducing tube 9 may be covered with a plastic tube at the outside of the metal coil so that a kink hardly occurs. This introducing tube may be a metallically meshed plastic tube or a double tube.

In addition, a base member 12 is provided at the needle manipulating section 3. A grip 13 taking a gripping action during manipulation and two tubular housings 14 are provided at this base member 12. A distal end section of a slidable tubular needle slider 15 in an axial direction is connected to the proximal end section of each housing 14 removably and air tightly.

A pusher slider 16 is mounted in the tube of each needle slider 15 retractably and air tightly. The pusher slider 16 may not be removable.

The proximal end section of the connecting sheath 11 is fixed to the distal end section of each housing 14 with air tightness. The connecting sheath 11 is formed of a plastic tube such as fluorine resin, polyethylene, polyamide, polyimide, polyurethane, or various thermoplastic elastomers, for example. Further, the connecting sheath 11 may be covered with a plastic tube at the outside of the metal coil so that a kink hardly occur, may be a metallically meshed plastic tube, or may be a double tube.

The needle 28 shown in FIG. 2A can be slidably inserted into each connecting sheath 11. As shown in FIG. 2B, a tubular needle main body 29 is provided at the needle 28. A distal end section of a needle sheath 31 is connected to the proximal end section of this needle main body 29. A T-shaped bar pusher 33 can be slidably inserted into this needle sheath 31. The proximal end section of the needle sheath 31 is removably connected to the needle slider 15.

Figure 6A:
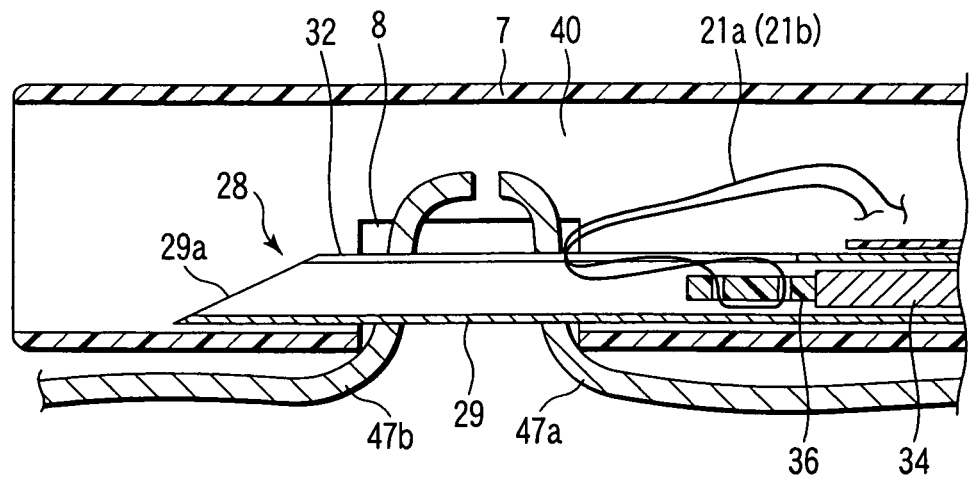
FIG. 6A is a longitudinal cross section showing a state in which a needle member is inserted into ruptured tissues suctioned into a treatment lumen through a side opening of the over-tube in the suturing apparatus according to the first embodiment.

Further, the needle 28 is slidably inserted through the needle lumen 23. When the needle slider 15 is completely pulled out from the housing 14, the distal end of the needle main body 29 is set so as to be disposed from the distal end of the needle lumen 23 to the proximal end side. FIG. 2A shows a state in which the distal end of the needle main body 29 is pushed out from the needle lumen 23 for clarity. When the needle slider 15 is completely pushed against the housing 14, the needle main body 29 moves to the frontal maximum movement position, as shown in FIG. 6A. At this time, the distal end of the needle 28 is set so as to be positioned at the distal end side of the side opening 8. When the protrusion length of the distal end of the needle 28 from the distal end of the side opening 8 is 10 mm or more, the living tissues suctioned from the side opening 8 is easily punched. In particular, it is desirable that the protrusion length is about 20 mm.

In addition, the needle main body 29 is formed of a metal pipe material such as stainless or nitinol. This needle main body 29 is set to about 0.5 mm to 1.5 mm in inner diameter, for example, and about 0.7 mm to 2 mm in outer diameter. A convergent sharp puncture end section 29a is provided at the distal end of this needle main body 29 so that the living tissues in the body cavity can be punctured.

Further, as shown in FIG. 2B, a slit 32 is extended backwardly from the distal end at a peripheral wall section of the needle main body 29. A T-shaped bar 36 (refer to FIG. 2C) described later is designed so as to be mounted in the needle 28. The length of the slit 32 is set to a length such that the distal end of the T-shaped bar 36 is not exposed from the distal end of the needle 28 when a connection portion between the T-shaped bar 36 and the thread 21 mounted in the needle 28 is positioned at the proximal end of the slit 32. Further, it is desirable that the length of this slit 32 is shorter than the protrusion length from the distal end of the side opening 8 to the distal end of the needle 28 when the needle 28 is completely pushed out from the needle lumen 23. Thus, it is desirable that the length of this slit 32 is about 10 mm to 20 mm, for example. In addition, the width of this slit 32 is dimensionally set such that the thread 21 can be easily inserted and an extruding member 34 described later and T-shaped bar 36 can not be inserted.

The needle sheath 31 is formed of a plastic tube such as fluorine resin, polyethylene, polyamide, polyimide, polyurethane, or various thermoplastic elastomers, or alternatively, is formed of a metal coil. The needle sheath 31 may be covered with a plastic tube at the outside of the metal coil so that a kink hardly occurs or may be a metallically meshed plastic tube.

The T-shaped bar pusher 33 is inserted into the needle 28 so that the pusher can be pushed out or recessed. An elongated pusher wire 35 made of a metal wire such as stainless and the elongated cylindrical extruding member 34 are provided at this T-shaped bar pusher 33. The pusher wire 35 is retractably inserted into the needle sheath 31 in an axial direction. The proximal end section of the extruding member 34 is connected to the distal end of this pusher wire 35. The pusher slider 16 is removably connected to the proximal end section of the pusher wire 35.

The extruding member 34 is made of a metal such as stainless, for example, or alternatively, is made of a variety of plastics. When the extruding member 34 is free of a hollow at its distal end, the T-shaped bar 36 mounted at the distal end of the needle 28 is easily pushed out. The outer diameter of the extruding member 34 should be as large as possible within the range such that the extruding member can slide the inside of the needle main body 29. In this manner, the T-shaped bar 36 mounted at the distal end of the needle 28 is easily pushed out.

The extruding member 34 is set to an length such that, when the pusher slider 16 of the needle manipulating section 3 is completely pulled out from the needle slider 15, the extruding member can be retracted into the needle 28, as shown in FIG. 5A. Further, while the pusher slider 16 is retracted, when the T-shaped bar 36 is mounted in the internal cavity of the needle main body 29, the T-shaped bar 36 is set so as to be completely retracted into the needle 28.

In addition, the extruding member 34 is set so as to be pushed out from the distal end of the needle 28 when the pusher slider 16 is completely pushed into the needle slider 15. It is desirable that the protrusion length of the extruding member 34 is 5 mm or more.

A cutter sheath 17 to be introduced into the ligating lumen 24 through the introducing tube 9 and a pusher tube 19 are provided at the ligating device 4 as shown in FIG. 1A. The pusher tube 19 is formed of a plastic tube such as fluorine resin, polyethylene, polyamide, polyimide, polyurethane, or various thermo-plastic elastomers, for example, or alternatively, is formed of a metal coil. The pusher tube 19 may be covered with a plastic tube at the outside of the metal coil so that a king hardly occurs or may be a metallic meshed plastic tube.

Further, the pusher tube 19 has an internal cavity such that two threads 21a and 21b described later can be slidably inserted over a full length. The internal cavity of the pusher tube 19 is dimensionally set such that knots 30a and 30b of the two threads 21a and 21b of the ligating unit 38 described later cannot be inserted respectively. In addition, the proximal end side of the pusher tube 19 is extended from the port 10 of the introducing tube 9 to the outside. Then, a pusher knob 20 is fixed to the proximal end section of this pusher tube 19.

The cutter sheath 17 is mounted in the axial direction so as to be slidable on the pusher tube 19. This cutter sheath 17 is formed of a plastic tube such as fluorine resin, polyethylene, polyamide, polyimide, polyurethane, or various thermoplastic elastomers, for example, or alternatively, is formed of a metal coil. This cutter sheath 17 may be covered with a plastic tube at the outside of the metal coil so that a kink hardly occurs or so that expansion or contraction hardly occurs, or alternatively, may be a metallically meshed plastic tube.

The cutter knob 18 is fixed to the proximal end section of the cutter sheath 17. In addition, a cutter 27 is fixed to the distal end section of the cutter sheath 17. This cutter 27 is provided as a metallic cylindrical member such as stainless. A blade capable of cutting threads 21a and 21b is fully provided at the distal end section of this cutter 27. The cutter 27 may be removably connected to the cutter sheath 17.

It is desirable that the outer diameter of the cutter sheath 17 of the ligating device 4 is about 1 mm to 3 mm. The length of the ligating device 4 is set to a length such that the distal end of the pusher tube 19 can be pushed out from the distal end of the sheath section 7 when the entire ligating device 4 is inserted through the port 10 of the introducing tube 9. Further, when the cutter sheath 17 is completely pulled to the proximal end side along the top of the pusher tube 19 by manipulation of the cutter knob 18, the pusher tube 19 is set so that its distal end is exposed.

As shown in FIG. 2C, two planar T-shaped bars 36 and two threads 21a and 21b (first thread 21a and second thread 21b) are provided at the ligating unit 38. The two threads 21a and 21b are inserted into the pusher tube 19. These threads 21a and 21b are formed of a material having its excellent biological compatibility which is similar to the suture thread generally used for surgical operation. For example, these threads are formed of a plastic material such as nylon or polyolefin, silk, a biological absorption material or the like. Further, as the threads 21a and 21b each, a commercially available suture thread itself may be used. These threads may be any of a single thread, a twisted thread, and knitted thread.

In addition, the diameter of each of the threads 21a and 21b is about 0.2 mm to 1 mm. In particular, it is preferable that the diameter is about 0.5 mm. Further, it is preferable that the threads 21a and 21b each are colored so as to be easily identified in the body cavity under an endoscope image. In particular, it is preferable that the color is blue or green.

The T-shaped bar 36 is formed of a metal such as stainless, or alternatively, a comparatively well slipped plastic material such as polysulfone, polyacetal, or nylon, for example. The T-shaped bar 36 is better formed of a material having its excellent biological compatibility such as nylon. It is desired that the T-shaped bar 36 should have a specific color to be distinguished in endoscope images, like the first thread 21a and the second thread 21b.

Two thread insert holes 37 are provided respectively at each T-shaped bar 36. The first thread 21a is slidably inserted into the two thread insert holes 37 of one T-shaped bar 36. Similarly, the second thread 21b is slidably inserted into the two insert holes 37 of the other T-shaped bar 36. It is desirable that the peripheral rim section of the thread insert hole 37 is chamfered so that threads 21a and 21b easily slide.

In addition, the distal end section of the first thread 21a is inserted into the two insert hole 37 of one T-shaped bar 36, and then, a knot 30b is formed to be knotted at the intermediate section of the second thread 21b. Similarly, the distal end section of the second thread 21b is inserted into the two thread insert holes 37 of the other T-shaped bar 36, and then, a knot 30a is formed to be knotted at the intermediate section of the first thread 21a.

The proximal end section of each of the threads 21a and 21b is extended to the outside from the proximal end section of the pusher tube 19 through the internal cavity of the pusher tube 19.

In addition, the knots 30a and 30b are formed in a knotting manner called Capstan knot or Roeder knot of the general surgical suture thread knots. One knot 30a is slidable on the first thread 21a, and the other knot 30b is slidable on the second thread 21b, respectively. Any knot other than the above knots may be available as long as such movement is enabled.

The size of each T-shaped bar 36 is dimensionally set such that the bar can be slidably inserted into the internal cavity of the needle main body 29 while the thread 21a or 21b is inserted. In addition, each T-shaped bar 36 is dimensionally set in width and thickness so as to be larger than the width of the slit 32 of the needle main body 29. It is desirable that the length of each T-shaped bar 36 is about 10 mm, for example. Each T-shaped bar 36 may be planar or cylindrical.

Now, operation of the suturing apparatus 1 of the present embodiment having the above constitution will be described here.

1. Assembly of Suturing Apparatus 1 According to the Present Embodiment

First, the cutter sheath 17 and the pusher tube 19 of the ligating device 4 are inserted into the ligating lumen 24 through the introducing tube 9. At this time, the pusher tube 19 of the ligating device 4 is pushed out from the distal end of the sheath section 7. Then, the two threads 21a and 21b of the ligating unit 38 are inserted into the pusher tube 19 through the distal end internal cavity of the pusher tube 19. At this time, the two threads 21a and 21b are inserted to be pushed out from the pusher knob 20 to the outside, as shown in FIG. 1A.

Subsequently, the pusher slider 16 of the needle manipulating section 3 is completely pulled out from the needle slider 15, and the T-shaped bar pusher 33 is completely retracted into the needle 38. Further, while the needle 28 is pushed out from the needle lumen 23, two T-shaped bars 36 each are mounted on the distal end internal cavity of two needles 28. At this time, the two threads 21a and 21b are mounted so as to pass the slit 32 of the needle 28.

Then, the needle 28 is completely retracted into the needle lumen 23, and the ligating device 4 is also retracted so as to apply gentle tension to the threads 21a and 21b exposed to the inside of the endoscope lumen 25.

2. Suction, Puncture, and Piercing Ligating Members Into Living Tissues

As shown in FIG. 1A, the endoscope 5 is inserted into the over-tube 2. At this time, the distal end of the endoscope 5 is pushed out from the distal end of the over-tube 2. In this state, the over-tube 2 is inserted into the patient's body while the patient's body cavity is observed through an endoscope image. Then, the distal end of the endoscope 5 is moved to the proximity of ruptured living tissues 47a and 47b (refer to FIG. 6A).

Next, the distal end of the endoscope 5 is pulled back to the proximal end side of the side opening 8 of the over-tube 2. At this time, the over-tube 2 is advanced or retracted, or alternatively, rotated while the tube is observed through an endoscope image. Then, positioning is carried out so that the side opening 8 is positioned upwardly of the ruptured living tissues 47a and 47b targeted to be sutured.

In this state, a suction function of the endoscope 5 is actuated. In this manner, the ruptured living tissues 47a and 47b are suctioned into the treatment lumen 40 through the side opening 8.

Then, the living tissue 47a is observed, whereby it is checked whether or not a target puncture site is located on an extension line of the needle 28. In the case where the puncture position is displaced, suctioning is released, and the positioning of the side opening 8 is retried. Then, the ruptured living tissues 47a and 47b are suctioned again.

Before retrying positioning of the side opening 8, the currently used over-tube may be replaced with another over-tube 2 in which the size of the side opening 8 is different therefrom.

In addition, before inserting the over-tube 2, markings such as ink may be injected in advance at the puncture target positions of the living tissues 47a and 47b by using the endoscope 5 and general endoscopic injection needle. In this case, the puncture position of the suctioned living tissues 47a and 47b each can be checked more easily.

Next, the two needle sliders 15 of the needle manipulating section 3 are advanced to the distal end side relevant to the housing 14, respectively. In this manner, the two needles 28 are pushed out in parallel from the distal end of each needle lumen 23. Protruding manipulations of these two needle sliders 15 may be carried out at the same time or may be carried out separately.

Together with the protruding operation of the two needles 28, as shown in FIG. 6A, each needle main body 29 punctures the ruptured living tissues 47a and 47b. At this time, the needle manipulating section 3 is disposed at a position spaced from the connecting section 6 by means of the connecting sheath 11. Thus, an assistant who manipulates the needle manipulating section 3 and a surgeon who manipulates the endoscope 5 can carry out manipulation at the positions spaced from each other. As a result, interference of these mutual manipulations can be prevented.

Figure 6B:
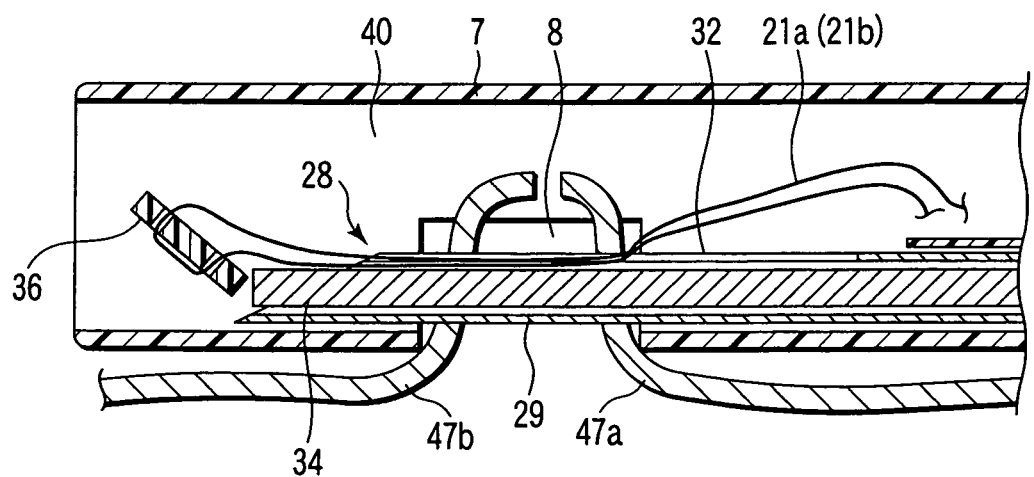
FIG. 6B is a longitudinal cross section showing a state in which a T-shaped bar mounted in a needle of the over-tube in the suturing apparatus according to the first embodiment is pushed out from the needle.

Next, the two pusher sliders 16 are pushed against the needle slider 15 at the distal end side. As shown in FIG. 6B, the extruding member 34 is extruded from the distal end of the needle 28, and pushes out the T-shaped bar 36 mounted in the needle 28 from the needle 28. In this manner, a part of the threads 21a and 21b at the distal end side more than the knots 30a and 30b is punctured into the ruptured living tissues 47a and 47b. When the threads 21a and 21b are pulled after the T-shaped bar 36 has been pushed out from the needle 28, the T-shaped bar 36 is hooked on the living tissues 47b. Thus, the threads 21a and 21b punctured into the living tissues 47a and 47b do not slip off.

Next, the pusher slider 16 and the needle slider 15 are pulled out to the proximal end side. In this manner, as shown in FIG. 7A, the needle 28 is removed from the ruptured living tissues 47a and 47b. In this state, suction by the suction function of the endoscope 5 is released. In this manner, the ruptured living tissues 47a and 47b are dropped from the side opening 8 to the outside of the treatment lumen 40. Instead of releasing suctioning here, such suctioning may be released after ligation of the ligating unit 38.

3. Ligation/Cutting of Ligating Member

Next, the threads 21a and 21b exposed to the outside from the pusher knob 20 of the ligating device 4 are pulled toward the proximal end side, and a tension is applied to the threads 21a and 21b. In this state, the pusher knob 20 is pushed out frontally. In this manner, the pusher tube 19 is moved to the distal end side. Together with advancing operation of this pusher tube 19, the knots 30a and 30b are pushed out to the distal end side at the distal end of the pusher tube 19, as shown in FIG. 7B. At this time, the threads 21a and 21b move as indicated by the arrow in FIG. 2C, and the knots 30a and 30b are close to the T-shaped bar 36.

In this manner, the ruptured living tissues 47a and 47b are moved in a gradually closed direction (connected direction). At this time, the pusher tube 19 is advanced while the connection state of the ruptured living tissues 47a and 47b is observed through the endoscope image. Then, at a time when the knots 30a and 30b abut against one living tissue 47a as shown in FIG. 8A, the ruptured living tissues 47a and 47b come into contact with each other. Then, the ruptured portion is sutured in its closed state by means of the threads 21a and 21b.

Next, the distal end of the pusher tube 19 is pulled back to its original state. Then, the over-tube 2 is advanced. In this manner, the living tissue 47 sutured as shown in FIG. 8B is removed from the side opening 8. At this time, the threads 21a and 21b on the proximal end side of the knots 30a and 30b are hooked on the thread receiving section 22 at the substantially same time.

Then, the threads 21a and 21b exposed to the proximal end side from the pusher knob 20 are pulled toward the proximal end side, and a tension is applied to the threads 21a and 21b. In this state, the cutter knob 18 is pushed against the distal end side, and the cutter sheath 17 is pushed out frontally. In this manner, the blade of the cutter 27 cuts the threads 21a and 21b at the proximal ends of the knots 30a and 30b.

Lastly, the over-tube 2 and the endoscope 5 are removed from the inside of the patient's body.

When the ruptured living tissues 47a and 47b cannot be sutured by the above manipulation one time, a series of the above manipulations are repeatedly carried out in accordance with the length or range which requires suturing. This makes it possible to completely suture the ruptured living tissues 47a and 47b.

In the case where an artificial valve is formed for a patient with the gastroesophageal reflux disease by using this suturing apparatus 1, the following manipulations shown in FIG. 10 to FIG. 12 are carried out. That is, the over-tube 2 is inserted into an esophagus 48. Then, as shown in FIG. 10, the side opening 8 of the over-tube 2 is positioned at an esophageal wall 50 immediately above a cardiac part of stomach 49. In this state, the above manipulation is carried out, thereby making it possible to suture the esophageal wall 50 and a gastric wall 51 as shown in FIG. 11 and to form an artificial valve 52 as shown in FIG. 12.

With the above constitution, the following effect is attained. That is, in the suturing apparatus 1 according to the present embodiment, the ruptured living tissues 47a and 47b in the body can be ligated or sutured in combination with the endoscope 5. Thus, a much lower invasive repair can be carried out for the patients. As a result, there is provided an advantageous effect that the hospitalization term can be reduced, and thus, a burden on the patients can be reduced in the aspect of cost such as hospitalization cost.

In the suturing apparatus 1 according to the present embodiment, there is provided the ligating device 4 for puncturing the ligating unit 38 through the ruptured living tissues 47a and 47b, followed by ligating the ligating unit 38. Therefore, unlike the conventional apparatus, there is no need to temporarily remove the device from the inside to the outside of the body, and then, ligate the threads outside of the body. As a result, treatment/manipulation for ligating the living tissues 47a and 47b is very simplified as compared with the conventional one, and the treatment time is significantly reduced.

Further, in the suturing apparatus 1 according to the present embodiment, the cutter 27 is provided as means for cutting a redundant portion of the ligating unit 38 after ligation. Thus, there is no need to re-insert another cutting device into the patient's body. In this respect as well, treatment/manipulation is simplified, and the treatment time can be reduced.

In addition, when a resected portion or damaged portion of a living tissue is sutured, the entire living tissue targeted to be sutured is retracted into the treatment lumen 40 by means of suctioning, and then, the ligating unit 38 can be punctured. Therefore, it is possible to easily suture a region in wide range one time as compared with a case where an attempt is made to carry out suturing by means of a clipping apparatus or the like.

The living tissues 47a and 47b are suctioned into the treatment lumen 40 positioned frontally on an axis that is substantially identical to the endoscope 5. Thus, before puncturing the needle 28, it is possible to easily and reliably check whether or not the needle 28 can be correctly punctured into a target site of the living tissues 47a and 47b each. Further, the distal end of the endoscope 5 is moved forwardly or backwardly to the side opening 8 or bending manipulation is carried out, thereby making it possible to adjust the living tissues 47a and 47b so as to be easily observed. This makes it possible to ensure fine control of the puncture position of the needle 28 and makes it possible to carry out reliable ligation or suturing. Further, the treatment/manipulation is simplified, and the treatment time is significantly reduced.

The needles 28 are disposed in parallel to each other with constant intervals, and thus, the puncture-in point and puncture-out point of the needle 28 on the living tissues 47a and 47b are defined with desired constant intervals. As a result, the stitch intervals are not reduced extremely, and can be controlled reliably. As a result, treatment/manipulation is simplified, and the treatment time is significantly reduced. Even when it is required to carry out stitching plural times, a distance in one stitch can be controlled constantly. Thus, suturing can be carried out reliably with a small number of stitches.

The two needles 28 are provided in advance, and thus, the two needles 28 can be punctured immediately through one manipulation for suctioning the living tissues 47a and 47b from the side opening 8. In this respect as well, treatment/manipulation is simplified, and the treatment time is significantly reduced.

The endoscope 5 and treatment lumen 40 of the over-tube 2 serving as a chamber into which the living tissues 47a and 47b are suctioned are disposed in a substantially coaxial manner. Thus, a larger space capable of suctioning the living tissues 47a and 47b can be obtained without increasing the external diameter of the entire system including the endoscope 5 and suturing apparatus 1. As a result, the patient's pain can be reduced during system insertion. In addition, the needle 28 is housed in the suturing apparatus 1, thus, making it possible to insert the device into the patient's body without damaging the internal cavity.

It is desirable that marking 41 of easily identifiable color such as blue or green is provided to the side opening 8 of the sheath section 7 along its outer periphery rim section, as in the modified example shown in FIG. 13. In this case, the side opening 8 is easily recognized under its endoscope image. Further, it is desirable that the marking 41 at the outer periphery of the side opening 8 is scaled in steps of ½ or ⅓ along the axial direction of the sheath 7. This makes it easy to carry out positioning of the side opening 8. If the marking 41 is scaled, the scale should extend in the circumferential direction, and may extend along the entire circumference of the side opening 8. In addition, the outer periphery rim section of the side opening 8 may be scaled along the circumferential direction of the sheath section 7. When the side opening 8 is large in size, the number of scales may be increased more. The scale may differ in color from the other parts of the marking 41, so that it may be easily recognized.

FIG. 14 to FIG. 20B show a second embodiment of the present invention. According to the present embodiment, a part of the suturing apparatus 1 according to the first embodiment (refer to FIG. 1A to FIG. 12) has been modified as follows. In the present embodiment, like elements identical to the suturing apparatus 1 of the first embodiment are designated by like reference numerals. A duplicate description is omitted here. Here, only elements different from those of the first embodiment will be described.

As shown in FIG. 14, in the over-tube 2 of the present embodiment, a suction port 53 is provided at the connecting section 6. This suction port 53 communicates with an endoscope lumen 25. One end of a connecting tube 55a of a suction apparatus 54 is removably connected to the suction port 53.

A suction source 59 is provided at the suction apparatus 54. One end of a connecting tube 55d is removably connected to this suction source 59. The other end of this connecting tube 55d is connected to a switching valve 58. One end of each of the other two connecting tubes 55c and 55e is connected to the switching valve 58.

The other end of the connecting tube 55e is removably connected to a suction port 60 of the endoscope 5. Further, the other end of the connecting tube 55c is connected to an adjusting valve 57 for adjusting a suction pressure. A pressure gauge 56 is connected to this adjusting valve 57 via the connecting tube 55b. The other end of the connecting tube 55a is connected to this pressure gauge 56. Then, the suction pressure of the connecting tube 55a is displayed on the pressure gauge 56.

A connection state among the connecting tubes 55d, 55c, and 55e can be arbitrarily selected as any one of the following switching states by means of switching operation of the switching valve 58. That is, the connection state can be arbitrarily selected as any one of: a first switching state in which a negative pressure (suction pressure) is applied to both of the connecting tubes 55c and 55e; a second switching state in which a negative pressure (suction pressure) is applied to the connecting tube 55c; a third switching state in which a negative pressure (suction pressure) is applied to the connecting tube 55e; and a fourth switching state in which a negative pressure is not applied to both of these tubes.

Instead of the switching valve 58, two opening/closing valves capable of opening/closing two tube paths may be provided as follows. That is, a first opening/closing valve capable of opening/closing between the connecting tube 55a and the suction port 53 is interposed, and a second opening/closing valve capable of opening/closing between the connecting tube 55e and the suction port 60 is interposed.

Further, an adjusting valve 67 may be provided between the connecting tube 55e and the suction base 60.

In the present embodiment, the thread receiving section 22 is not provided at the side opening 8 of the over-tube 2.

As shown in FIG. 15A, a slit 61 is provided at the distal end section of the peripheral wall section of the needle lumen 23. This slit 61 is extended backwardly from the distal end. The proximal end side of this slit 61 is disposed to be identical to or more proximal than the proximal end position of the slit 32 of the needle main body 29 according to the first embodiment. It is desirable that the length of this slit 61 is about 10 mm to 30 mm, for example.

The width of this slit 61 may be dimensionally defined such that the thread 21 can be easily inserted, for example. When the needle lumen 23 is formed of a flexible plastic material, the slit 61 may be defined to an extent such that the slit is cut by a thin blade. In this case, when the thread 21 slides, the needle lumen 23 at the periphery of the slit 61 is deformed, and the thread can be easily slide.

As shown in FIG. 15B, in the ligating device 4 of the present embodiment, a manipulating section 65 is fixed to the proximal end side of a ligating sheath 62. A metallic manipulating wire 63 is slidably inserted into this ligating sheath 62. A hook 64 is connected to the distal end of the manipulating wire 63, and a ligating slider 66 being slidable on the manipulating section 65 is connected to the proximal end. The hook 64 is protruded or recessed from the distal end of the ligating sheath 62 by advancing or retracting manipulation of the ligating slider 66.

The cutter sheath 17, cutter 27, and cutter knob 18 identical to those of the first embodiment slidably cover the ligating sheath 62.

The ligating sheath 62 has flexibility, and is formed of: a plastic tube such as fluorine resin, polyethylene, polyamide, polyimide, polyurethane, or various thermoplastic elastomers; or alternatively, is formed of a metal coil. The ligating sheath 62 may be covered with a plastic tube at the outside of the metal coil or may be a metallically meshed plastic tube so that a kink hardly occurs.

The hook 64 is shaped so that a loop section 68 of a ligating unit 67 can be removably engaged, and is formed of a metal such as stainless so as not to be easily deformed.

Figure 16:
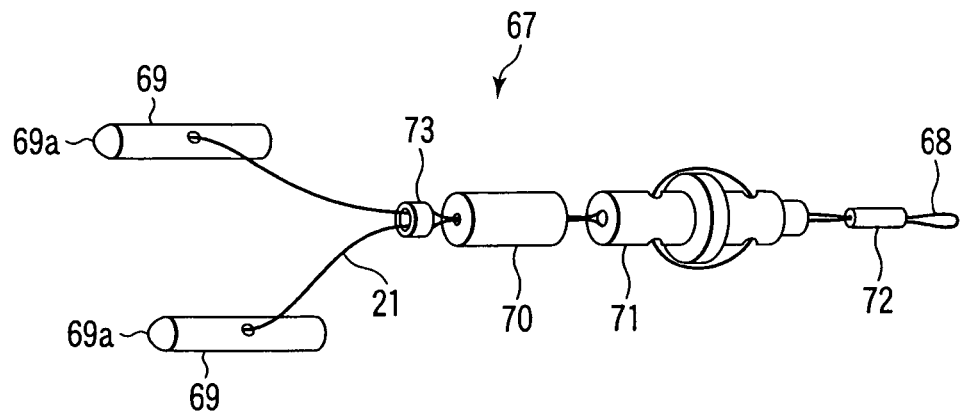
FIG. 16 is a perspective view showing an appearance of a ligating unit in the suturing apparatus according to the second embodiment.

FIG. 16 shows the ligating unit 67 of the present embodiment. At this ligating unit 67, a T-shaped bar 69 is fixed to both ends of the thread 21. The thread 21 is returned at its substantial center, and a loop section 68 is formed. The distal end side of this loop section 68 is fixed by bonding while it is inserted into the internal cavity of a connecting pipe 72.

Figure 17:
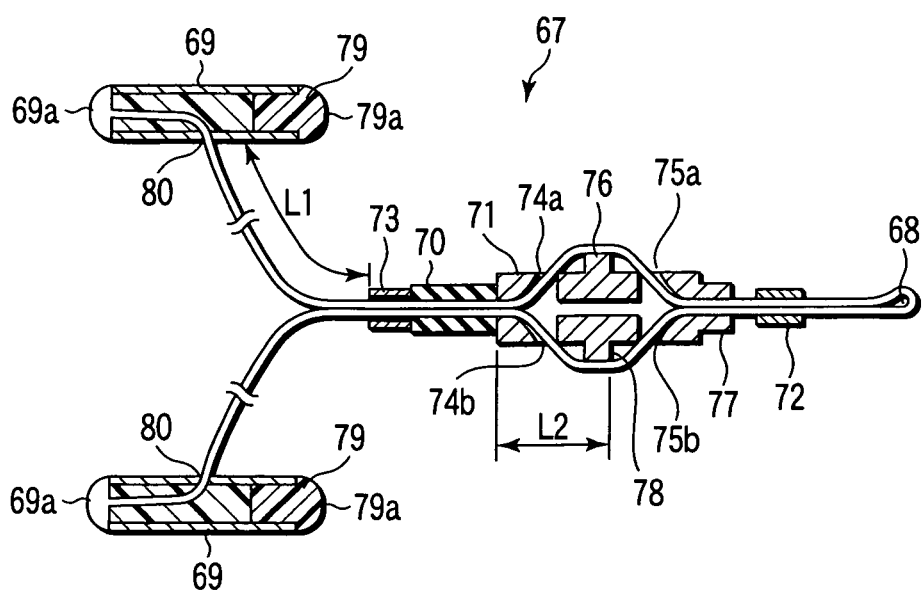
FIG. 17 is a longitudinal cross section showing a ligating unit in the suturing apparatus according to the second embodiment.

Further, on the thread 21 between the loop section 68 and two T-shaped bars 69 each, a substantially cylindrical receiving member 71, a cylindrical stopper 70, and a tube 73 are slidably inserted sequentially as shown in FIG. 17.

The ligating unit 67 may be formed by using the two threads 21 in the following manner. That is, the T-shaped bars 69 are fixed to the distal ends of the two threads 21, respectively. Then, the respective threads 21 are routed through the receiving member 71, the stopper 70, and the tube 73. Thereafter, the proximal end side of one thread 21 is returned, whereby the returned proximal end side may be formed to be fixed to the internal cavity of the connecting pipe 72 together with the proximal end side of the other thread 21.

The receiving member 71 is made of a metal such as stainless, or alternatively, a plastics such as polypropylene, ABS, polyacetal, or polycarbonate. An annular protrusion portion 76 is provided integrally at the substantial intermediate section in the axial direction of the receiving member 71. A convergent section 77 is provided at the proximal end section of the receiving member 71. As shown in FIG. 19A, this convergent section 77 is supported to be inserted into the distal end section of the ligating sheath 62. Therefore, there is no step between an outer periphery face of the ligating sheath 62 and an outer periphery face of the receiving member 71 so that the cutter sheath 17 can be advanced or retracted smoothly.

A pair of distal end side holes 74a and 74b capable of inserting the thread 21 are punched at the distal end side more than the annular protrusion portion 76 of the receiving member 71. A pair of proximal end side holes 75a and 75b capable of inserting the thread 21 are punched at the proximal end side more than the annular protrusion portion 76. Inclined faces are formed respectively at the inside face of the distal end side of the distal end side holes 74a and 74b each and at the inside face of the proximal end side of the proximal end side holes 75a and 75b each. By these inclined faces, the thread 21 inserted into the distal end side holes 74a and 74b and the proximal end side holes 75a and 75b are easily inserted and easily removed. Further, an abutment face 78 of the cutter 27 is formed on the proximal side face of the annular protrusion portion 76.

Each of the two return sections returned at the loop section 68 of the thread 21 is inserted into the receiving member 71 through a proximal end opening of the receiving member 71. Subsequently, these two return sections of the thread 21 are guided to the outside of the receiving member 71 through the proximal end side holes 75a and 75b. Next, the return sections are guided to the inside of the receiving member 71 through the distal end side holes 74a and 74b via the outside of the annular protrusion portion 76. Further, the guided return sections are inserted into the outside through the distal end opening of the receiving member 71. Then, at the distal end side of the receiving member 71, the two threads 21 are press-fitted to the internal cavity of a stopper 70 in a bundled state.

A full length of the receiving member 71 is about 5 mm to 10 mm, for example. As shown in FIG. 17, the length of the remaining thread 21 after cut is determined depending on a dimension L2 between a distal end face of the receiving member 71 and the abutment face 78. Thus, a shorter length L2 is desirable, and the length is defined as about 2 mm to 5 mm, for example.

Dimensions of the receiving member 71, the annular protrusion portion 76, and the cutter 27 are defined as follows. Assuming that the outer diameter of the receiving member 71 is defined as A, the outer diameter of the annular protrusion portion 76 is defined as B, and the inner diameter of the cutter 27 is defined as C, these diameters are about 1 mm to 3 mm, for example, in all. A relationship is defined as A<C, B>C, and B−A=about 0.2 mm to 1 mm. The proximal end holes 75a and 75b may be displaced forwardly or backwardly with intervals, respectively.

A length L1 of the exposure portion of the thread 21 from the T-shaped bar 69 to the tube 73 is defined to be larger than a distance from the needle tip to the proximal end side of the side opening 8 when the needle 28 is completely protruded. It is desirable that the length L1 of the exposure portion of this thread 21 is about 30 mm to 50 mm, for example. In this manner, when the T-shaped bar 69 is pushed out, the tube 73 does not abut against a living tissue 47 before the T-shaped bar 69 is protruded and slips off from the needle tip of the needle 28. As a result, the T-shaped bar 69 is easily extruded.

The T-shaped bar 69 is provided as a cylindrical member made of a metal such as stainless, or alternatively, a plastic material with its excellent biological compatibility such as polysulfone, polyacetal, or nylon, for example. In particular, the T-shaped bar 69 is better formed of a material such as nylon.

A side hole 80 is dripped at the outer periphery face of the T-shaped bar 69. The thread 21 is inserted into this side hole 80. The end section of the thread 21 is protruded to the outside from one end of the T-shaped bar 69. Further, the end section of the thread 21 protruded to the outside from one end of the T-shaped bar 69 is rounded in a hemispheric shape as is by thermoforming so as to form a slip-off proof 69a. The slip-off proof 69a at the end section of the thread 21 is rounded, whereby both ends of the T-shaped bar 69 can be prevented from damaging the living tissues in the patient's body.

The end section of the thread 21 is knotted, whereby slip-off proofing and prevention of damage of the living tissues may be ensured. In this state, the T-shaped bar 69 and the thread 21 are further fixed by a bonding agent, or alternatively, caulking.

Further, a sealing member 79 formed of a metal or various plastic materials is engaged with, and fixed to, an internal cavity at the other end section of the T-shaped bar 69. A sealing end section 79a whose shape is rounded in a hemispheric shape is formed at the proximal end of the sealing member 79.

In the case where the T-shaped bar 69 is formed of a plastic material, both ends of the main body itself of the bar shaped T-shaped bar 69 are formed in advance in a hemispheric shape, and then, the end section of the thread 21 may be connected by thermal deposition or ultrasonic deposition.

By injection molding or the like, the T-shaped bar 69 may be integrally molded of the same plastic at one end of the thread 21. In this case, as described previously, two pairs of threads 21 are combined with each other, thereby forming the ligating unit 67.

Further, it is desirable that a connecting portion between the T-shaped bar 69 and the thread 21 is at the substantial center position of the T-shaped bar 69. As long as a length from the connecting section between the T-shaped bar 69 and the thread 21 to both ends of the T-shaped bar 69 is such that the living tissues in the patient can be well engagingly fitted and is free of slip-off, the connecting section of the thread 21 may be dislocated from the substantial center position of the T-shaped bar 69.

The outer diameter of the T-shaped bar 69 is dimensionally defined such that the bar can be inserted into the internal cavity of the needle main body 29 in a slidable state. Further, the outer diameter of the T-shaped bar 69 is larger than the width of the slit 32. It is desirable that the length of the T-shaped bar 69 is about 10 mm. The T-shaped bar 69 may be formed in a planer shape without being limited to a cylindrical member.

The tube 73 is provided as a cylindrical member made of: a metal such as stainless; or alternatively, a plastic material with its biological compatibility such as polysulfone, polyacetal, nylon, fluorine resin or the like, the plastic material being more hardy ruptured than a material of a stopper 70. In particular, the tube 73 may be better formed of a material such as nylon.

The stopper 70 is formed of a comparatively flexible material such as various rubbers or various thermoplastic elastomers. Thus, when the stopper 70 is moved to the distal end side for ligating, excessive force is applied to the stopper 70 through the thread 21. As a result, the stopper 70 may be ruptured. In the present embodiment, the tube 73 is inserted into the distal end side of the stopper 70, thereby making it possible to prevent rupture of the stopper 70. When the stopper 70 is formed of a hardly ruptured material, the tube 73 may not always be provided.

Now, operation of the above constructed suturing apparatus 1 according to the present embodiment will be described here. Only elements different from those of the first embodiment will be described here. The ligating unit 67 is mounted in advance on the distal end of the needle 28 and the ligating device 4 before using the suturing apparatus 1 according to the present embodiment. During this mounting work, the ligating slider 66 is pushed out in advancing direction, making the ligating sheath 62 project from the distal end of the sheath section 7. In this manner, as shown in FIG. 15A, the distal end hook 64 is protruded from the distal end of the ligating sheath 62 via the manipulating wire 63. Then, the loop section 68 of the ligating unit 67 is hooked on the hook 64. In this state, the ligating slider 66 is pulled toward the proximal end side. By pulling manipulation of this slider 66, the manipulating wire 63 is retracted, and the hook 64 is retracted into the ligating sheath 62. At this time, the receiving member 71 is pulled backwardly via the hook 64, and the receiving member 71 is gently abutted against the distal end of the ligating sheath 62. Then, the slider 66 is further manipulated to be pulled, and the manipulating wire 63 is retracted, whereby a convergent section 77 of the receiving member 71 is supported to be inserted into the distal end opening of the ligating sheath 62, as shown in FIG. 19A.

Next, the T-shaped bars 69 are inserted respectively into the distal end internal cavities of the two needles 28. At this time, the thread 21 extending from the T-shaped bar 69 is inserted so as to pass through the slit 32. Then, the needle 28 is pulled toward the proximal end side, and the needle 28 is retracted into the needle lumen 32. At this time, as shown in FIG. 18A and FIG. 18B, the thread 21 exposed from the slit 32 passes through the slit 61.

Next, the endoscope 5 is inserted into the over-tube 2 as in the first embodiment. At this time, the distal end of the endoscope 5 is protruded from the distal end of the over-tube 2. In this state, the over-tube 2 is inserted into the patient's body while the patient's body cavity is observed through an endoscope image. Then, the distal end of the endoscope 5 is moved to the proximity of the ruptured living tissues 47a and 47b (refer to FIG. 6A).

Subsequently, positioning is carried out so that side opening 8 is positioned upwardly of the ruptured living tissues 47a and 47b targeted to be sutured.

In this state, a suction function of the endoscope 5 is actuated. In this manner, as in the first embodiment, the ruptured living tissues 47a and 47b are suctioned from the side opening 8 of the over-tube 2.

In the present embodiment, when an attempt is made to carried out a work of suctioning the ruptured living tissues 47a and 47b from the side opening 8 of the over-tube 2, the switching valve 58 is manipulated so that a negative pressure is applied to both of the connecting tubes 55c and 55e. In this case, a suction force acts with a portion in a gap between the endoscope lumen 25 and the endoscope 5. Thus, a stronger maximum suction pressure can be obtained in the treatment lumen 40 as compared with a case where a suction force is merely acted via a suction channel of the endoscope 5.

The adjusting valve 57 is manipulated while a pressure is checked by the pressure gauge 56, whereby the suction pressure can be freely controlled.

The switching valve 58 may be manipulated so that a negative pressure is applied only to one connecting tube 55c. In this case, the maximum suction pressure is lower than that when suctioning is applied via both of the suction channel of the endoscope 5 and the endoscope lumen 25. However, in this case, there is an advantage that suction manipulation of the endoscope 5 can be eliminated.

Instead of the switching valve 58, in the case where there are provided: a first opening/closing valve capable of opening/closing between the connecting tube 55a and the suction port 53; and a second opening/closing valve capable of opening/closing between the connecting tube 55e and the suction port 60, the operation similar to the above can be achieved by combining the respective opening/closing valve manipulations.

Two needles 28 are punctured while the ruptured living tissues 47a and 47b in the side opening 8 of the over-tube 2 are suctioned and inserted. In this state, the T-shaped bars 69 are pushed out respectively from the two needles 28.

The needles 28 are then removed, whereby the two threads 21 of the ligating unit 67 are set so as to be inserted into the ruptured living tissues 47a and 47b, as shown in FIG. 19A. In this state, the ligating slider 66 is pulled. Then, as shown in FIG. 19B, the stopper 70, the receiving member 71, and the tube 73 move to the T-shaped bars 69, and the ruptured living tissues 47a and 47b are ligated.

Next, while the ligating slider 66 is maintained, the cutter knob 18 is manipulated to be pushed out against the distal end side. By this manipulation, the cutter sheath 17 advances while the sheath is guided to the ligating sheath 62. Then, the cutter 27 is engaged with the proximal end section of the receiving member 71, and the cutting blade of the cutter 27 abuts against the abutment face 78. At this time, the proximal end side of the two threads 21 inserted into the receiving member 71 is cut in close proximity to the proximal end side holes 75a and 75b, as shown in FIG. 19C.

At this time, the proximal end side of the threads 21 is pulled by the manipulating wire 63, and a tension is applied. Thus, the cutter 27 cuts well. As shown in FIG. 19C, the two vertical threads 21 are not cut at the same time, and a time difference may occur. However, the two vertical threads 21 are connected by the connecting pipe 21, and thus, a tension is maintained even if these threads are cut one by one. Thus, the cutter still cuts well.

When the proximal end side holes 75a and 75b are shifted forwardly or backwardly, one of the threads 21 is cut by the cutter 27, and then, the other thread 21 is cut. As a result, the cutter 27 does not come into contact with both of the threads 21 at the same time. Thus, the cutting force applied to the threads 21 is not dispersed, and the threads 21 are easily cut.

If the two threads 21 are cut at their proximal end side, the ligating sheath 62 and the receiving member 71 are separated from each other. Then, the ligating device 4 and ligating unit 67 are separated from each other. After that, the over-tube 2 and the endoscope 5 are removed from the patient's body.

Figure 20A:
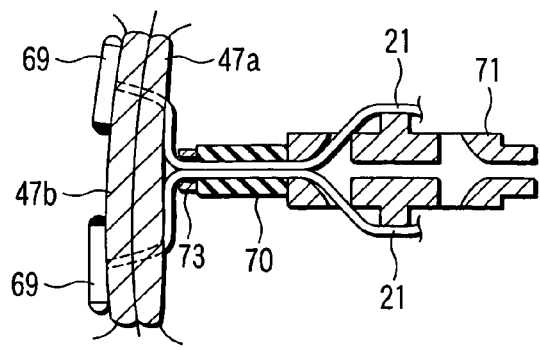
FIG. 20A is a longitudinal cross section of a ligating unit showing a state in which the ligating device and the ligating unit are separated from each other.
Figure 20B:
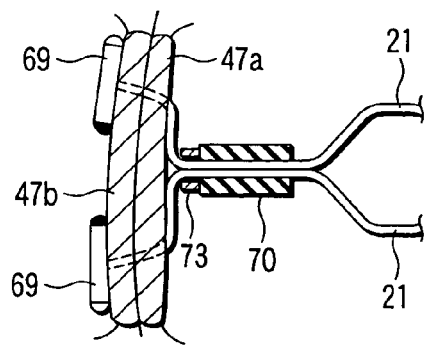
FIG. 20B is a longitudinal cross section of a ligating unit showing a state in which the receiving member is separated from the ligating unit.

At this time, as shown in FIG. 20A, the receiving member 71 of the ligating unit 67 is left in the body. This receiving member 71 slips off from the threads 21 naturally while the receiving member is left in the patient's body. The receiving member 71 that has slipped off from the threads 21 is naturally discharged to the outside of the body via the patient's digestive tract. Thus, as shown in FIG. 20B, only the threads 21 maintained in a tided state by the stopper 70 are left in the patient's body, and ligating operation of the ruptured living tissues 47a and 47b completes.

In the above constructed present embodiment, advantageous effect similar to that of the first embodiment is attained. Further, in the present embodiment, the following advantageous effect is attained in addition to that similar to the first embodiment.

That is, in the present embodiment, when the ruptured living tissues 47a and 47b in the patient's body are suctioned into the side opening 8 of the over-tube 2, suctioning via the endoscope lumen 25 as well as that via the suction channel of the endoscope 5 can be acts at the same time. Thus, a higher suction pressure can be obtained in the treatment lumen 40. In this manner, the range or quantity of living tissues that can be suctioned from the side opening 8 is increased, and thus, the needle 28 can be punctured into the living tissues in a wider range. In addition, the needle 28 can be punctured into the deeper living tissues. Thus, there is no danger that the living tissues are ruptured, and the thread 21 easily slips off from the living tissues. As a result, the suture range is broadened, and suturing can be carried out more reliably as well.

A suction pressure can be controlled by the adjusting valve 57. Thus, the range or quantity of living tissues that are suctioned from the side opening 8 into the treatment lumen 40 as well can be controlled. As a result, the suture range can be arbitrarily adjusted as well.

The suturing apparatus 1 of the present embodiment can be applied to a case where the living tissues are inflated/ligated, and an artificial valve is provided for the purpose of repairing the endoscopic gastroesophageal reflux disease. In this case, the size of such inflation can be arbitrarily adjusted, thus making it possible to form an artificial valve of size according to the degree of disease.

In the present embodiment, unlike the first embodiment, there is no need to insert the thread 21 over the full length of the pusher tube 19 when the ligating unit 67 and ligating device 4 are mounted. Thus, the work of mounting the ligating unit 67 becomes very easy.

In the present embodiment, when a redundant portion of the thread 21 is cut by the cutter 27, unlike the first embodiment, there is eliminated a complicated manipulation that the living tissues 47 are removed from the side opening 8, and the thread 21 is hooked on the thread receiving section 22. Thus, treatment/manipulation is simplified more, and the treatment time is reduced more.

Figure 21A:
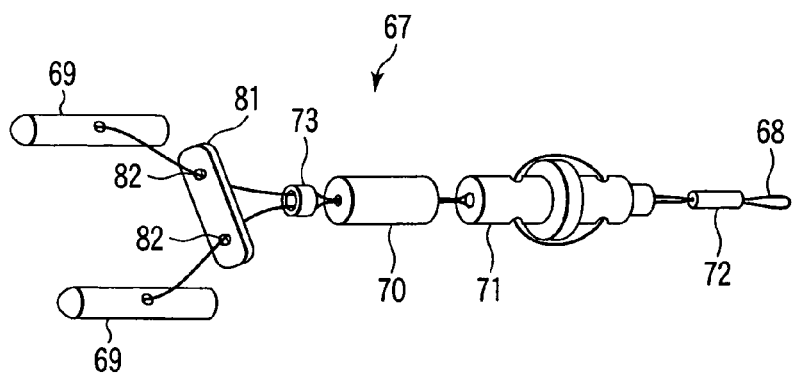
FIG. 21A is a perspective view showing a first modified example of the ligating unit in the suturing apparatus according to the second embodiment.
Figure 21B:
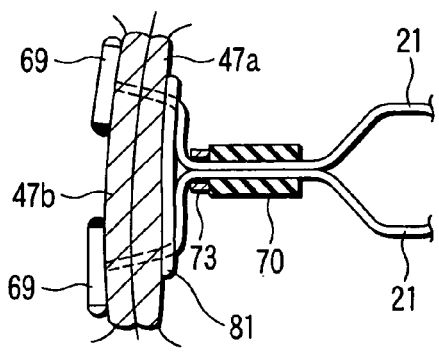
FIG. 21B is a longitudinal cross section showing a state in which living tissues are ligated by a ligating unit according to the first modified example of the second embodiment.

FIG. 21A and FIG. 21B each show a first modified example of the ligating unit 67 in the suturing apparatus 1 according to the second embodiment (refer to FIG. 14 and FIG. 20B). In the present modified example, as shown in FIG. 21A, one thin sheet shaped soft receiving plate member 81 is slidably inserted by the threads 21 connected to the two T-shaped bars 69 respectively, as shown in FIG. 21A.

The receiving plate member 81 is made of a material with its biological compatibility such as nylon, fluorine resin, or living body absorbing member, for example. Two side holes 82 are drilled at the receiving plate member 82, and the threads 21 of the T-shaped bar 69 each are inserted into these holes.

It is desirable that the size of the receiving plate member 81 can be inserted into the sheath section 7 of the over-tube 2 when the ligating unit 67 is mounted on the suturing apparatus 1 and the endoscope 5 is free of interfering insertion or field of view. It is preferable that the size of the plate member is at least 5 mm in width, for example, is 10 mm in length, and is about 0.5 mm or more in thickness.

Now, operation of the above constructed modified example will be described here. In the present modified example, when the living tissues 47a and 47b are manipulated to be ligated by the threads 21 by means of the suturing apparatus 1, the receiving member 71, the stopper 70, the tube 73, and the receiving plate member 81 move to the distal end side. Then, the receiving plate member 81 abuts against the living tissue 47a.

In this manner, as shown in FIG. 21B, while the living tissues 47a and 47b are pinched between the receiving plate member 81 and the T-shaped bars 69 each, the thread 21 can be received by the receiving plate member 81. At this time, the thread 21 does not come into direct contact with the surface of the living tissue 47a because the thread is positioned on the surface of the receiving plate member 81.

Therefore, in the ligating unit 67 of the present modified example, when the ruptured living tissues 47a and 47b are ligated by the thread 21, the thread 21 does not come into direct contact with the living tissue 47a. Thus, there is no possibility that the thread 21 cuts into the living tissue 47a, and the living tissue is ruptured.

Ligation is carried out in the form that the living tissues 47a and 47b are sandwiched between the receiving plate member 81 which is larger in area than the thread 21 and the T-shaped bar 69. Thus, the living tissues 47a and 47b in broader range can be reliably sutured.

FIG. 22 shows a second modified example of the ligating unit 67 in the suturing apparatus 1 according to the second embodiment (refer to FIGS. 14 to FIG. 20B).

In the present modified example, as shown in FIG. 22, the shape of the T-shaped bar 36 is identical to that according to the first embodiment. Here, a connecting pipe 72 is fixed to the distal end side of the loop section 68 of the thread 21, the receiving member 71 is inserted, and then, both ends 21a and 21d of the thread 21 is processed as follows. The thread end 21a at one end side of the thread 21 is inserted through a thread insert hole 37a into another thread insert hole 37b of one T-shaped bar 36a. The thread end 21d at the other end side of the thread 21 is inserted through a thread insert hole 37c into another thread insert hole 37d of the other T-shaped bar 36b. Then, the thread ends 21a and 21d both of the thread 21 are bundled collectively. In this state, these thread end are knotted at a portion of the threads 21b and 21c provided in parallel to each other at the distal end side of the receiving member 71, and one knot 83 is formed.

The knot 83 is formed in the same way as the knots 30a and 30b according to the first embodiment, and can slide on a portion of the threads 21b and 21c. The inner diameter of the receiving member 71 is dimensionally defined such that the knot 83 cannot be inserted. As in the first embodiment, two knots may be formed.

When the ligating unit 67 of the present modified example is manipulated to be ligated, the knot 83 moves to the distal end side instead of the stopper 70. At this time, the thread 21 moves as indicated by the arrow of FIG. 22.

In the present modified example, the following advantageous effect is attained. That is, the tube 73 and the stopper 70 are surely eliminated, and thus, constituent elements of the ligating unit 67 are reduced in number, and the fabrication cost is reduced.

The knotting strength of the knot 83 is changed, whereby the easiness of movement on the threads 21b and 21c of the knot 83 can be changed. Thus, the actuation force quantity of the ligating slider 66 is easily reduced when the knot 83 is moved.

In contrast, when the knot 83 is hardly moved by tightly knotting it, the ligation state caused by the thread 21 can be maintained more strongly. Thus, there is no danger that ligation is easily loosened.

FIG. 23 shows a third modified example of the ligating unit 67 in the suturing apparatus 1 according to the second embodiment (refer to FIG. 14 to FIG. 20B).

The ligating unit 67 of this modified example is constituted such that living tissues are sutured only between one T-shaped bar 69 and the stopper 70 as shown in FIG. 23 without using two T-shaped bars 69 as shown in the second embodiment.

In the ligating unit 67 of the present modified example, one T-shaped bar 69 is fixed to the distal end of one thread 21. This thread 21 is returned at its proximal end side, and the loop section 68 is formed. Further, an end of the return section of this thread 21 is fixed in the connecting pipe 72.

In the present embodiment, a distal end side hole 74 and a proximal end side hole 75 are dripped at the receiving member 71 as well one by one.

When the living tissues 47 to be sutured is extremely narrow in range, the ligating unit 67 according to the present modified example is used. In this case, suturing can be carried out only by narrowing the living tissues only between one T-shaped bar 69 and the stopper 70.

In the case where this ligating unit 67 is used, the suturing apparatus 1 may be such that only one needle lumen 23 and one needle 28 are provided.

When the ligating unit 67 of the present modified example is used, if the ligating unit 67 is manipulated to be ligated, the living tissues are sandwiched and ligated between one T-shaped bar 69 and the tube 73.

In the present modified example, a user can select a ligating unit 67 suitable for a case where the suturing range is narrow. In this case, the number of constituent elements such as T-shaped bars 69 are reduced, and thus the fabrication cost is reduced.

FIG. 24A to FIG. 24D each show a third embodiment of the present invention. In the ligating unit 67 of the present embodiment, the receiving member 71 that has been used in the second embodiment is eliminated. Further, in the present embodiment, as shown in FIG. 24A, the outer diameter of the stopper 70 is substantially equal to that of the ligating sheath 62. The distal end face of the ligating sheath 62 can abut against the proximal end face of the stopper 70.

The cutter sheath 17 is made of a metallically meshed plastics (such as polyetylene, PTFE, or nylon, for example), or alternatively, is formed of a metallic multistart coil. In this manner, excellent rotation traceability is attained.

As shown in FIG. 24B, a cutting member 84 is connected to the distal end of the cutter sheath 17. The cutting member 84 has a substantially L shaped cutout 85. Cutting blades 87 are provided at the distal end side rim and side face rim of the cutout 85. A claw section 86 is provided at the distal end side of the cutout 85.

Now, operation of the present embodiment will be described here. The ligating slider 66 is pushed out in advance in advancing direction before using the suturing apparatus 1 of the present embodiment, whereby the distal end hook 64 is protruded from the distal end of the ligating sheath 62 via the manipulating wire 63. In this state, the loop section 68 of the ligating unit 67 is hooked on the hook 64. In this state, the ligating slider 66 is pulled toward the proximal end side. The manipulating wire 63 is retracted by pulling manipulation of this slider 66, and the hook 64 is retracted into the ligating sheath 62. Subsequently, the loop section 68 of the ligating unit 67 is pulled backwardly via the hook 64, and the connecting pipe 72 is retracted into the ligating sheath 62. The proximal end face of the stopper 70 is supported to be abutted against the distal end face of the ligating sheath 62.

In this state, in accordance with the procedures similar to those of the second embodiment, the living tissues 47a and 47b are ligated as shown in FIG. 24C by means of the ligating unit 67 according to the present embodiment. Then, the slider 66 is slightly advanced to the distal end side, and one portion of the thread 21 at the proximal end side of the stopper 70 is exposed to the distal end side of the cutter sheath 17, as shown in FIG. 24D.

Next, the cutter knob 18 is manipulated to be extruded, whereby the cutter sheath 17 is advanced, and the cutting member 84 is protruded to the distal end side more than the ligating sheath 62. In this state, by manipulation of the cutter sheath 17, the thread 21 exposed to the proximal end side of the stopper 70 is hooked on the claw section 86, as shown in FIG. 24D. Then, the cutter sheath 17 is pulled toward the proximal end side or is rotated in the direction shown in FIG. 24D, whereby the cutting blade 87 of the cutting member 84 cuts the thread 21.

According to the ligating unit 67 of the present embodiment, there is no need to provide the receiving member 71 that has been used in the second embodiment, and the number of parts is reduced. Thus, the fabrication cost can be reduced. The thread 21 extends straight way between the proximal end of the stopper 70 and the hook 64. When the ruptured living tissues 47a and 47b are ligated, it is possible to advance the stopper 70 to the distal end side with a gentle force quantity.

FIG. 25 to FIG. 28 each show a fourth embodiment of the present invention. In the present embodiment, there is provided a ligating unit 107 in which a constitution of the ligating unit 67 is changed as follows in the suturing apparatus 1 of the second embodiment (refer to FIG. 14 to FIG. 20B).

That is, in the ligating unit 107 of the present embodiment, a holding member 88 for holding the thread 21 is provided as shown in FIG. 25. It is preferable that this holding member 88 is made of a plastics such as polypropylene, ABS, polyacetal, or polycarbonate, or alternatively, is made of a material with its comparatively high rigidity and excellent fluid properties such as liquid crystal polymer or polyphthalic amide. In addition, the holding member may be made of a metal such as stainless or aluminum. The outer diameter of the holding member 88 is defined as about 1 mm to 3 mm, for example, and the length of the member is defined as about 5 mm to 10 mm.

As shown in FIG. 26, the holding member 88 is composed of a first member 89 and a second member 90. The first member 89 is provided as a cylindrical member. A large diameter section 91 is provided at the proximal end section of the first member 89. A press-fit section 92 with its diameter smaller than the large diameter section 91 is provided at the distal end section of the first member 89.

At the outer periphery of the distal end side of the large diameter section 91, the annular cutter 27 is engagingly fitted while its cutting blade faces to the distal end side. Thread guides 93a and 93b are provided at the top and bottom two sections at the outer periphery of the proximal end side of the large diameter section 91.

Further, as shown in FIG. 25, engagement claws 106a and 106b are provided at the outer periphery of the distal end side of the large diameter section 91. These engagement claws 106a and 106b are disposed at the right and left two sections which eccentrically deviate by 90 degrees in the peripheral direction relevant to the thread guides 93a and 93b.

An internal cavity 94 is provided in axial direction at the axial center section of the first member 89. A protrusion 95 is provided at the substantially intermediate section in the axial direction of this internal cavity 94. The height of this protrusion 95 is properly about 0.1 mm to 0.3 mm, for example.

In the second member 90, a columnar section 96 is provided at its distal end section. A cylindrical section 97 is provided integrally with the columnar section 96 at the proximal end section of this columnar section 96. An insert shaft 98 is protruded at the center of the columnar section 96. This insert shaft 98 penetrates the inside of the cylindrical section 97, and is inserted into the internal cavity 94 of the first member 89. Further, a fixing internal cavity 99 is provided at the columnar section 96 while the cavity surrounds the insert shaft 98. The press-fit section 92 of the first member 89 can be press-fitted to this fixing internal cavity 99. The length of the fixing internal cavity 99 is properly 1 mm to 3 mm, for example.

Two distal end holes 100a and 100b are provided at the distal end face of the second member 90. As shown in FIG. 27A, the threads 21 are inserted into the distal end holes 100a and 100b one by one. Side holes 101a and 101b are provided at the top and bottom two sections at the outer periphery of the cylindrical section 97 of the second member 90. Further, slits 102a and 102b each are provided adjacently of the side holes 101a and 101b each. Further, two engagement holes 103a and 103b are provided at the cylindrical section 97 as shown in FIG. 27B.

These engagement holes 103a and 103b are disposed at the right and left two sections which eccentrically deviate by 90 degrees in the peripheral direction relevant to the slits 102a and 102b. The engagement claws 106a and 106b of the first member 89 are engaged with the engagement holes 103a and 103b each.

An abutment face 104 of the cutting blade of the cutter 27 is provided at the proximal end side face of the columnar section 96 of the second member 90. Further, an abutment portion 105 of the press-in section 92 is provided in close proximity to the distal end section of the fixing internal cavity 99. A one-sided clearance between the inter diameter of the fixing internal cavity 99 and the outer diameter of the press-in section 92 is defined so as to be smaller than the outer diameter of the thread 21.

An insert shaft 98 of the second member 90 is inserted into the internal cavity 94 of the first member 89. A proximal end face of the insert shaft 98 abuts against the protrusion 95, and the insert depth is restricted. Therefore, the cylindrical section 97 of the second member 90 is engaged with the outside of the cutter 27, and covers the cutting blade of the cutter 27.

As shown in FIG. 26, the thread 21 is inserted into the second member 90 through the distal end holes 100a and 100b, and then, is guided to the outside through the side holes 101a and 101b. Subsequently, as shown in FIG. 25, the thread is guided to the slits 102a and 102b and thread guides 93a and 93b, thereby being guided to the proximal end side of the holding member 88. The loop section 68 of the return section of the thread 21 and linking caused by the connecting pipe 72 of both terminals are similar to those of the second embodiment.

Now, operation of a fourth embodiment will be described here. Before using the suturing apparatus 1 of the present embodiment, in the same manner as in the second embodiment, the ligating unit 107 is mounted in advance on the distal end of the needle 28 and the ligating device 4. During this mounting work, first, the manipulating wire 63 is advanced, and the hook 64 is protruded from the distal end opening of the ligating sheath 62. In this state, the loop section 62 of the return section at the proximal end section of the thread 21 is hooked on the hook 64. Then, the manipulating wire 63 is retracted, and the hook 64 is retracted into the ligating sheath 62. In thus manner, the convergent section 77 of the holding member 88 is supported to be inserted into the distal end opening of the ligating sheath 62. Next, the T-shaped bars 69 are inserted into the distal end internal cavities of the two needles 28 respectively, whereby setup of the suturing apparatus 1 terminates.

Next, while the ruptured living tissues 47a and 47b are observed by the endoscope, the living tissues are suctioned into the treatment lumen 40 through the side opening 8 of the over-tube 2. Then, two needles 28 are protruded, and the ruptured living tissues 47a and 47b are punctured. In this state, the T-shaped bars 69 are extruded respectively from the two needles 28.

The needles 28 are then removed, whereby the two threads 21 of the ligating unit 107 is set to be inserted into the ruptured living tissues 47a and 47b, as shown in FIG. 28.

In this state, the manipulating wire 63 is retracted. By this manipulation, the proximal end section of the thread 21 is retracted into the ligating sheath 62 via the hook 64, and the holding member 88 moves toward the distal end. As a result, the ruptured living tissues 47a and 47b are tightly bound.

When the manipulating wire 63 is further retracted, the distal end face of a second member 90 of the holding member 88 abuts against the ruptured living tissues 47a and 47b. At this time, the ruptured living tissues 47a and 47b serve as stoppers. Thus, the first member 89 relatively advances, and the second member 90 is retracted. Therefore, the insert shaft 98 of the second member 90 breaks the protrusion 95, and is inserted into the internal cavity 94 of the first member 89.

At this time, the press-fit section 92 of the first member 89 advances in the direction of the fixing internal cavity 99 of the second member 90. Thus, an intermediate section of the thread 21 is fixed to be sandwiched between an internal face of the fixing internal cavity 99 and an external face of the press-fit section 92. Subsequently, when the press-fit section 92 of the first member 89 further advances in the direction of the fixing internal cavity 99 of the second member 90, the cutting blade of the cutter 27 of the first member 89 abuts against the abutment face 104 of the second member 90. In this manner, the intermediate section of the thread 21 is cut by the cutting blade of the cutter 27. At this time, the cutting terminal of the thread 21 is sandwiched and fixed between the internal face of the fixing internal cavity 99 and the external face of the press-fit section 92.

At a time when the distal end section of the press-fit section 92 abuts against the abutment section 105, the engagement claws 106a and 106b of the first member 80 are engaged with the engagement holes 103a and 103b of the second member 90. In this manner, the first member 89 and the second member 90 are connected with each other.

The ligating sheath 62 and the holding member 88 are separated from each other by cutting of the thread 21, and the ligating device 4 and the ligating unit 107 are completely separated from each other. Thereafter, the over-tube 2 and the endoscope 5 are removed from the body cavity of the patient, only the thread 21 held in its tightly bound state by means of the holding member 88 is left in the patient's body. Then, tightly binding operation of the ruptured living tissues 47a and 47b completes.

In the above constructed present embodiment, an advantageous effect similar to those of the first and second embodiments is attained. Further, in the present embodiment, the following advantageous effect is attained in addition to those of the first and second embodiments.

The ruptured living tissues 47a and 47b are tightly bound, and at the same time, the thread 21 is cut, and separating manipulation can be carried out by only manipulation of the ligating slider 66. Thus, the manipulation count of the suturing apparatus 1 is reduced as compared with those of the first and second embodiments, treatment/manipulation is simplified, and the treatment time is further reduced.

In addition, the cutting terminal of the thread 21 is housed in the holding member 88. Thus, when any endoscopic treatment is carried out after ligation, the field of view or actuation of the endoscope or other treatment devices is hardly interfered.

The cutter 27 is provided at the ligating unit 107 itself, and thus, a new cutter is always used. As a result, the thread 21 can be reliably cut.

The cutter sheath 17 at the outside of the ligating sheath 62 according to the second embodiment is eliminated. Thus, the ligating device 4 is reduced in diameter, and the ligating device 4 can be inserted into the ligating lumen 24.

Figure 29A:
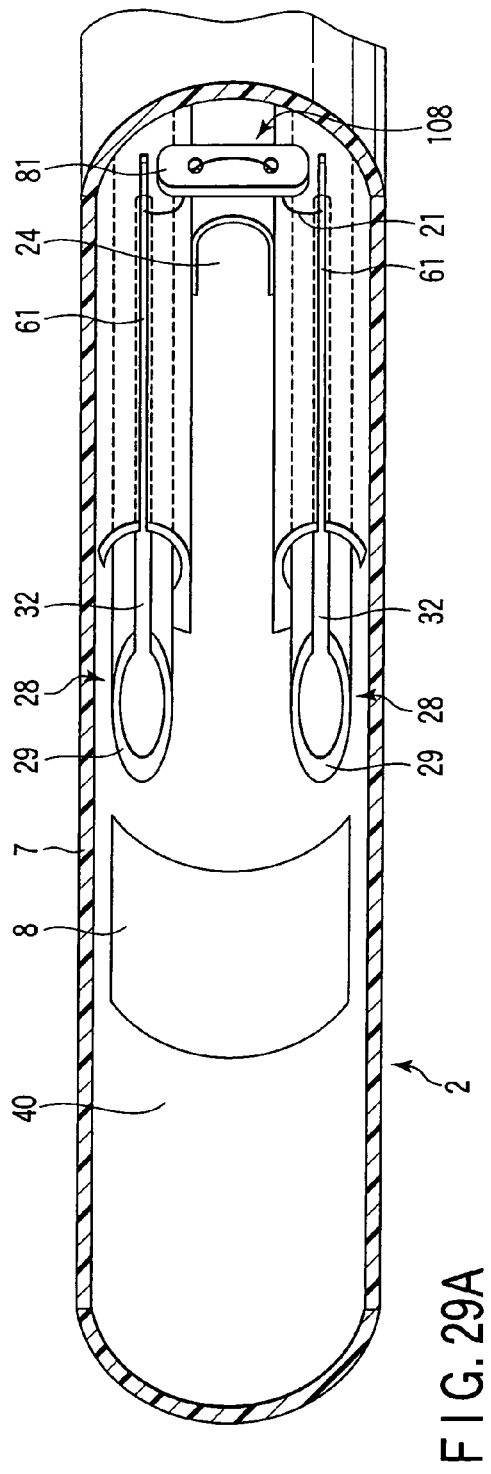
FIG. 29A is a perspective cross section showing a part of a distal end of an over-tube when a ligating unit in a suturing apparatus according to a fifth embodiment of the present invention is mounted.
Figure 29C:
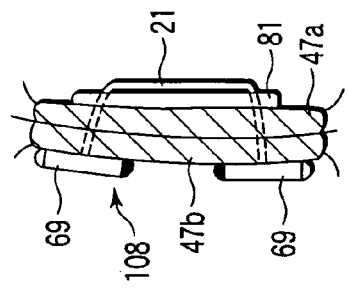
FIG. 29C is a perspective view showing a state in which living tissues are ligated by a ligating unit in the suturing apparatus according to the fifth embodiment.
Figure 29B:
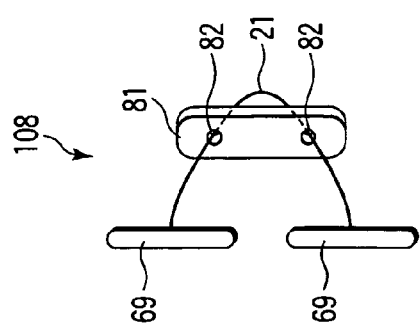
FIG. 29B is a perspective view showing the ligating unit in the suturing apparatus according to the fifth embodiment.
Figure 33:
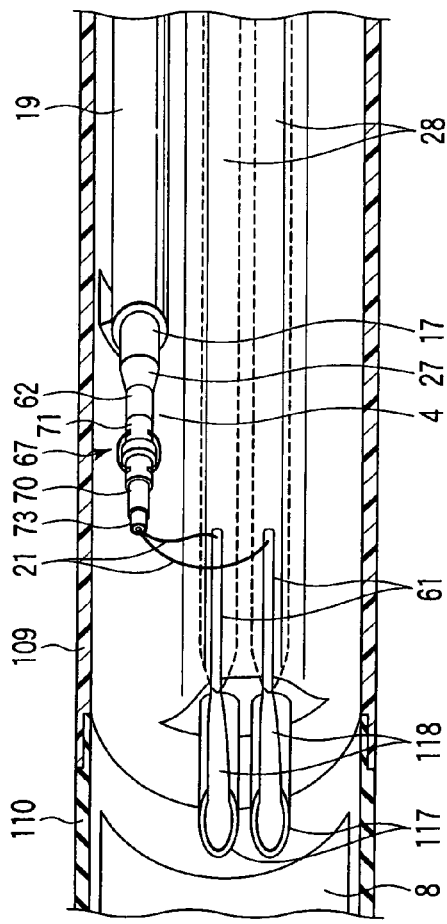
FIG. 33 is a perspective cross section showing the over-tube when a ligating unit in the suturing apparatus according to the sixth embodiment is mounted.

FIG. 29A to FIG. 29C each show a fifth embodiment of the present invention. In the present embodiment, there is provided a ligating unit 108 in which a constitution of the ligating unit 38 of the suturing apparatus 1 according to the first embodiment (refer to FIG. 1A to FIG. 12) has been changed as follows.

That is, in the ligating unit 108 of the present embodiment, as shown in FIG. 29B, the T-shaped bars 69 are fixed respectively to both ends of the thread 21. On the thread 21, the above described receiving plate member 81 of FIG. 21A and FIG. 21B is slidably inserted.

A length from the connecting portion of the T-shaped bar 69 and the thread 21 to the center of the thread is defined to be equal to or smaller than a length in the axial direction of the side opening 8 of the over-tube 2. FIG. 29A shows a state in which the ligating unit 108 is mounted on the suturing apparatus 1. Further, FIG. 29C shows a state after the ruptured living tissues 47a and 47b are ligated by the ligating unit 108.

In this suturing apparatus, the ligating device 4 is eliminated, and the ligating device 4 is not inserted into the ligating lumen 24. Thus, the ligating lumen 24 may not be provided.

Now, operation of the above constructed present embodiment will be described here. Here, only elements different from those of the first embodiment will be described.

That is, when the ligating unit 108 of the present embodiment is used, if the pusher slider 16 is pressed after the needle 28 has been punctured into the ruptured living tissues 47a and 47b, the T-shaped bar 69 attempts to protrude from the needle 28. However, a half of the length of the thread 21 is set to be equal to or smaller than a length in the axial direction of the side opening 8. Thus, the distal end side surface of the receiving plate member 81 abuts against the living tissues 47a before the T-shaped bar 69 protrudes from a tip of the needle 28. When the pusher slider 16 is further advanced, the living tissues 47 suctioned from the side opening 8 are compressed in the axial direction of the over-tube 2. Then, the T-shaped bar 69 protrudes from the tip of the needle 28.

When the T-shaped bar 69 is protruded, the living tissues 47a and 48b are compressed. This means that ligation has been already carried out. Then, the T-shaped bar 69 protrudes to the living tissue 47b, and its ligation state is held at a time when slip-off proofing is effected.

At this time, the receiving plate member 81 serves as the stopper 70 of the second embodiment.

The length of the thread 21 is adjusted, whereby the tightening quantity of the living tissues 47a and 47b can be changed.

In the above constructed present embodiment, an advantageous effect similar to those of the first and second embodiments can be attained. Further, in the present embodiment, the following advantageous effect is attained in addition to those of the first and second embodiments.

That is, in the present embodiment, ligation completes by manipulating the T-shaped bar 69 to be extruded from the needle 28. Thus, ligating manipulation as in the first and second embodiments is eliminated. In addition, a manipulation for cutting a redundant thread 21 is eliminated. As a result, treatment/manipulation is more simplified, and the treatment time is further reduced.

In addition, the ligating device 4 is eliminated, and the number of parts in the ligating unit 108 is reduced. Thus, the fabrication cost can be reduced.

The ligating device 4 is eliminated, and thus, a sectional area of the endoscope lumen 25 increases, making it easy to insert the endoscope. Further, a stronger suction can be applied than a case where suction is applied via endoscope lumen. Alternatively, the ligating lumen 24 is eliminated, thereby making it possible to reduce the over-tube 2 in diameter. As a result, the over-tube 2 can be easily inserted into the patient's body.

FIG. 30A to FIG. 36B each show a sixth embodiment of the present invention. In the present embodiment, a constitution of the over-tube 2 of the suturing apparatus 1 according to the first embodiment (refer to FIG. 1A to FIG. 12) is changed as follows.

That is, in the present embodiment, the sheath section 7 of the over-tube 2 is formed of a proximal end sheath 109, an intermediate sheath 110, and a distal end sheath 111, as shown in FIG. 30A. The inner and outer diameters of the proximal end sheath 109, the intermediate sheath 110, and the distal end sheath 111 are dimensionally defined to be substantially equal to each other.

The proximal end section of the proximal end sheath 109 is connected to the distal end of the connecting section 6. The proximal end section of the intermediate sheath 110 is connected to the distal end of this proximal end sheath 109 by means of bonding or the like. The distal end sheath 111 is removably connected to the distal end of the intermediate sheath 110.

The proximal end sheath 109 is formed of a plastic material which is comparatively flexible, the plastic material having excellent transparency such as polyurethane, vinyl chloride, polyurethane based elastomer, polystyrene based elastomer, or polyolefin based elastomer, for example. The outside of the proximal end sheath 109 can be observed through a wall face of this proximal end sheath 109 by means of the endoscope 5 inserted into the endoscope lumen 25.

As shown in FIG. 32B, two needle lumens 23 are integrally formed at the proximal end sheath 109. The two needle lumens 23 are disposed adjacently in parallel to each other. A distal end of the needle lumen 23 terminates in close proximity to the distal end of the intermediate sheath 110. A distance between centers of the two needle lumens 23 changes depending on the diameter of the needle lumen 23 itself. It is desirable that the distance is about 3 mm to 5 mm, for example.

As shown in FIG. 32A, slits 61 are provided respectively at the distal ends of the two needle lumens 23. A tubular guide 117 is inserted into, and is fixed to, the distal end internal cavity of the needle lumen 23.

Further, as shown in FIG. 32C, a tube 119 is fixed to the inner periphery face side of the proximal end sheath 109. The ligating lumen 24 is formed by the internal cavity of this tube 119.

The tube 119 has flexibility, and is formed of a plastic based tube such as fluorine resin, polyethylene, polyamide, polyimide, polyurethane, or various thermoplastic elastomers, or alternatively, is formed of a metal coil. This tube may be covered with a plastic tube at the outside of the metal coil or may be a metallically meshed plastic tube so that a kink hardly occurs.

The tube 119 is fixed to a fixing member 120. This fixing member 120 is engaged into a side hole 120 drilled on the side wall of the proximal end sheath 109, and is fixed so as to maintain air tightness. The fixing method is not limited thereto.

The intermediate sheath 110 is formed of a comparatively hard and transparent plastic material such as polycarbonate, ABS, or norbornen resin. The treatment lumen 40 is formed by the internal cavity of the intermediate sheath 110.

Further, as shown in FIG. 30B, the side opening 8 is provided on the peripheral face of the intermediate sheath 110. A male screw section 114 is formed on the inner periphery face at the distal end side of the intermediate sheath 110. When the needle 28 is completely protruded from the distal end of the two needle lumens 23, the distal end of the needle 28 is defined so as to be disposed at the distal end side more than the intermediate sheath 110.

The distal end sheath 111 has a sheath main body 113 formed of a plastic material which is comparatively flexible, the plastic material having its excellent transparency such as polyurethane, vinyl chloride, polyurethane based elastomer, polystylene based elastomer, or polyolefin based elastomer. As shown in FIG. 30B, a ring shaped connecting member 115 having a male screw section is fixed at the proximal end side of the sheath main body 113. Then, the male screw section of the connecting member 115 is screwed with the male screw section 114 of the intermediate sheath 110, whereby the distal end sheath 111 is removably connected to the intermediate sheath 110. Further, the distal end valve 112 is fixed at the distal end side of the sheath main body 113.

The distal end valve 112 is formed of various rubbers such as silicon rubber, or alternatively, is formed of a comparatively flexible plastic material such as various thermoplastic elastomers, polyurethane, vinyl chloride, polyethylene, polyamide, or polytetrafluoroethylene. The distal end of this distal end valve 112 is rounded in a hemispheric shape or canon shape. A cross shaped cut-in 116 is provided at the distal end spherical section of this distal end valve 112. Four flaps 122 are provided by the cut-in 116.

While the endoscope 5 is not inserted into the cut-in 116, the flap 122 is closed, and the distal end valve 112 is maintained in its spherical shape or canon shape, whereby air tightness between the distal end of the distal end sheath 111 and the outside is maintained.

When the endoscope 5 is pushed into the cut-in 116, the flap 112 opens, and the endoscope 5 can be inserted.

The shape of the cut-in 116 is not limited to the cross shape, and the number of the cut-ins 116 or flaps 122 is not limited to four.

The guide 117 is formed of a metal pipe such as stainless, or alternatively, is formed of a plastic tube such as fluorine resin, polyethylene, polyamide, polyimide, polyurethane, or various thermoplastic elastomers. The proximal end side of the guide 117 is inserted into, and fixed to the internal cavity of the needle lumen 23. The distal end side of the guide 117 is fixed to the internal faces of the proximal end sheath 109 and the intermediate sheath 110.

As shown in FIG. 31, the distal end of the guide 117 is disposed in close proximal to the side opening 8. The needle 28 can slide at the internal cavity of the guide 117. Further, the proximal end internal face of the guide 117 is tapered so as to be hardly caught when the needle 28 is inserted.

As shown in FIG. 32A, on the side wall of the guide 117, the guide slit 118 extends from the distal end to the close proximity of the proximal end. The guide 117 is mounted so that orientation of the guide slit 118 coincides with the slit 61 at the distal end of the needle lumen 23. The proximal end of the guide slit 118 is located at the proximal end of the slit 61. Alternatively, it may the located at any position between the proximal and distal ends of the slit 61.

The width of the guide sit 118 at a portion where the guide 117 is inserted into the ligating lumen 23 is dimensionally defined such that the thread 21 can be easily inserted. The width of the guide slit 118 at a portion protruding from the ligating lumen 23 increases gradually to the distal end.

Figure 34:
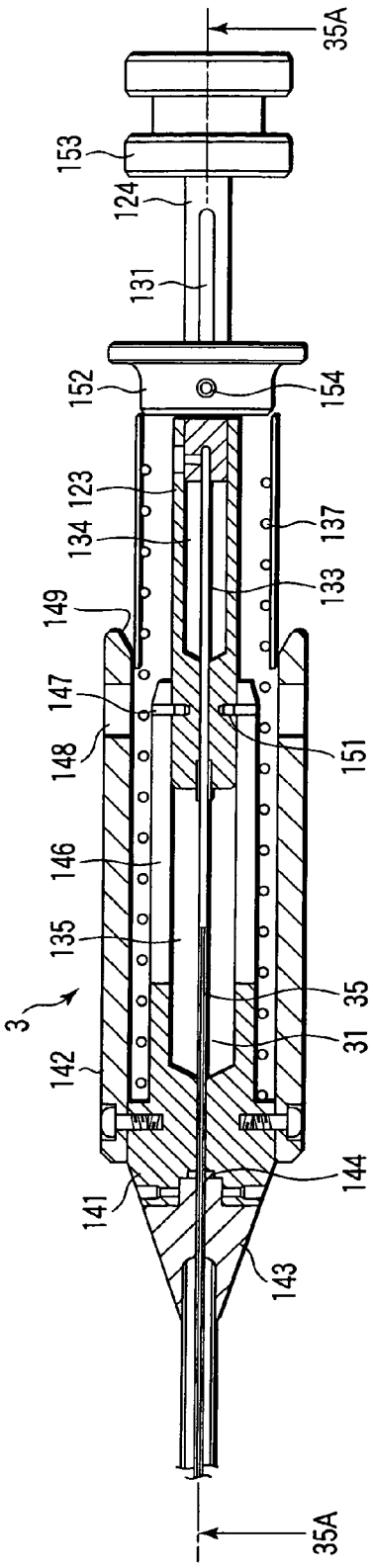
FIG. 34 is a longitudinal cross section showing an internal constitution of a needle manipulating section in the suturing apparatus according to the sixth embodiment.

As shown in FIG. 34, the needle manipulating section 3 is composed of an annular outside housing 142, a needle slider 123, and a pusher slider 124.

An annular inside housing 141 is fixed in a coaxial manner at the inside of the outside housing 142. A coaxial section of the inside housing 141 has an internal cavity 135.

As shown in FIG. 35A, a screw hole 145 is provided at the outside housing 142. At a portion of this screw hole 145, the base member 12 (refer to FIG. 1A) is mounted by means of a mounting screw (not shown).

A cone shaped distal end section 143 is fixed at the distal end side of the inside housing 141. An internal cavity is provided at the coaxial section of this distal end section 143. The internal cavity of the inside housing 141 communicates with that of the distal end section 143. An O-ring 144 is fixed at communicating sections between the internal cavity of the inside housing 141 and that of the distal end section 143. The proximal end section of the connecting sheath 11 is connected at the distal end side of the distal end section 143.

As shown in FIG. 35B, an annular gap 150 is formed between the proximal end side of the inside housing 141 and the outside housing 142.

A shaft shaped axial needle slider 123 is slidably inserted into the proximal end side of the internal cavity 135 of the inside housing 141.

As shown in FIG. 34, two side holes 148 are formed at the side wall of the outside housing 142. Further, two slits 146 are extended in an axial direction on the side wall of the inside housing 141. Two screw holes 151 are provided at the distal end side of the needle slider 123. The proximal end section of the slip-off proof 147 is screwed and fixed to these holes 151 each. The distal end section of each slip-off proof 147 is inserted into the slit 146. Then, the slip-off proof 147 is removable via the side hole 148.

As shown in FIG. 35A, two slits 140 are provided on the side wall of the inside housing 141. These slits 140 are disposed at a position displaced by 90 degrees in the circumferential direction of the slit 146. The slit 140 is extended to the proximal end side of the inside housing 141.

The needle sheath 31 is removably fixed at the distal end of the internal cavity 134 of the needle slider 123. The needle sheath 31 is inserted into the internal cavity of the O-ring 144 as well. Here, the outer diameter of the needle sheath 31 is larger than that of the O-ring 144 so as to maintain air tightness between these elements.

A slit 136 is extended in an axial direction at the needle slider 123. A needle flange 152 with its large outer diameter is provided at the proximal end side of the needle slider 123. As shown in FIG. 35C, at this needle slider 152, a small hole 125 and a large hole 126 are provided in a coaxial manner in a direction orthogonal to the axial direction. The internal diameter of the large hole 126 is larger than that of the small hole 125.

The pusher slider 124 is slidably inserted into the proximal end side of the internal cavity 134 of the needle slider 123. A slit 131 is extended in an axial direction on the side wall of the pusher slider 124. A pusher flange 153 with its large outer diameter is provided at the proximal end side of the pusher slider 124.

A stopper receiver 132 is provided at the distal end of one side of the slit 131. This stopper receiver 132 is formed by a hole with its inner diameter identical to that of the large hole 126. The inner diameter of the small hole 125 and the width of the slit 131 are dimensionally identical to each other.

When the pusher slider 124 is inserted into the needle slider 123, the center axes of the small hole 125, the large hole 126, the slit 131, and the stopper receiver 132 are disposed to be on the same plane.

As shown in FIG. 35C, a pin 127 is slidably inserted into the large hole 126, the stopper receiver 132, the slit 131, and the small hole 125. A stopper 128 with its increased outer diameter is provided at one end of the pin 127. The diameter of the stopper 128 is defined to be smaller than the internal diameter of the larger hole 126 and the stopper receiver 132 each, and is defined to be larger than the width of the slit 131 and the inner diameter of the small hole 125. The outer diameter of the pin 127 other than the stopper 128 is smaller than the width of the slit 131 and the small hole 125.

A spring 129 made of a coil spring is inserted into the large hole 126 at the lower side than the stopper 128. This spring 129 is fitted by means of a spring stop 130 so as not to slip off.

By the biasing force of the spring 129, in a natural state, the stopper 128 is disposed at a position across the stopper receiver 132 and the large hole 126. At this time, a protrusion end 154 protruding from the outer periphery of the needle flange 152 is formed at one end of the pin 127. The protrusion end 154 is formed in a smooth hemispheric shape.

A rod 133 is removably connected at the distal end of the pusher slider 124. The proximal end side of the pusher wire 35 is fixed at the distal end of the rod 133.

A screw stop 139 is screwed and fixed at the distal end side more than the slit 131 of the pusher slider 124 in a direction orthogonal to the axial direction. The center axes of the spring stop 139, the slit 136 of the needle slider 123, and the slit 140 of the inside housing 141 are disposed on the same plane. In this manner, the spring stop 139 can slide at the inside of the slit 136 and the slit 140 each.

A spring 137 formed of a coil spring is inserted into a gap 150. The proximal end side of this spring 137 is fixed by means of the spring stop 139. The proximal outer periphery of the spring 137 is covered with a spring cover 138. The proximal end of the spring cover 138 is fixed to the spring stop 139.

A tapered section 149 is formed on the proximal end internal face of the outside flange 142. While the needle slider 123 is completely retracted from the inside housing 141, the protrusion end 154 is positioned at the inside more than the proximal end inner diameter of the tapered section 149 and at the outside more than the distal end inner diameter (i.e., inner diameter of the outside housing 142) of the tapered section 149.

When the protrusion end 154 is pushed against the biasing force of the spring 129, and is moved to a position of the inner diameter of the outside housing 142, the stopper 128 slips off from the stopper receiver 132, and is defined so as to be positioned at the internal cavity of only the large hole 126.

The spring 137, the spring cover 138, and the spring stop 139 may not be always be provided.

Now, operation of the above constructed suturing apparatus 1 according to the present embodiment will be described here. Here, only elements different from those of the first and second embodiments will be described. A distal end sheath 111 is removed from an intermediate sheath 110 before the ligating unit 67 is mounted on the suturing apparatus 1 of the present embodiment. In this state, the ligating device 4 is advanced, and the ligating sheath 62 is protruded from the intermediate sheath 110. Then, the ligating unit 67 is mounted on the ligating device 4.

Next, the needle slider 123 is pushed against the distal end side, and the distal end of the needle 28 is protruded from the intermediate sheath 110. Then, the T-shaped bar 69 is mounted in the needle. Thereafter, the needle slider 123 is pulled back, thereby the needle 28 is retracted in the ligating lumen 23. In this case, the width of the distal end of the guide slit 118 increases, and thus, the thread 21 automatically enters the guide slit 118 without intentionally aligning orientations of the thread 21 and the guide slit 118. If the needle 28 is continuously retracted as is, the thread automatically enters the slit 61.

Then, the distal end sheath 111 is connected to the intermediate sheath 110.

As in the first and second embodiments, the suturing apparatus 1 and the endoscope 5 are inserted into the patient's body, the living tissues 47 are suctioned from the side opening 8.

In this state, the pusher flange 153 is held by hand, and is pushed against the distal end side. While the protrusion end 154 is more proximal than the outside housing 14, the stopper 128 is left in the internal cavities of both of the stopper receiver 132 and the large hole 126. At this time, the needle slider 123 and the pusher slider 124 are integrally engaged with each other. Therefore, the pusher slider 124 moves to the distal end side, and at the same time, the needle slider 123 moved to the distal end side. In this manner, the distal end of the needle 28 protrudes from the distal end of the guide 117, and is punctured into the living tissues 47. At this time, the spring 137 is compressed in accordance with movement of the spring stop 139 of the pusher slider 124, and a biasing force is generated at the spring 137.

When the pusher flange 153 is continuously pressed as is at the distal end side, the protrusion end 154 abuts against a tapered section 149. Subsequently, the protrusion end 154 is pushed into the small hole 125 against the biasing force of the spring 129.

Further, when the protrusion end 154 moves to the distal end side, and is pushed into the small hole 125, the protrusion end reaches a position at which it comes into contact with the internal face of the outside housing 142. Then, the stopper 128 slips off from the stopper receiver 132. In this manner, the needle slider 123 and the pusher slider 124 are released from being integrated with each other. At this time, the needle flange 152 abuts against the proximal end face of the outside housing 142, and the needle 28 is completely protruded.

Further, when the pusher flange 153 is continuously pushed to be in abutment against the needle flange 152, the pusher slider 124 moves to the distal end side. As a result, the T-shaped bar pusher 33 extrudes the T-shaped bar 69 mounted in the distal end internal cavity of the needle 28. At this time, the spring 137 is further compressed, and a string biasing force is generated.

Next, when a hand is released from the pusher flange 153, the pusher slider 124 is returned to the proximal end side by the biasing force of the spring 137. When the protrusion end 154 is returned to the proximal end side of the outside flange 142, the stopper 128 is pushed up by the biasing force of the spring 129, and is fitted with the stopper receiver 132. Then, the pusher slider 124 and the needle slider 123 are integrated with each other. The biasing force of the spring 137 further functions, and both of the needle slider 123 and the pusher slider 124 are pushed back to the initial position.

In the case where the spring 137, the spring cover 138, and the spring stop 139 are not provided, the pusher flange 153 is held by hand, and is pulled back to its original position, whereby manipulation can be carried out similarly.

With the above constitution, the following advantageous effect is attained. That is, in the present embodiment, while the distal end of the needle 28 is exposed to the outside, it is possible to mount the T-shaped bar 69 at the distal end of the needle 28. This makes it very easy to do the mounting work of the ligating unit 67.

The guide slit 118 extending to the distal end side is provided at the guide 117. Thus, when the needle 28 is retracted into the needle lumen 23, the thread 21 is automatically inserted into the guide unit 118 and the slit 61 merely by pulling the needle 28. This makes it easier to do the mounting work of the ligating unit 67.

The guide 117 extends to the close proximity of the proximal end of the side opening 8, and thus, the needle 28 can be guided from the distal end of the ligating lumen 23 to the close proximity of the proximal end of the side opening 8 along the guide 117. Therefore, the needle 28 from the distal end of the ligating lumen 23 to the proximal end of the side opening 8 can be suppressed from being unstable, and thus, the needle 28 can be precisely punctured into the suctioned living tissues.

The needle slider 123 and the pusher slider 124 are engaged with each other until the needle 28 has been completely protruded. Thus makes it possible to puncture the needle 28 and protrude the T-shaped bar 69 merely by pushing only the pusher flange 153. When a hand is released from the pusher flange 153, the needle slider 123 and the pusher slider 124 are automatically returned to the initial position by means of the spring 137. As a result, treatment/manipulation becomes very simplified, and the treatment time can be reduced.

In the present embodiment, two needle lumens 23 are adjacent to each other, and the ligating lumen 24 is not formed between the two needle lumens 23. Thus, intervals of the needles 28 can be reduced. The intervals of the needles 28 are reduced, thus making it possible to puncture the needle 28 into a lower section of the suctioned living tissues. As a result, a deeper portion of the living tissues can be punctured, thus enabling reliable suturing.

Figure 37:
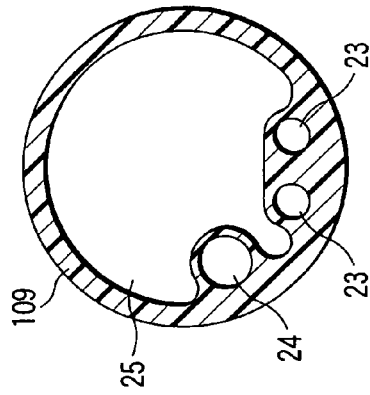
FIG. 37 is a transverse cross section of essential portions showing a first modified example of a proximal end sheath of the suturing apparatus according to the sixth embodiment.

FIG. 37 shows a first modified example of the proximal end sheath of the suturing apparatus 1 according to the sixth embodiment (FIG. 30A to FIG. 36B). In the present embodiment, two needle lumens 23 and the ligating lumen 24 are formed integrally with the proximal end sheath 109.

Figure 38:
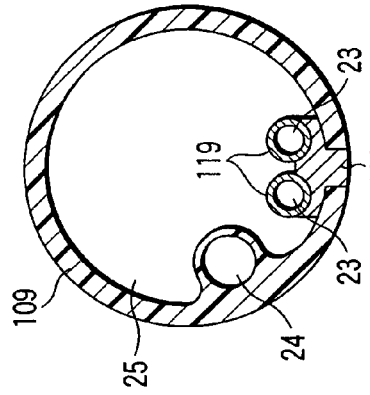
FIG. 38 is a transverse cross section of essential portions showing a second modified example of the proximal end sheath of the suturing apparatus according to the sixth embodiment.
Figure 36A:
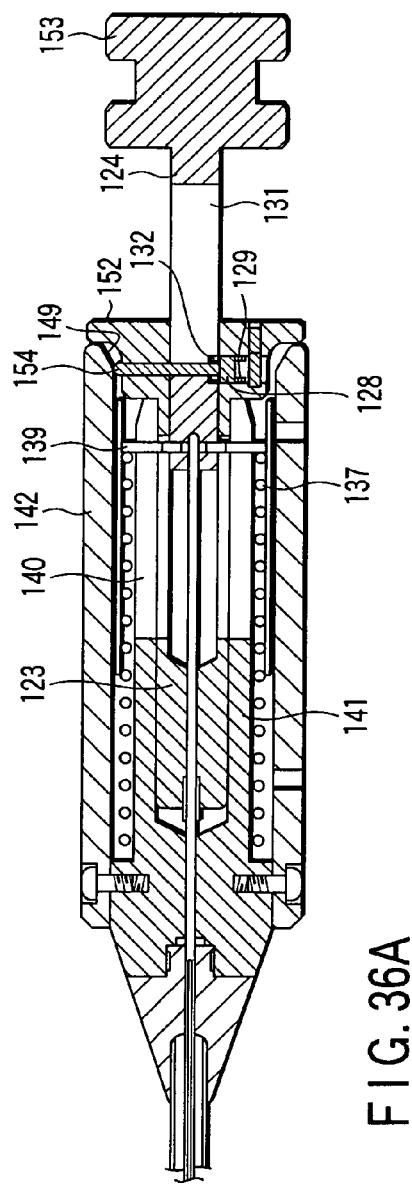
FIG. 36A is a longitudinal cross section, illustrating the pusher slider of the needle manipulating section pushed forward, causing the needle to project completely, in the suturing apparatus according to the sixth embodiment.
Figure 36B:
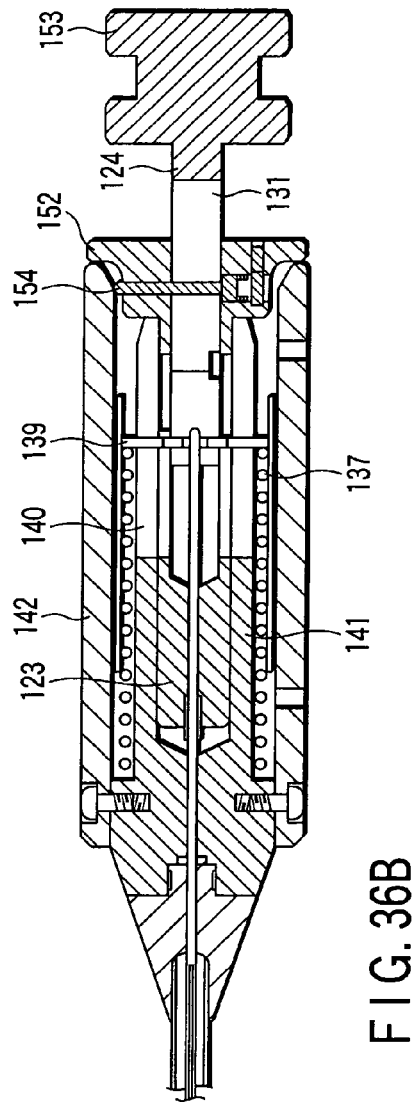
FIG. 36B is a longitudinal cross section showing a state after pushing out a pusher slider of the needle manipulating section in the suturing apparatus according to the sixth embodiment.

FIG. 38 shows a second modified example of the proximal end sheath of the suturing apparatus 1 according to the sixth embodiment (FIG. 300A to FIG. 36B). In the present modified example, the ligating lumen 24 is formed integrally with the proximal end sheath 109. Further, two needle lumens 23 are formed by two tubes 119 disposed in the proximal end sheath 109.

Figure 39:
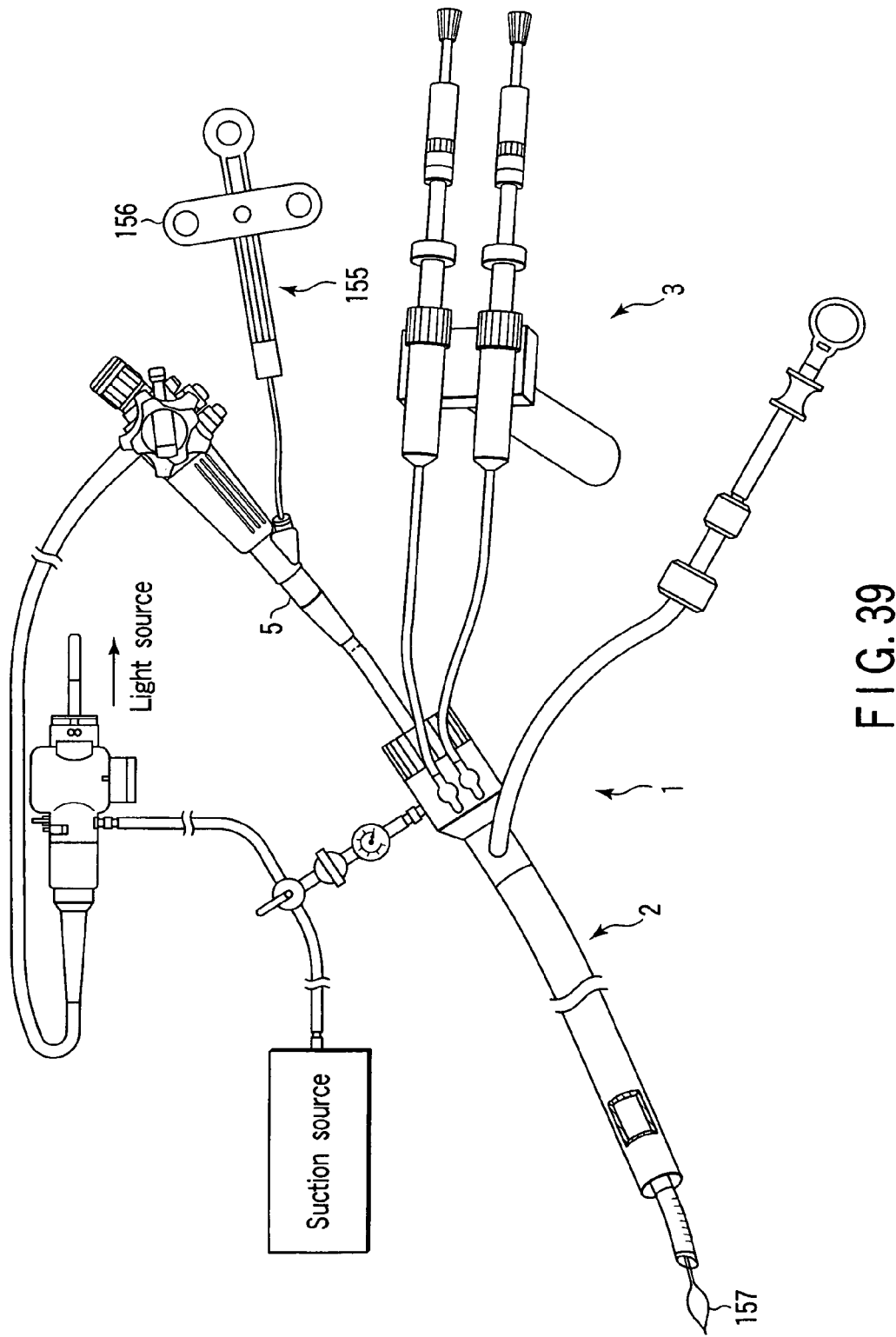
FIG. 39 is a perspective view showing an appearance of an entire resecting/suturing system according to a seventh embodiment of the present invention.
Figure 46A:
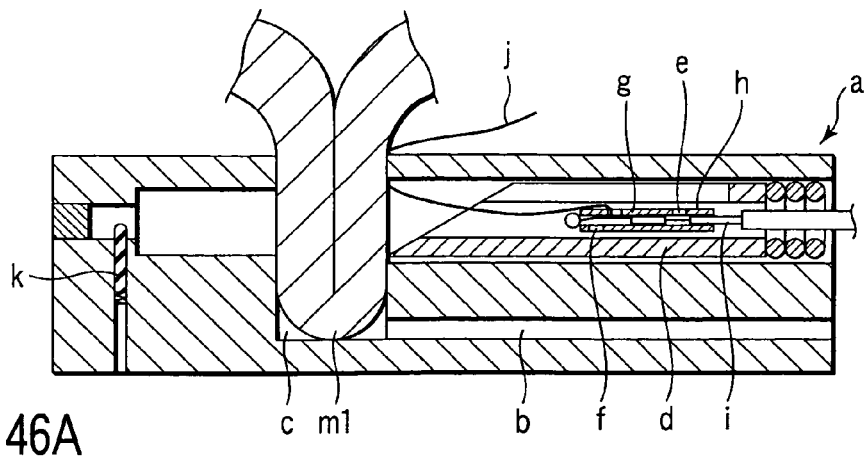
FIG. 46A is a longitudinal cross section of essential portions showing a state in which living tissues have been suctioned into a cavity of a conventional suturing device.
Figure 46B:
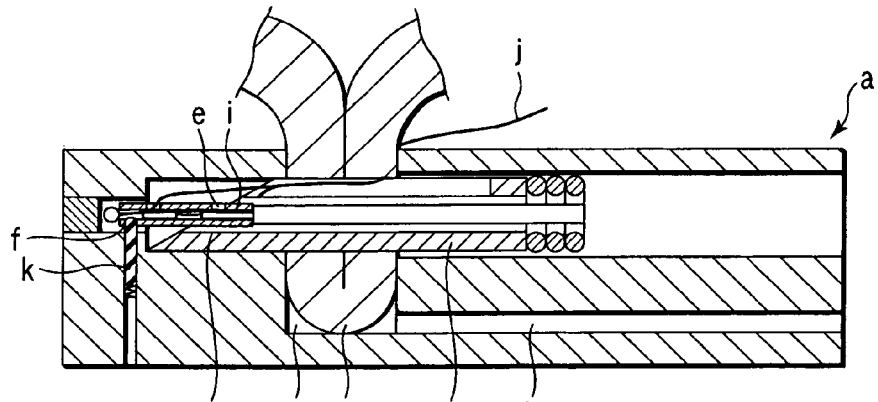
FIG. 46B is a longitudinal cross section of essential portions showing a state in which living tissues have been punctured by a needle of the conventional suturing device.
Figure 46C:
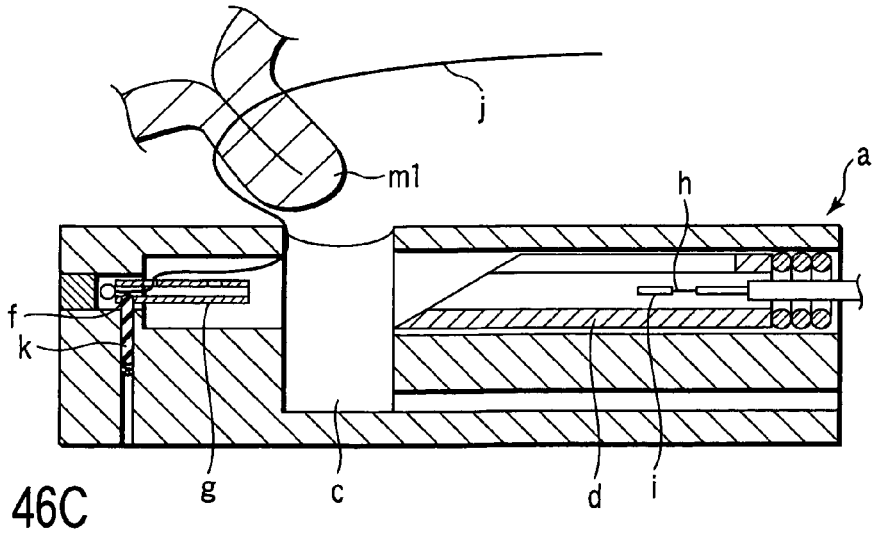
FIG. 46C is a longitudinal cross section of essential portions showing a state in which living tissues have slipped off from the cavity of the conventional suturing device.
Figure 47A:
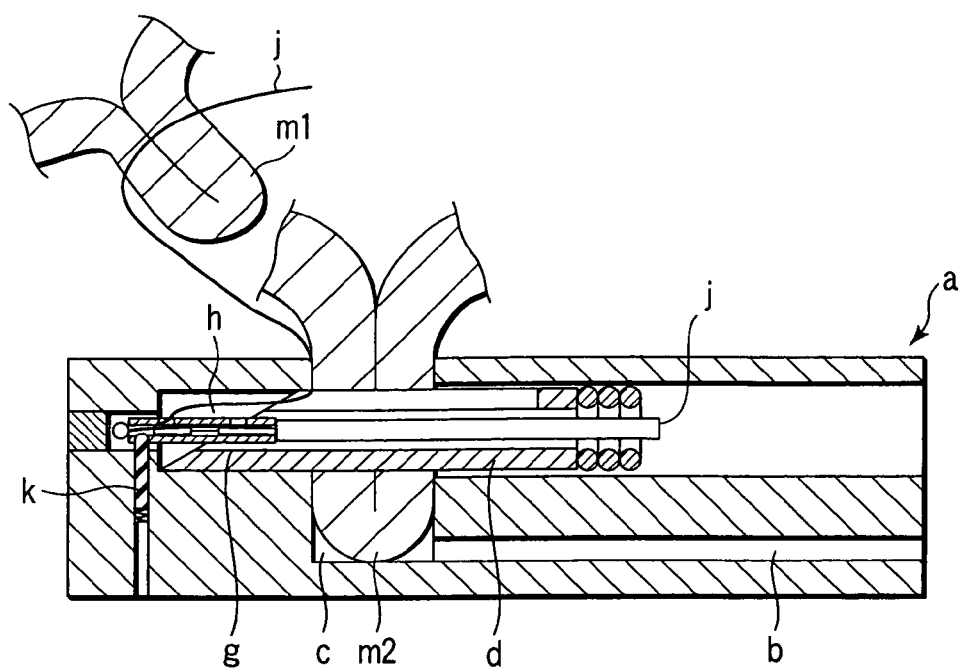
FIG. 47A is a longitudinal cross section of essential portions showing a second working state in which living tissues have been punctured by a needle of the conventional suturing device.
Figure 47B:
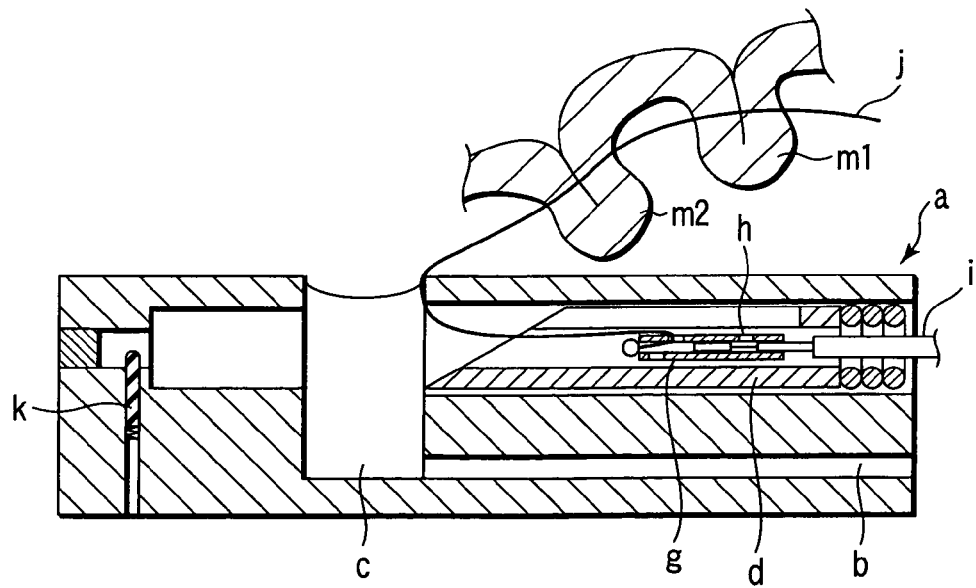
FIG. 47B is a longitudinal cross section of essential portions showing a second working state in which living tissues have slipped off from the cavity of the conventional suturing device.
Figure 48:
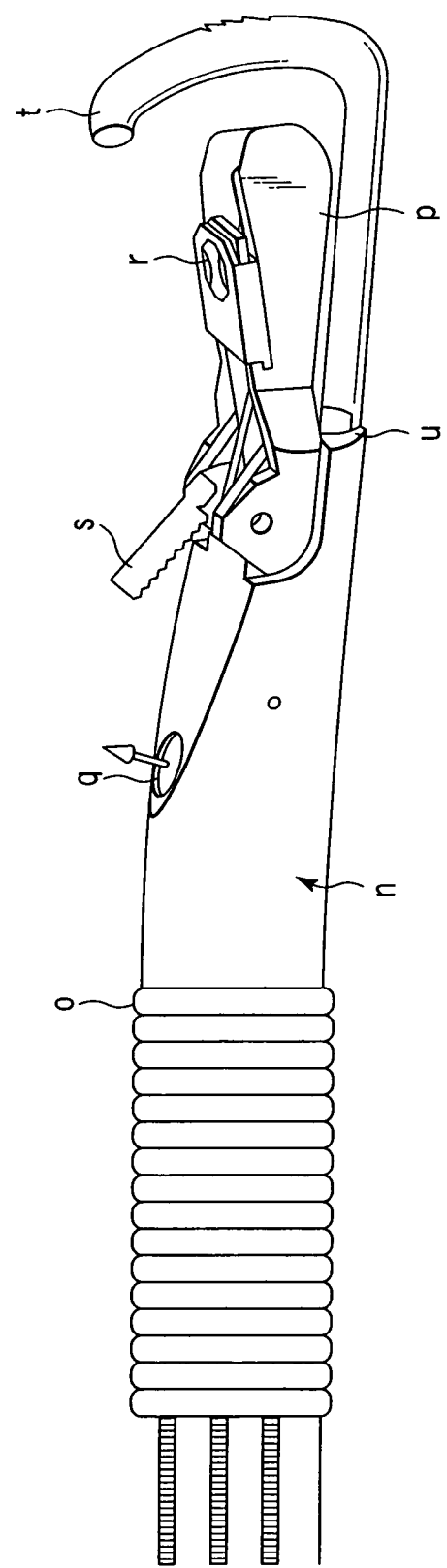
FIG. 48 is a perspective view of essential portions showing a conventional apparatus for forming inflation of living tissues.
Figure 49A:
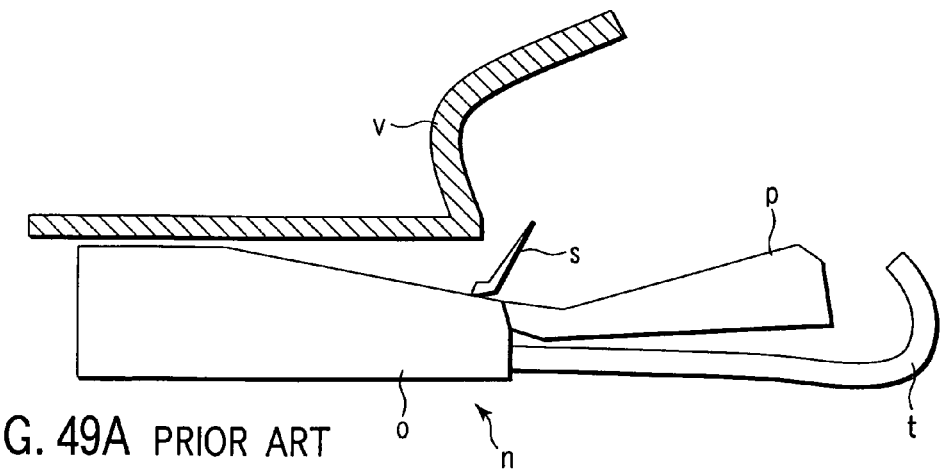
FIG. 49A is a side view of essential portions showing a state in which a flexible tube inserted into a patient's stomach in a peroral manner.
Figure 49B:
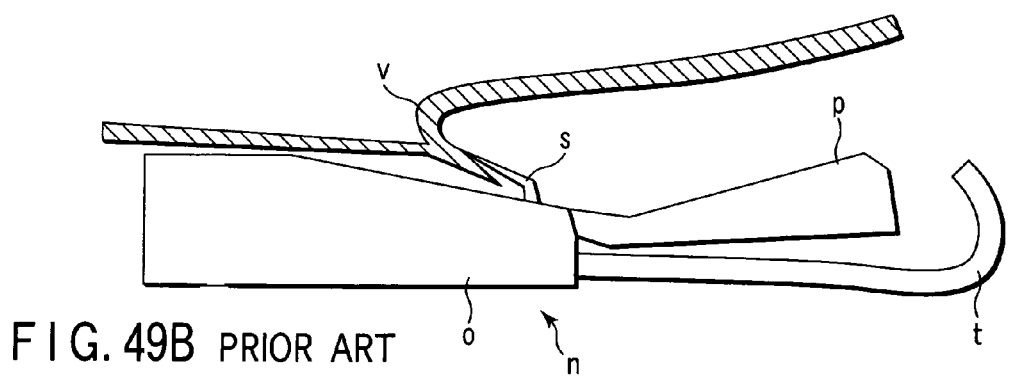
FIG. 49B is a side view of essential portions showing a state in which a esophagogastric junction has gripped by grip means.
Figure 49C:
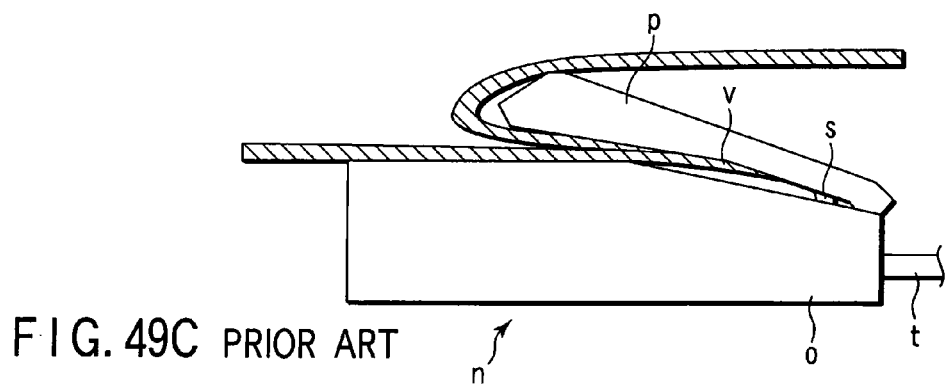
FIG. 49C is a side view of essential portions showing a state in which a movable arm has been manipulated to be turned.
Figure 49D:
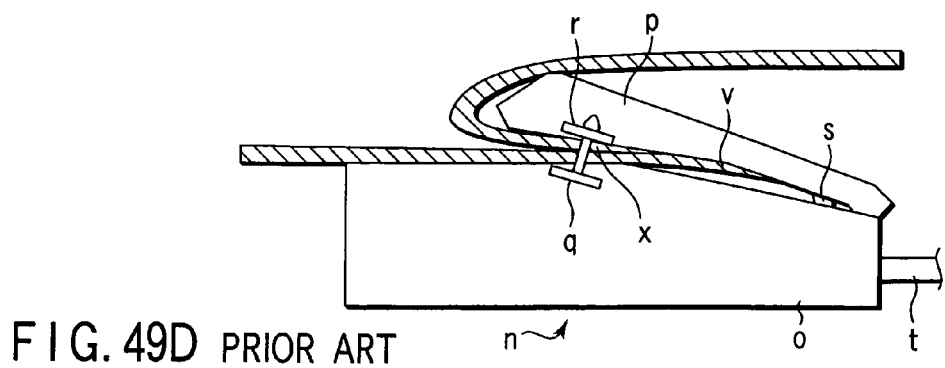
FIG. 49D is a side view of essential portions showing a state in which the esophagogastric junction gripped by the grip means has been engaged by a male fastener and a female fastener.

FIG. 39 to FIG. 42B each show a seventh embodiment of the present invention. A constitution of the suturing apparatus 1 according to the present embodiment is identical to that according to the second embodiment (refer to FIG. 14 to FIG. 20B). A difference is that the endoscope 5 and a high frequency resecting device 155 are used in combination, as shown in FIG. 39.

As shown in FIG. 40A, the high frequency resecting device 155 is inserted through a forceps channel 158 of the endoscope 5.

The high frequency resecting device 155 is used as that called a high frequency snare having a dissecting loop 157 which is an electrode formed in a loop shape at its distal end. This electrode may be formed in various shapes such as scissors shape, hook shape, needle shape, or cup shape without being limited thereto.

The dissecting loop 157 is opened/closed by advancing/retracting manipulation of the slider 156.

Now, operation of the above constructed present embodiment will be described here. First, a local injection liquid such as physiological saline is injected into a sub-mucous layer 160 at the periphery of a lesion site 161 by using an endoscopic injection needle. In this manner, as shown in FIG. 40B, the sub-mucous layer 160 is inflated, and a slight inflation section 163 is formed at the living tissues. At this time, a dying liquid such as indigo carmine is mixed with the local injection liquid. The local injection liquid is locally inserted in a range such that a predetermined margin is defined from the lesion site 161.

Next, the endoscope 5 inserted through the high frequency resecting device 155 is inserted into the patient's body while the endoscope 5 is inserted into the over-tube 2.

As shown in FIG. 41A, the living tissues of the inflation portion 163 is suctioned from the side opening 8. In this state, the needle 28 is punctured, and the T-shaped bar 69 and the thread 21 are punctured into the living tissues of the inflating portion 163.

In this state, the living tissues of the suctioned inflating portion 163 are covered with the dissecting loop 157. At this time, an endoscope image is observed, whereby the locally injected range can be checked as a dying range 162. Thus, as shown in FIG. 41B, the dissecting loop 157 is positioned on the living tissues which is more outside of the dying range 162.

In this state, the slider 156 of the high frequency resecting device 155 is pulled, thereby ligating the living tissues at the periphery of the inflating section 163 suctioned by the dissecting loop 157. In this state, dissection is carried out with high frequency current. In this manner, a mucous membrane 159 including a lesion site 161 and a sub-mucous layer 160 are dissected as shown in FIG. 42A.

Ligation of the ligating unit 67 is carried out by manipulation of the ligating device 4, and the living tissues at a resected are sutured and closed as shown in FIG. 42B.

With the above constitution, the following effect is attained. That is, in the present embodiment, the suturing apparatus 1 and the high frequency resecting device 155 are used in combination. Thus, even in the case where the living tissues in the patient's body are resected, it is possible to suture a resected portion immediately without replacement of another treatment device after resection. As a result, prevention of bleeding from the resected portion or early repair of an ulcer that occurs at the resected portion can be carried out for the patients with lower invasion and easiness.

The living tissue quantity suctioned from the side opening 8 of the suturing apparatus 1 can be adjusted by adjusting a suction pressure. Thus, the depth or size of the living tissues to be resected can be adjusted easily and reliably. The local injection liquid mixing a dying liquid is locally injected into the living tissues, whereby a location of a lesion can be identified. In addition, adjustment of the suction quantity of the living tissues and check of the resection range can be easily carried out, thus making it possible to resect a lesion.

FIG. 43 to FIG. 45 each show an eighth embodiment of the present invention. In the present embodiment, a part of the suturing apparatus 1 according to the second embodiment (refer to FIG. 14 to FIG. 20B) has been changed as follows. Here, only elements different from those of the second embodiment will be described.

As shown in FIG. 43, in the present embodiment, a chamber 164 made of a transparent cylindrical member is removably connected at the distal end of the endoscope 5 instead of the over-tube 2. This chamber 164 is fixed by a medical tape or the like so as not to easily slit off when in use.

The side opening 8 is provided on the side face of the chamber 164. A distal end valve 112 is fixed at the distal end of the chamber 164.

As shown in FIG. 44, a needle tube 166 and a ligating tube 167 are connected at the proximal end side of the chamber 164 so as to communicate with the internal cavity of the chamber 164. Further, as shown in FIG. 45, a suction tube 165 is also connected at the proximal end side of the chamber 164 so as to communicate with the internal cavity of the chamber 164.

A suction port 168 is provided at the proximal end of the suction tube 165. A suction apparatus 54 (refer to FIG. 14) similar to that of the second embodiment is connected to this suction port 168.

The proximal end section of the needle tube 166 is connected with the needle manipulating section 3.

A port 169 is provided at the proximal end of the ligating tube 167. The ligating device 4 is inserted into this port 169.

The suction tube 165, the needle tube 168, and the ligating tube 167 are fixed by a medical tape or the like while these tubes are along a side face of the endoscope 5.

The present embodiment is identical to the second embodiment in operation except that the over-tube 2 is substituted for the chamber 164.

With the above constitution, the following advantageous effect is attained. That is, in the present embodiment, the endoscope 5 is not inserted into another sheath such as over-tube. Thus, the outer diameter of the entire suturing system other than a portion of the chamber 164 is reduced. Further, treatment can be carried out without degrading the flexibility of the endoscope 5 itself, thus making it easy to insert the suturing apparatus into the patient's body or approach a treatment site.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical apparatus comprising:
at least one projecting member;
an introducing sheath configured to be introduced to a target portion in a state in which the projecting member is suspended, wherein the introducing sheath has a sharp distal end which is configured to pierce a living tissue;
an extrusion member disposed inside the introducing sheath and at a proximal side of the at least one projecting member movable in an axial direction with respect to the introducing sheath;
a cover sheath configured to be disposed outside the introducing sheath, the introducing sheath being movable between a first position and a second position with respect to the cover sheath;
an introducing sheath manipulating section provided at a proximal side of the introducing sheath;
an extrusion member manipulating section provided at a proximal side of the extrusion member, wherein the extrusion member manipulating section and the introducing sheath manipulating section are slidably and integrally provided with each other;
a housing having a distal end and a proximal end configured for housing the introducing sheath manipulating section and the extrusion member manipulating section; and
a release member slidably engaged with the cover sheath manipulating section and the introducing sheath manipulating section, wherein movement of the introducing sheath manipulating section toward the distal end of the housing will actuate the sharp distal tip of the introducing member for piercing the living tissue and release an integration between the extrusion member manipulating section and the introducing sheath manipulating section.

2. The apparatus according to claim 1, wherein the projecting member extends in a major axial direction and has an engaging surface which is configured to engage with a living tissue and a connecting portion connected to a suture, and the introducing sheath is suspended detachably.

3. The apparatus according to claim 1, further comprising a sheath section configured to be disposed outside the cover sheath, the cover sheath configured to be arranged on an inner wall of the sheath section, wherein a distal end of the cover sheath is configured to be disposed at a position retracted more proximally than a distal end position of the sheath section.

4. The apparatus according to claim 1, further comprising a sheath section configured to be disposed outside the cover sheath, the cover sheath configured to be arranged on an inner wall of the sheath section, wherein the cover sheath includes a partition wall configured to be disposed on the inner wall of the sheath section.

5. The apparatus according to claim 4, wherein the partition wall is formed integrally with the sheath section.

6. The apparatus according to claim 4, wherein the partition wall is fixed to the sheath section.

* * * * *